US007005498B1

(12) United States Patent
Steinaa et al.

(10) Patent No.: US 7,005,498 B1
(45) Date of Patent: Feb. 28, 2006

(54) METHODS FOR THERAPEUTIC VACCINATION

(75) Inventors: Lucilla Steinaa, Copenhagen (DK); Søren Mouritsen, Birkerød (DK); Anand Gautam, Hørsholm (DK); Iben Dalum, Hørsholm (DK); Jesper Hanning, Birkerød (DK); Dana Leach, Copenhagen Ø (DK); Klaus Gregorius Nielsen, Søborg (DK); Gunilla Karlsson, Copenhagen Ø (DK); Peter Birk Rasmussen, Frederiksberg (DK)

(73) Assignee: Pharmexa A/s, Horsholm (DK)

( * ) Notice: Subject to any disclaimer, the term of this patent is extended or adjusted under 35 U.S.C. 154(b) by 0 days.

(21) Appl. No.: 09/806,703

(22) PCT Filed: Oct. 5, 1999

(86) PCT No.: PCT/DK99/00525

§ 371 (c)(1),
(2), (4) Date: Apr. 30, 2001

(87) PCT Pub. No.: WO00/20027

PCT Pub. Date: Apr. 13, 2000

Related U.S. Application Data

(60) Provisional application No. 60/105,011, filed on Oct. 20, 1998.

(30) Foreign Application Priority Data

Oct. 5, 1998 (DK) ................................ 1998 01261

(51) Int. Cl.
*C07K 9/00* (2006.01)
(52) U.S. Cl. ...................................... 530/324; 530/350
(58) Field of Classification Search ................ 530/324, 530/350
See application file for complete search history.

(56) References Cited

U.S. PATENT DOCUMENTS

| 5,736,142 A | 4/1998 | Sette et al. |
| 2002/0090379 A1 * | 7/2002 | Mouritsen et al. ....... 424/185.1 |

FOREIGN PATENT DOCUMENTS

| EP | 378881 A | * | 7/1990 |
| EP | 0427347 A1 | * | 5/1991 |
| WO | WO9505849 | | 3/1995 |
| WO | WO9507707 | | 3/1995 |
| WO | WO 86/07383 A1 | | 12/1996 |
| WO | WO 96/40789 A1 | * | 12/1996 |
| WO | WO9741227 | | 11/1997 |
| WO | WO9823635 | | 6/1998 |
| WO | WO9831398 | | 7/1998 |
| WO | WO 99/56919 A2 | | 12/1998 |
| WO | WO 99/10375 A2 | | 3/1999 |
| WO | WO 99/40188 A2 | | 8/1999 |

OTHER PUBLICATIONS

Fendly et al. Vaccine Research vol. 2, No. 3, 1991, pp. 129-139.*
$A_{13}$Geneseq$_{13}$101002 Accession No. AAR06310, Dec. 1990.*
$A_{13}$Geneseq$_{13}$101002 Accession No. AAW11505, Sep. 1997.*
$A_{13}$Geneseq$_{13}$101002 Accession No. AAR11896, Jul. 1991.*
Dalum et al. J. Immunol. vol. 157, 1996, pp. 4796-4804.*
Zavala et al. J. Exp. Med. 1983, vol. 157, pp. 1947-1957.*
Dalum, Iben et al.; "Therapeutic . . ." Nature Biotech. vol. 17, Jul. 1999, p. 656-659.
Mackey, Matthew et al.; "Cutting Edge . . ." Journal of Immunology pp. 2094-2096, 1998.
Ridge, John P. et al.; "A conditioned . . ." Nature vol. 393, Jun. 4, 1998, pp. 474-478.
Gemel, Joanna et al.; "structure and . . ." Genomics 35, 253-257 (1996).
Dalum, Iben et al.; "Breaking of B Cell . . ." Amer. Assoc. of Immunology pp. 4796-4804.
Tjoa, Benjamin et al.; "Presentation od . . ." The Prostate 25:266-271 (1996).
Chicz, Roman M. et al.; "Specificity and . . ." J. Exp. Med. vol. 178, Jul.-1993, 27-47.
Candia, Albert F. et al.; "Mox-1 and . . ." Development 116, 1123-1136 (1992).
O'Sullivan, Deirdre et al.; "On the Interaction . . ." J. of Immunology vol. 147, 2663-2669, No. 3, Oct. 15, 1991.
Furukawa, Keiko S. et al.; "A Unique . . ." J. Exp. Med. vol. 169, pp. 585-590 Feb. 1989.

(Continued)

*Primary Examiner*—Christina Chan
*Assistant Examiner*—Marianne DiBrino
(74) *Attorney, Agent, or Firm*—Birch, Stewart, Kolasch & Birch, LLP

(57) ABSTRACT

A method is disclosed for inducing cell-mediated immunity against cellular antigens. More specifically, the invention provides for a method for inducing cytotoxic T-lymphocyte immunity against weak antigens, notably self-proteins. The method entails that antigen presenting cells are induced to present at least one CTL epitope of the weak antigen and at the same time presenting at least one foreign T-helper lymphocyte epitope. In a preferred embodiment, the antigen is a cancer specific antigen, e.g. PSM, Her2, or FGF8b. The method can be exercised by using traditional polypeptide vaccination, but also by using live attenuated vaccines or nucleic acid vaccination. The invention furthermore provides immunogenic analogues of PSM, Her2 and FGF8b, as well as nucleic acid molecules encoding these analogues. Also vectors and transformed cells are disclosed. The invention also provides for a method for identification of immunogenic analogues of weak or non-immunogenic antigens.

5 Claims, 6 Drawing Sheets

OTHER PUBLICATIONS

Figure 1:
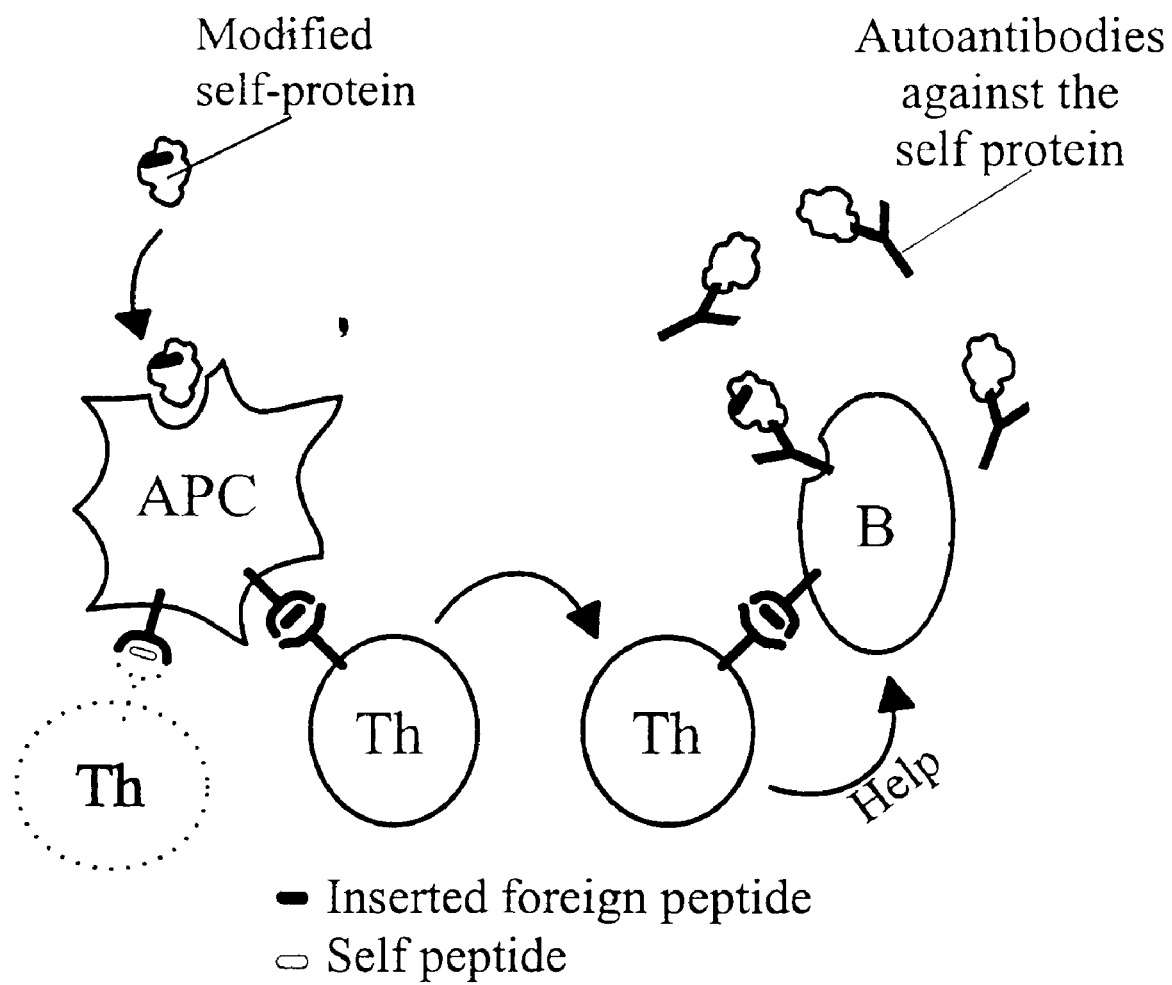

Jacoby, David R. et al.; "Immunologic . . " Advances in Immunology, vol. 35, pp. 157-208, 1984.

Hopp, Thomas P. et al.; "A Computer . . " Molecular Immunology vol. 20, No. 4 pp. 483-489 (1983).

Dalum, Iben et al., "Induction of cross-reactive antibodies against a self protein by immunizing with a modified self protein containing a foreign T helper Epitope," Molecular Immunology, 1997, vol. 34, No. 16-17, pp. 1113-1120.

Janeway, Immuno Biology 3rd Edition, Garland Publishing Inc, 1997, page 21.

Leach, Dana, "Vaccination with Modified HRR-2 Molecules . . . , " 11th International Congress of Immunology, Theme 3 pg. 74.

Steinaa, Lucilla, "Cognate T-Cell help breaks Cytotoxic T Lymphocyte (CTL) Tolerance Against Self-Antigens," 11th International Congress of Immunology, Theme 3, pg. 73.

Widmann, C., et al., "T helper epitopes enhance the cytotoxic," Journal of Immunological Methods, 155 (1992), pp. 95-99.

Alexander, J. et al., "The optimization of helper t lymphocyte$_{13}$,"Immunologic Research 1998: 18/2. pp. 79-92.

Stoute, J. et al., "A preliminary evaluation of a recombinant$_{13}$," The New England Journal of Medicine, 1997, vol. 336 (2), pp. 86-91.

Hanke, T et al., "DNA multi-CTL epitope vaccine$_{13}$, " Vaccine, 1998, vol. 16, No. 4, pp. 426-435.

Gilbert, S. et al., A protein particle vaccine containing multiple$_{13}$, Nature Biotechnology, Nov. 1997, vol. 15, pp. 1280.

Yang, Kiao-Dong et al., "Eradication of . . . "Cancer Research 59 1236-1243, Apr. 15, 1999.

Kass, Erik et al., "Induction of . . " Cancer Research 59, 676-679 Jun. 1999.

Vonderheide, Robert H. et al., The Tolerance . . . Immunity Vol. 10, 673-679 Jun. 1999.

Kikuchi, Megumi et al., "Identification of a . . "Int. J. Cancer: 81: 459-466 1999.

Marchand, Marie et al.; "Tumor Regressions . . "Int. J. Cancer: 80: 219-230 1999.

Sandmaier, Brenda et al., "Evidence of . . " Journal of Immunotherapy 22(1): 54-66.

Graft tolerance., "Nature Medicine vol. 5, Jun. 1999.

Wang, Rong-Fu et al.; "Cloning Genes . ." Science vol. 284, May 21, 1999.

Sanda, Martin G. et al., "Recombinant Vaccina . . " Urology 53 (2) 1999.

Kirkin, Alexei F. et al., "Melanoma-associated . . " Armis 106: 663-679, 1993.

Klote, Theo et al., "Selective Expression

Divigi, Chaitanya R. et al., "Phase I/II . . . "Clinical Cancer Research vol. 4, 2729-2739 Nov. 1998.

Ossendorf, Ferry et al.; "Specific T Helper . . . "J. Exp. Med. vol. 187, No. 5, 3-2-1998 pp. 693-702.

Jager, Elke wt al., "Simultaneous Humoral., "J. Exp. Med. vol. 187, No. 2, Jan. 199, 1998, pp. 265-270.

Southwood, Scott et al., "Several Common . . . "Journal of Immunology pp. 3363-3373.

Schoenberger, Stephen et al., "T-cell help," Nature vol. 393, Jun. 4, 1998.

Bennett, Sally R.M. et al.;"Help for.."Nature vol. 393, Jun. 4, 1998.

Lanzavecchia, Antonio, "License to Kill " Nature vol. 393, Jun. 4, 1998.

Wagner, Stephen N. et al, "Expression and function . . . "Int. J. Cancer: 71. 1049-1055 1997.

Jarvis, Gary A. et al, "Expression and function . . . "Int. J. Cancer: 71 1049-1055 1997.

Knox, Susan J., et al., " Ye exium-90-labeled . . "Clinical Cancer Research vol. 2, pp. 457-470 Mrch 1996.

Ghosh, Ananta K, et al; "Molecular Cloning . . . "Cell Growth vol. 7, 1425-1434 Oct. 1996.

Rock, Kenneth L. et al.; "Analysis of the . . . "Ame. Assoc. Immunology 3721-3726.

Murphy, G.P. et al., "Measurement of . . . "the Prostate 25: 266-271 (1996).

Abrams, Scott Y. et al.; "Mutant ras . . . "Seminars in Oncology vol. 23, No. 1 (February) 1996: pp. 118-134.

Wright, George L. et al., "Upregulation of . . . "Urology 48 (2) 1996.

Rock, Edwin P. et al., "Immunology of a . . . "Vaccine 1996 vol. 14, No. 16.

Murphy, gerald et al., "Comparison of . . . "Anticancer Research 15: 1473-1480 (1995).

Ohnishi, Y et al., "Prolonged survival . . . "British J. of Cancer (1995) 71, 969-973.

Wiener, Louis M., et al.; "Phase I Trial., "Cancer Research 55, 4586-4593, Oct. 15, 1995.

Macarthur, Craig A. et al., "FGRF-8 Isoforms . . "Cell Growth vol. 6, 817-825 Jul. 1995.

Salomon, David S. et al., "Epidermal growth. . " Critical reviews in Oncology/Hematology 19 (1995) 183-232.

Crossley, Phillip H. et al., "The mouse Fgf8 . . "Development 121, 439-451 (1995).

Rammensee, Hans-Georg et al., "MMC ligands . . " Immunogentics (1995) 41: 178-226.

Zhu, Zhenping et al., "Engineering high . . "Int. J. Cancer: 62, 319-324 (1995).

Tjoa, Benhamin et al., "In Vittro . . "The Prostate 27: 63-69 (1995).

"OLFEL, Thomas et al., "A p16ink4a . . Science vol. 269, Sep. 1, 1995.

Lewis, Jonathon J. et al.; "Definition of J. " Cancer Biology, vol. 6, 1995: pp. 321-327.

Lupu, Ruth et al., "Interaction between . . "Cancer Biology, vol. 6, 1995: pp. 135-145.

Kalk, Kirsten et al.; "Pool sequencing of . . " Immunogenetics 39: 230-242, 1994.

Kahn, Daniel et al., "Radioimmunoscintigraphy . . "Journal of Urology vol. 152, 1490-1495 Nov. 1994.

Lapthorn, A.J. et al., "Crystal structure", Nature, 1994.

Talwar, G.P. et al.; "A vaccine . . "Proc. Natl. Acad. Sci. vol. 91, pp. 8532-8536 Aug. 1994.

Horadi, Mark M. et al., "Serum and . . "Cancer Oct. 13, 1993 vol. 72, No. 8.

Grondahal-Hansen, Jan et al., "High levels," Cancer Research 54, 2513-2521, Jun. 1, 1993.

Israeli, Ron S., et al., "Molecular clonings . . "Cancer Research 33, 227-230, Jan. 13, 1993.

Hammer, Juergen et al.; "Promiscuous and . . " Cell, vol. 74, 197-203 Jul. 16, 1993.

Tanaka, Akira et al.; "Cloning and . . "Proc. Natl. Acad. Sci. vol. 89, pp. 8928-8932, Oct. 1992.

Sinigaglia, et al.; "A malaria T-cell . ." Nature vol. 336, 22/29 Dec. 1998.

* cited by examiner

```
                FGF8e and -f                           FGF8b and -f
MGSPRSALSC LLLHLLVLCL QAQEGPGRGP ALGRELASLF RAGREPQGVS QQVTVQSSPÑ   31
FTQHVREQSL VTDQLSRRLI RTYQLYSRTS GKHVQVLANK RINAMAEDGD PFAKLIVETD   91
TFGSRVRVRG AETGLYICMN KKGKLIAKSN GKGKDCVFTE IVLENNYTAL QNAKYEGWYM  151
AFTRKGRPRK GSKTRQHQRE VHFMKRLPRG HHTTEQSLRF EFLNYPPFTR SLRGSQRTWA  211
PEPR                                                              215
```

```
WT    MGSPRSALSCLLLHLLVLCLQAQVTVQSSPNFTQHVREQSLVTDQLSRRLIRTYQLYSRTSGKHVQ     66
F30N              MAQVTVFNNFTVSFWLRVPKVSASHLERRLIRTYQLYSRTSGKHVQ              46
F2I               MAQVTVQSSPNFTQHVREQSLVTDQLSRRLIRTYQLYSRTSGKHVQ              46
F30I              MAQVTVQSSPNFTQHVREQSLVTDQLSRRLIRTYQLYSRTSGKHVQ              46
F2C               MAQVTVQSSPNFTQHVREQSLVTDQLSRRLIRTYQLYSRTSGKHVQ              46

WT    VLANKRINAMAEDGDPFAKLIVETDTF            GSRVRVGAETGLYICMNKKGKLIAK      119
F30N  VLANKRINAMAEDGDPFAKLIVETDTF            GSRVRVGAETGLYICMNKKGKLIAK       99
F2I   VLANKRINAMAEDGDPFAKLIVETDQYIKANSKFIGITELGSRVRVGAETGLYICMNKKGKLIAK     112
F30I  VLANKRINAMAEDGDPFAKLIVETDTF            GSRVRVGAETGLYICMNKKGKLIAK       99
F2C   VLANKRINAMAEDGDPFAKLIVETDTF            GSRVRVGAETGLYICMNKKGKLIAK       99

WT    SNG            KGKDCVFTEIGLENNYTALCNAKYEGWYMAFTRKGRPRKGSKTRQ          167
F30N  SNG            KGKDCVFTEIGLENNYTALCNAKYEGWYMAFTRKGRPRKGSKTRQ          147
F2I   SNG            KGKDCVFTEIGLENNYTALCNAKYEGWYMAFTRKGRPRKGSKTRQ          160
F30I  SNGFNNFTVSFWLRVPKVSASHLEDCVFTEIGLENNYTALCNAKYEGWYMAFTRKGRPRKGSKTRQ    165
F2C   SNG            KGKDCVFTEIGLENNYTALCNAKYEGWYMAFTRKGRPRKGSKTRQ          147

WT    HQREVHFMFPLPPGHHTTEQSLPFEFLNYPPFT         RSLRGSQRTWA    PEPR     215
F30N  HQREVHFMFPLPPGHHTTEQSLPFEFLNYPPFT         RSLRGSQRTWA    PEPP     195
F2I   HQREVHFMFPLPPGHHTTEQSLPFEFLNYPPFT         RSLRGSQRTWA    PEPP     208
F30I  HQREVHFMFPLPPGHHTTEQSLPFEFLNYPPFT         RSLRGSQRTWA    PEPP     213
F2C   HQREVHFMFPLPPGHHTTEQSLPFEFLNYPPFTQYIKANSKFIGITELPEPR              199
```

Fig. 6

SEQUENCE LISTING

```
<160> NUMBER OF SEQ ID NOS: 41

<210> SEQ ID NO 1
<211> LENGTH: 2253
<212> TYPE: DNA
<213> ORGANISM: Homo sapiens
<220> FEATURE:
<221> NAME/KEY: CDS
<222> LOCATION: (1)..(2253)
<223> OTHER INFORMATION:
```

-continued

```
<221> NAME/KEY: misc
<222> LOCATION: (58)..(2253)
<223> OTHER INFORMATION: Human PSM'

<400> SEQUENCE: 1 atg kgk aat ctc ctt cac gaa acc gac tcg gct gtg gcc acc gcg cgc      48
Met Xaa Asn Leu Leu His Glu Thr Asp Ser Ala Val Ala Thr Ala Arg
1               5                   10                  15 cgc ccg cgc tgg ctg tgc gct ggg gcg ctg gtg ctg gcg ggt ggc ttc      96
Arg Pro Arg Trp Leu Cys Ala Gly Ala Leu Val Leu Ala Gly Gly Phe
            20                  25                  30 ttt ctc ctc ggc ttc ctc ttc ggg tgg ttt ata aaa tcc tcc aat gaa     144
Phe Leu Leu Gly Phe Leu Phe Gly Trp Phe Ile Lys Ser Ser Asn Glu
        35                  40                  45 gct act aac att act cca aag cat aat atg aaa gca ttt ttg gat gaa     192
Ala Thr Asn Ile Thr Pro Lys His Asn Met Lys Ala Phe Leu Asp Glu
    50                  55                  60 ttg aaa gct gag aac atc aag aag ttc tta tat aat ttt aca cag ata     240
Leu Lys Ala Glu Asn Ile Lys Lys Phe Leu Tyr Asn Phe Thr Gln Ile
65                  70                  75                  80 cca cat tta gca gga aca gaa caa aac ttt cag ctt gca aag caa att     288
Pro His Leu Ala Gly Thr Glu Gln Asn Phe Gln Leu Ala Lys Gln Ile
                85                  90                  95 caa tcc cag tgg aaa gaa ttt ggc ctg gat tct gtt gag cta gca cat     336
Gln Ser Gln Trp Lys Glu Phe Gly Leu Asp Ser Val Glu Leu Ala His
            100                 105                 110 tat gat gtc ctg ttg tcc tac cca aat aag act cat ccc aac tac atc     384
Tyr Asp Val Leu Leu Ser Tyr Pro Asn Lys Thr His Pro Asn Tyr Ile
        115                 120                 125 tca ata att aat gaa gat gga aat gag att ttc aac aca tca tta ttt     432
Ser Ile Ile Asn Glu Asp Gly Asn Glu Ile Phe Asn Thr Ser Leu Phe
    130                 135                 140 gaa cca cct cct cca gga tat gaa aat gtt tcg gat att gta cca cct     480
Glu Pro Pro Pro Pro Gly Tyr Glu Asn Val Ser Asp Ile Val Pro Pro
145                 150                 155                 160 ttc agt gct ttc tct cct caa gga atg cca gag ggc gat cta gtg tat     528
Phe Ser Ala Phe Ser Pro Gln Gly Met Pro Glu Gly Asp Leu Val Tyr
                165                 170                 175 gtt aac tat gca cga act gaa gac ttc ttt aaa ttg gaa cgg gac atg     576
Val Asn Tyr Ala Arg Thr Glu Asp Phe Phe Lys Leu Glu Arg Asp Met
            180                 185                 190 aaa atc aat tgc tct ggg aaa att gta att gcc aga tat ggg aaa gtt     624
Lys Ile Asn Cys Ser Gly Lys Ile Val Ile Ala Arg Tyr Gly Lys Val
        195                 200                 205 ttc aga gga aat aag gtt aaa aat gcc cag ctg gca ggg gcc aaa gga     672
Phe Arg Gly Asn Lys Val Lys Asn Ala Gln Leu Ala Gly Ala Lys Gly
    210                 215                 220 gtc att ctc tac tcc gac cct gct gac tac ttt gct cct ggg gtg aag     720
Val Ile Leu Tyr Ser Asp Pro Ala Asp Tyr Phe Ala Pro Gly Val Lys
225                 230                 235                 240 tcc tat cca gat ggt tgg aat ctt cct gga ggt ggt gtc cag cgt gga     768
Ser Tyr Pro Asp Gly Trp Asn Leu Pro Gly Gly Gly Val Gln Arg Gly
                245                 250                 255 aat atc cta aat ctg aat ggt gca gga gac cct ctc aca cca ggt tac     816
Asn Ile Leu Asn Leu Asn Gly Ala Gly Asp Pro Leu Thr Pro Gly Tyr
            260                 265                 270 cca gca aat gaa tat gct tat agg cgt gga att gca gag gct gtt ggt     864
Pro Ala Asn Glu Tyr Ala Tyr Arg Arg Gly Ile Ala Glu Ala Val Gly
        275                 280                 285
```

-continued

| | | |
|---|---|---|
| ctt cca agt att cct gtt cat cca att gga tac tat gat gca cag aag<br>Leu Pro Ser Ile Pro Val His Pro Ile Gly Tyr Tyr Asp Ala Gln Lys<br>290                        295                        300 | 912 |
| ctc cta gaa aaa atg ggt ggc tca gca cca cca gat agc agc tgg aga<br>Leu Leu Glu Lys Met Gly Gly Ser Ala Pro Pro Asp Ser Ser Trp Arg<br>305                        310                        315                        320 | 960 |
| gga agt ctc aaa gtg ccc tac aat gtt gga cct ggc ttt act gga aac<br>Gly Ser Leu Lys Val Pro Tyr Asn Val Gly Pro Gly Phe Thr Gly Asn<br>                        325                        330                        335 | 1008 |
| ttt tct aca caa aaa gtc aag atg cac atc cac tct acc aat gaa gtg<br>Phe Ser Thr Gln Lys Val Lys Met His Ile His Ser Thr Asn Glu Val<br>                    340                        345                        350 | 1056 |
| aca aga att tac aat gtg ata ggt act ctc aga gga gca gtg gaa cca<br>Thr Arg Ile Tyr Asn Val Ile Gly Thr Leu Arg Gly Ala Val Glu Pro<br>355                        360                        365 | 1104 |
| gac aga tat gtc att ctg gga ggt cac cgg gac tca tgg gtg ttt ggt<br>Asp Arg Tyr Val Ile Leu Gly Gly His Arg Asp Ser Trp Val Phe Gly<br>370                        375                        380 | 1152 |
| ggt att gac cct cag agt gga gca gct gtt gtt cat gaa att gtg agg<br>Gly Ile Asp Pro Gln Ser Gly Ala Ala Val Val His Glu Ile Val Arg<br>385                        390                        395                        400 | 1200 |
| agc ttt gga aca ctg aaa aag gaa ggg tgg aga cct aga aga aca att<br>Ser Phe Gly Thr Leu Lys Lys Glu Gly Trp Arg Pro Arg Arg Thr Ile<br>                    405                        410                        415 | 1248 |
| ttg ttt gca agc tgg gat gca gaa gaa ttt ggt ctt ctt ggt tct act<br>Leu Phe Ala Ser Trp Asp Ala Glu Glu Phe Gly Leu Leu Gly Ser Thr<br>                    420                        425                        430 | 1296 |
| gag tgg gca gag gag aat tca aga ctc ctt caa gag cgt ggc gtg gct<br>Glu Trp Ala Glu Glu Asn Ser Arg Leu Leu Gln Glu Arg Gly Val Ala<br>                  435                        440                        445 | 1344 |
| tat att aat gct gac tca tct ata gaa gga aac tac act ctg aga gtt<br>Tyr Ile Asn Ala Asp Ser Ser Ile Glu Gly Asn Tyr Thr Leu Arg Val<br>450                        455                        460 | 1392 |
| gat tgt aca ccg ctg atg tac agc ttg gta cac aac cta aca aaa gag<br>Asp Cys Thr Pro Leu Met Tyr Ser Leu Val His Asn Leu Thr Lys Glu<br>465                        470                        475                        480 | 1440 |
| ctg aaa agc cct gat gaa ggc ttt gaa ggc aaa tct ctt tat gaa agt<br>Leu Lys Ser Pro Asp Glu Gly Phe Glu Gly Lys Ser Leu Tyr Glu Ser<br>                    485                        490                        495 | 1488 |
| tgg act aaa aaa agt cct tcc cca gag ttc agt ggc atg ccc agg ata<br>Trp Thr Lys Lys Ser Pro Ser Pro Glu Phe Ser Gly Met Pro Arg Ile<br>                  500                        505                        510 | 1536 |
| agc aaa ttg gga tct gga aat gat ttt gag gtg ttc ttc caa cga ctt<br>Ser Lys Leu Gly Ser Gly Asn Asp Phe Glu Val Phe Phe Gln Arg Leu<br>515                        520                        525 | 1584 |
| gga att gct tca ggc aga gca cgg tat act aaa aat tgg gaa aca aac<br>Gly Ile Ala Ser Gly Arg Ala Arg Tyr Thr Lys Asn Trp Glu Thr Asn<br>530                        535                        540 | 1632 |
| aaa ttc agc ggc tat cca ctg tat cac agt gtc tat gaa aca tat gag<br>Lys Phe Ser Gly Tyr Pro Leu Tyr His Ser Val Tyr Glu Thr Tyr Glu<br>545                        550                        555                        560 | 1680 |
| ttg gtg gaa aag ttt tat gat cca atg ttt aaa tat cac ctc act gtg<br>Leu Val Glu Lys Phe Tyr Asp Pro Met Phe Lys Tyr His Leu Thr Val<br>                    565                        570                        575 | 1728 |
| gcc cag gtt cga gga ggg atg gtg ttt gag cta gcc aat tcc ata gtg<br>Ala Gln Val Arg Gly Gly Met Val Phe Glu Leu Ala Asn Ser Ile Val<br>                  580                        585                        590 | 1776 |
| ctc cct ttt gat tgt cga gat tat gct gta gtt tta aga aag tat gct<br>Leu Pro Phe Asp Cys Arg Asp Tyr Ala Val Val Leu Arg Lys Tyr Ala<br>                  595                        600                        605 | 1824 |

```
gac aaa atc tac agt att tct atg aaa cat cca cag gaa atg aag aca    1872
Asp Lys Ile Tyr Ser Ile Ser Met Lys His Pro Gln Glu Met Lys Thr
    610                 615                 620 tac agt gta tca ttt gat tca ctt ttt tct gca gta aag aat ttt aca    1920
Tyr Ser Val Ser Phe Asp Ser Leu Phe Ser Ala Val Lys Asn Phe Thr
625                 630                 635                 640 gaa att gct tcc aag ttc agt gag aga ctc cag gac ttt gac aaa agc    1968
Glu Ile Ala Ser Lys Phe Ser Glu Arg Leu Gln Asp Phe Asp Lys Ser
                645                 650                 655 aac cca ata gta tta aga atg atg aat gat caa ctc atg ttt ctg gaa    2016
Asn Pro Ile Val Leu Arg Met Met Asn Asp Gln Leu Met Phe Leu Glu
            660                 665                 670 aga gca ttt att gat cca tta ggg tta cca gac agg cct ttt tat agg    2064
Arg Ala Phe Ile Asp Pro Leu Gly Leu Pro Asp Arg Pro Phe Tyr Arg
        675                 680                 685 cat gtc atc tat gct cca agc agc cac aac aag tat gca ggg gag tca    2112
His Val Ile Tyr Ala Pro Ser Ser His Asn Lys Tyr Ala Gly Glu Ser
    690                 695                 700 ttc cca gga att tat gat gct ctg ttt gat att gaa agc aaa gtg gac    2160
Phe Pro Gly Ile Tyr Asp Ala Leu Phe Asp Ile Glu Ser Lys Val Asp
705                 710                 715                 720 cct tcc aag gcc tgg gga gaa gtg aag aga cag att tat gtt gca gcc    2208
Pro Ser Lys Ala Trp Gly Glu Val Lys Arg Gln Ile Tyr Val Ala Ala
                725                 730                 735 ttc aca gtg cag gca gct gca gag act ttg agt gaa gta gcc taa        2253
Phe Thr Val Gln Ala Ala Ala Glu Thr Leu Ser Glu Val Ala
            740                 745                 750

<210> SEQ ID NO 2
<211> LENGTH: 750
<212> TYPE: PRT
<213> ORGANISM: Homo sapiens
<220> FEATURE:
<221> NAME/KEY: misc_feature
<222> LOCATION: (2)..(2)
<223> OTHER INFORMATION: The 'Xaa' at location 2 stands for Gly or Trp.

<400> SEQUENCE: 2

Met Xaa Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Pro Gly Tyr Glu Asn Val Ser Asp Ile Val Pro Pro
145                 150                 155                 160
```

-continued

```
Phe Ser Ala Phe Ser Pro Gln Gly Met Pro Glu Gly Asp Leu Val Tyr
            165                 170                 175

Val Asn Tyr Ala Arg Thr Glu Asp Phe Lys Leu Glu Arg Asp Met
        180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
    370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
    450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
    530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575
```

```
Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
            595                 600                 605

Asp Lys Ile Tyr Ser Ile Ser Met Lys His Pro Gln Glu Met Lys Thr
610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr Ala Gly Glu Ser
            690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
            740                 745                 750

<210> SEQ ID NO 3
<211> LENGTH: 3768
<212> TYPE: DNA
<213> ORGANISM: Homo sapiens
<220> FEATURE:
<221> NAME/KEY: CDS
<222> LOCATION: (1)..(3768)

<400> SEQUENCE: 3 atg gag ctg gcg gcc ttg tgc cgc tgg ggg ctc ctc ctc gcc ctc ttg      48
Met Glu Leu Ala Ala Leu Cys Arg Trp Gly Leu Leu Leu Ala Leu Leu
            -20                 -15                 -10 ccc ccc gga gcc gcg agc acc caa gtg tgc acc ggc aca gac atg aag      96
Pro Pro Gly Ala Ala Ser Thr Gln Val Cys Thr Gly Thr Asp Met Lys
        -5                  -1   1               5 ctg cgg ctc cct gcc agt ccc gag acc cac ctg gac atg ctc cgc cac     144
Leu Arg Leu Pro Ala Ser Pro Glu Thr His Leu Asp Met Leu Arg His
 10                  15                  20                  25 ctc tac cag ggc tgc cag gtg gtg cag gga aac ctg gaa ctc acc tac     192
Leu Tyr Gln Gly Cys Gln Val Val Gln Gly Asn Leu Glu Leu Thr Tyr
                 30                  35                  40 ctg ccc acc aat gcc agc ctg tcc ttc ctg cag gat atc cag gag gtg     240
Leu Pro Thr Asn Ala Ser Leu Ser Phe Leu Gln Asp Ile Gln Glu Val
             45                  50                  55 cag ggc tac gtg ctc atc gct cac aac caa gtg agg cag gtc cca ctg     288
Gln Gly Tyr Val Leu Ile Ala His Asn Gln Val Arg Gln Val Pro Leu
             60                  65                  70 cag agg ctg cgg att gtg cga ggc acc cag ctc ttt gag gac aac tat     336
Gln Arg Leu Arg Ile Val Arg Gly Thr Gln Leu Phe Glu Asp Asn Tyr
 75                  80                  85 gcc ctg gcc gtg cta gac aat gga gac ccg ctg aac aat acc acc cct     384
Ala Leu Ala Val Leu Asp Asn Gly Asp Pro Leu Asn Asn Thr Thr Pro
 90                  95                  100                 105 gtc aca ggg gcc tcc cca gga ggc ctg cgg gag ctg cag ctt cga agc     432
Val Thr Gly Ala Ser Pro Gly Gly Leu Arg Glu Leu Gln Leu Arg Ser
             110                 115                 120
```

-continued

| | | |
|---|---|---|
| ctc aca gag atc ttg aaa gga ggg gtc ttg atc cag cgg aac ccc cag<br>Leu Thr Glu Ile Leu Lys Gly Gly Val Leu Ile Gln Arg Asn Pro Gln<br>        125                    130                  135 | 480 |
| ctc tgc tac cag gac acg att ttg tgg aag gac atc ttc cac aag aac<br>Leu Cys Tyr Gln Asp Thr Ile Leu Trp Lys Asp Ile Phe His Lys Asn<br>        140                    145                  150 | 528 |
| aac cag ctg gct ctc aca ctg ata gac acc aac cgc tct cgg gcc tgc<br>Asn Gln Leu Ala Leu Thr Leu Ile Asp Thr Asn Arg Ser Arg Ala Cys<br>        155                    160                  165 | 576 |
| cac ccc tgt tct ccg atg tgt aag ggc tcc cgc tgc tgg gga gag agt<br>His Pro Cys Ser Pro Met Cys Lys Gly Ser Arg Cys Trp Gly Glu Ser<br>170                    175                  180                  185 | 624 |
| tct gag gat tgt cag agc ctg acg cgc act gtc tgt gcc ggt ggc tgt<br>Ser Glu Asp Cys Gln Ser Leu Thr Arg Thr Val Cys Ala Gly Gly Cys<br>                190                  195                  200 | 672 |
| gcc cgc tgc aag ggg cca ctg ccc act gac tgc tgc cat gag cag tgt<br>Ala Arg Cys Lys Gly Pro Leu Pro Thr Asp Cys Cys His Glu Gln Cys<br>        205                    210                  215 | 720 |
| gct gcc ggc tgc acg ggc ccc aag cac tct gac tgc ctg gcc tgc ctc<br>Ala Ala Gly Cys Thr Gly Pro Lys His Ser Asp Cys Leu Ala Cys Leu<br>        220                    225                  230 | 768 |
| cac ttc aac cac agt ggc atc tgt gag ctg cac tgc cca gcc ctg gtc<br>His Phe Asn His Ser Gly Ile Cys Glu Leu His Cys Pro Ala Leu Val<br>        235                    240                  245 | 816 |
| acc tac aac aca gac acg ttt gag tcc atg ccc aat ccc gag ggc cgg<br>Thr Tyr Asn Thr Asp Thr Phe Glu Ser Met Pro Asn Pro Glu Gly Arg<br>250                    255                  260                  265 | 864 |
| tat aca ttc ggc gcc agc tgt gtg act gcc tgt ccc tac aac tac ctt<br>Tyr Thr Phe Gly Ala Ser Cys Val Thr Ala Cys Pro Tyr Asn Tyr Leu<br>                270                  275                  280 | 912 |
| tct acg gac gtg gga tcc tgc acc ctc gtc tgc ccc ctg cac aac caa<br>Ser Thr Asp Val Gly Ser Cys Thr Leu Val Cys Pro Leu His Asn Gln<br>                285                  290                  295 | 960 |
| gag gtg aca gca gag gat gga aca cag cgg tgt gag aag tgc agc aag<br>Glu Val Thr Ala Glu Asp Gly Thr Gln Arg Cys Glu Lys Cys Ser Lys<br>                300                  305                  310 | 1008 |
| ccc tgt gcc cga gtg tgc tat ggt ctg ggc atg gag cac ttg cga gag<br>Pro Cys Ala Arg Val Cys Tyr Gly Leu Gly Met Glu His Leu Arg Glu<br>        315                    320                  325 | 1056 |
| gtg agg gca gtt acc agt gcc aat atc cag gag ttt gct ggc tgc aag<br>Val Arg Ala Val Thr Ser Ala Asn Ile Gln Glu Phe Ala Gly Cys Lys<br>330                    335                  340                  345 | 1104 |
| aag atc ttt ggg agc ctg gca ttt ctg ccg gag agc ttt gat ggg gac<br>Lys Ile Phe Gly Ser Leu Ala Phe Leu Pro Glu Ser Phe Asp Gly Asp<br>                350                  355                  360 | 1152 |
| cca gcc tcc aac act gcc ccg ctc cag cca gag cag ctc caa gtg ttt<br>Pro Ala Ser Asn Thr Ala Pro Leu Gln Pro Glu Gln Leu Gln Val Phe<br>        365                    370                  375 | 1200 |
| gag act ctg gaa gag atc aca ggt tac cta tac atc tca gca tgg ccg<br>Glu Thr Leu Glu Glu Ile Thr Gly Tyr Leu Tyr Ile Ser Ala Trp Pro<br>                380                  385                  390 | 1248 |
| gac agc ctg cct gac ctc agc gtc ttc cag aac ctg caa gta atc cgg<br>Asp Ser Leu Pro Asp Leu Ser Val Phe Gln Asn Leu Gln Val Ile Arg<br>        395                    400                  405 | 1296 |
| gga cga att ctg cac aat ggc gcc tac tcg ctg acc ctg caa ggg ctg<br>Gly Arg Ile Leu His Asn Gly Ala Tyr Ser Leu Thr Leu Gln Gly Leu<br>410                    415                  420                  425 | 1344 |
| ggc atc agc tgg ctg ggg ctg cgc tca ctg agg gaa ctg ggc agt gga<br>Gly Ile Ser Trp Leu Gly Leu Arg Ser Leu Arg Glu Leu Gly Ser Gly<br>                430                  435                  440 | 1392 |

```
ctg gcc ctc atc cac cat aac acc cac ctc tgc ttc gtg cac acg gtg      1440
Leu Ala Leu Ile His His Asn Thr His Leu Cys Phe Val His Thr Val
            445                 450                 455 ccc tgg gac cag ctc ttt cgg aac ccg cac caa gct ctg ctc cac act      1488
Pro Trp Asp Gln Leu Phe Arg Asn Pro His Gln Ala Leu Leu His Thr
        460                 465                 470 gcc aac cgg cca gag gac gag tgt gtg ggc gag ggc ctg gcc tgc cac      1536
Ala Asn Arg Pro Glu Asp Glu Cys Val Gly Glu Gly Leu Ala Cys His
475                 480                 485 cag ctg tgc gcc cga ggg cac tgc tgg ggt cca ggg ccc acc cag tgt      1584
Gln Leu Cys Ala Arg Gly His Cys Trp Gly Pro Gly Pro Thr Gln Cys
490                 495                 500                 505 gtc aac tgc agc cag ttc ctt cgg ggc cag gag tgt gtg gag gaa tgc      1632
Val Asn Cys Ser Gln Phe Leu Arg Gly Gln Glu Cys Val Glu Glu Cys
                510                 515                 520 cga gta ctg cag ggg ctc ccc agg gag tat gtg aat gcc agg cac tgt      1680
Arg Val Leu Gln Gly Leu Pro Arg Glu Tyr Val Asn Ala Arg His Cys
            525                 530                 535 ttg ccg tgc cac cct gag tgt cag ccc cag aat ggc tca gtg acc tgt      1728
Leu Pro Cys His Pro Glu Cys Gln Pro Gln Asn Gly Ser Val Thr Cys
        540                 545                 550 ttt gga ccg gag gct gac cag tgt gtg gcc tgt gcc cac tat aag gac      1776
Phe Gly Pro Glu Ala Asp Gln Cys Val Ala Cys Ala His Tyr Lys Asp
555                 560                 565 cct ccc ttc tgc gtg gcc cgc tgc ccc agc ggt gtg aaa cct gac ctc      1824
Pro Pro Phe Cys Val Ala Arg Cys Pro Ser Gly Val Lys Pro Asp Leu
570                 575                 580                 585 tcc tac atg ccc atc tgg aag ttt cca gat gag gag ggc gca tgc cag      1872
Ser Tyr Met Pro Ile Trp Lys Phe Pro Asp Glu Glu Gly Ala Cys Gln
                590                 595                 600 cct tgc ccc atc aac tgc acc cac tcc tgt gtg gac ctg gat gac aag      1920
Pro Cys Pro Ile Asn Cys Thr His Ser Cys Val Asp Leu Asp Asp Lys
            605                 610                 615 ggc tgc ccc gcc gag cag aga gcc agc cct ctg acg tcc atc gtc tct      1968
Gly Cys Pro Ala Glu Gln Arg Ala Ser Pro Leu Thr Ser Ile Val Ser
        620                 625                 630 gcg gtg gtt ggc att ctg ctg gtc gtg gtc ttg ggg gtg gtc ttt ggg      2016
Ala Val Val Gly Ile Leu Leu Val Val Val Leu Gly Val Val Phe Gly
635                 640                 645 atc ctc atc aag cga cgg cag cag aag atc cgg aag tac acg atg cgg      2064
Ile Leu Ile Lys Arg Arg Gln Gln Lys Ile Arg Lys Tyr Thr Met Arg
650                 655                 660                 665 aga ctg ctg cag gaa acg gag ctg gtg gag ccg ctg aca cct agc gga      2112
Arg Leu Leu Gln Glu Thr Glu Leu Val Glu Pro Leu Thr Pro Ser Gly
                670                 675                 680 gcg atg ccc aac cag gcg cag atg cgg atc ctg aaa gag acg gag ctg      2160
Ala Met Pro Asn Gln Ala Gln Met Arg Ile Leu Lys Glu Thr Glu Leu
            685                 690                 695 agg aag gtg aag gtg ctt gga tct ggc gct ttt ggc aca gtc tac aag      2208
Arg Lys Val Lys Val Leu Gly Ser Gly Ala Phe Gly Thr Val Tyr Lys
        700                 705                 710 ggc atc tgg atc cct gat ggg gag aat gtg aaa att cca gtg gcc atc      2256
Gly Ile Trp Ile Pro Asp Gly Glu Asn Val Lys Ile Pro Val Ala Ile
715                 720                 725 aaa gtg ttg agg gaa aac aca tcc ccc aaa gcc aac aaa gaa atc tta      2304
Lys Val Leu Arg Glu Asn Thr Ser Pro Lys Ala Asn Lys Glu Ile Leu
730                 735                 740                 745 gac gaa gca tac gtg atg gct ggt gtg ggc tcc cca tat gtc tcc cgc      2352
Asp Glu Ala Tyr Val Met Ala Gly Val Gly Ser Pro Tyr Val Ser Arg
                750                 755                 760
```

```
ctt ctg ggc atc tgc ctg aca tcc acg gtg cag ctg gtg aca cag ctt        2400
Leu Leu Gly Ile Cys Leu Thr Ser Thr Val Gln Leu Val Thr Gln Leu
            765                 770                 775 atg ccc tat ggc tgc ctc tta gac cat gtc cgg gaa aac cgc gga cgc        2448
Met Pro Tyr Gly Cys Leu Leu Asp His Val Arg Glu Asn Arg Gly Arg
        780                 785                 790 ctg ggc tcc cag gac ctg ctg aac tgg tgt atg cag att gcc aag ggg        2496
Leu Gly Ser Gln Asp Leu Leu Asn Trp Cys Met Gln Ile Ala Lys Gly
    795                 800                 805 atg agc tac ctg gag gat gtg cgg ctc gta cac agg gac ttg gcc gct        2544
Met Ser Tyr Leu Glu Asp Val Arg Leu Val His Arg Asp Leu Ala Ala
810                 815                 820                 825 cgg aac gtg ctg gtc aag agt ccc aac cat gtc aaa att aca gac ttc        2592
Arg Asn Val Leu Val Lys Ser Pro Asn His Val Lys Ile Thr Asp Phe
                830                 835                 840 ggg ctg gct cgg ctg ctg gac att gac gag aca gag tac cat gca gat        2640
Gly Leu Ala Arg Leu Leu Asp Ile Asp Glu Thr Glu Tyr His Ala Asp
            845                 850                 855 ggg ggc aag gtg ccc atc aag tgg atg gcg ctg gag tcc att ctc cgc        2688
Gly Gly Lys Val Pro Ile Lys Trp Met Ala Leu Glu Ser Ile Leu Arg
        860                 865                 870 cgg cgg ttc acc cac cag agt gat gtg tgg agt tat ggt gtg act gtg        2736
Arg Arg Phe Thr His Gln Ser Asp Val Trp Ser Tyr Gly Val Thr Val
    875                 880                 885 tgg gag ctg atg act ttt ggg gcc aaa cct tac gat ggg atc cca gcc        2784
Trp Glu Leu Met Thr Phe Gly Ala Lys Pro Tyr Asp Gly Ile Pro Ala
890                 895                 900                 905 cgg gag atc cct gac ctg ctg gaa aag ggg gag cgg ctg ccc cag ccc        2832
Arg Glu Ile Pro Asp Leu Leu Glu Lys Gly Glu Arg Leu Pro Gln Pro
                910                 915                 920 ccc atc tgc acc att gat gtc tac atg atc atg gtc aaa tgt tgg atg        2880
Pro Ile Cys Thr Ile Asp Val Tyr Met Ile Met Val Lys Cys Trp Met
            925                 930                 935 att gac tct gaa tgt cgg cca aga ttc cgg gag ttg gtg tct gaa ttc        2928
Ile Asp Ser Glu Cys Arg Pro Arg Phe Arg Glu Leu Val Ser Glu Phe
        940                 945                 950 tcc cgc atg gcc agg gac ccc cag cgc ttt gtg gtc atc cag aat gag        2976
Ser Arg Met Ala Arg Asp Pro Gln Arg Phe Val Val Ile Gln Asn Glu
    955                 960                 965 gac ttg ggc cca gcc agt ccc ttg gac agc acc ttc tac cgc tca ctg        3024
Asp Leu Gly Pro Ala Ser Pro Leu Asp Ser Thr Phe Tyr Arg Ser Leu
970                 975                 980                 985 ctg gag gac gat gac atg ggg gac ctg gtg gat gct gag gag tat ctg        3072
Leu Glu Asp Asp Asp Met Gly Asp Leu Val Asp Ala Glu Glu Tyr Leu
                990                 995                 1000 gta ccc cag cag ggc ttc ttc tgt cca gac cct gcc ccg ggc gct ggg        3120
Val Pro Gln Gln Gly Phe Phe Cys Pro Asp Pro Ala Pro Gly Ala Gly
            1005                1010                1015 ggc atg gtc cac cac agg cac cgc agc tca tct acc agg agt ggc ggt        3168
Gly Met Val His His Arg His Arg Ser Ser Ser Thr Arg Ser Gly Gly
        1020                1025                1030 ggg gac ctg aca cta ggg ctg gag ccc tct gaa gag gag gcc ccc agg        3216
Gly Asp Leu Thr Leu Gly Leu Glu Pro Ser Glu Glu Glu Ala Pro Arg
    1035                1040                1045 tct cca ctg gca ccc tcc gaa ggg gct ggc tcc gat gta ttt gat ggt        3264
Ser Pro Leu Ala Pro Ser Glu Gly Ala Gly Ser Asp Val Phe Asp Gly
1050                1055                1060                1065 gac ctg gga atg ggg gca gcc aag ggg ctg caa agc ctc ccc aca cat        3312
Asp Leu Gly Met Gly Ala Ala Lys Gly Leu Gln Ser Leu Pro Thr His
                1070                1075                1080
```

-continued

```
gac ccc agc cct cta cag cgg tac agt gag gac ccc aca gta ccc ctg      3360
Asp Pro Ser Pro Leu Gln Arg Tyr Ser Glu Asp Pro Thr Val Pro Leu
        1085                1090                1095 ccc tct gag act gat ggc tac gtt gcc ccc ctg acc tgc agc ccc cag      3408
Pro Ser Glu Thr Asp Gly Tyr Val Ala Pro Leu Thr Cys Ser Pro Gln
    1100                1105                1110 cct gaa tat gtg aac cag cca gat gtt cgg ccc cag ccc cct tcg ccc      3456
Pro Glu Tyr Val Asn Gln Pro Asp Val Arg Pro Gln Pro Pro Ser Pro
1115                1120                1125 cga gag ggc cct ctg cct gct gcc cga cct gct ggt gcc act ctg gaa      3504
Arg Glu Gly Pro Leu Pro Ala Ala Arg Pro Ala Gly Ala Thr Leu Glu
1130                1135                1140                1145 agg gcc aag act ctc tcc cca ggg aag aat ggg gtc gtc aaa gac gtt      3552
Arg Ala Lys Thr Leu Ser Pro Gly Lys Asn Gly Val Val Lys Asp Val
                1150                1155                1160 ttt gcc ttt ggg ggt gcc gtg gag aac ccc gag tac ttg aca ccc cag      3600
Phe Ala Phe Gly Gly Ala Val Glu Asn Pro Glu Tyr Leu Thr Pro Gln
            1165                1170                1175 gga gga gct gcc cct cag ccc cac cct cct cct gcc ttc agc cca gcc      3648
Gly Gly Ala Ala Pro Gln Pro His Pro Pro Pro Ala Phe Ser Pro Ala
        1180                1185                1190 ttc gac aac ctc tat tac tgg gac cag gac cca cca gag cgg ggg gct      3696
Phe Asp Asn Leu Tyr Tyr Trp Asp Gln Asp Pro Pro Glu Arg Gly Ala
    1195                1200                1205 cca ccc agc acc ttc aaa ggg aca cct acg gca gag aac cca gag tac      3744
Pro Pro Ser Thr Phe Lys Gly Thr Pro Thr Ala Glu Asn Pro Glu Tyr
1210                1215                1220                1225 ctg ggt ctg gac gtg cca gtg tga                                      3768
Leu Gly Leu Asp Val Pro Val
                1230

<210> SEQ ID NO 4
<211> LENGTH: 1255
<212> TYPE: PRT
<213> ORGANISM: Homo sapiens

<400> SEQUENCE: 4

Met Glu Leu Ala Ala Leu Cys Arg Trp Gly Leu Leu Ala Leu Leu
            -20                 -15                 -10

Pro Pro Gly Ala Ala Ser Thr Gln Val Cys Thr Gly Thr Asp Met Lys
        -5                  -1   1               5

Leu Arg Leu Pro Ala Ser Pro Glu Thr His Leu Asp Met Leu Arg His
 10                  15                  20                  25

Leu Tyr Gln Gly Cys Gln Val Val Gln Gly Asn Leu Glu Leu Thr Tyr
                30                  35                  40

Leu Pro Thr Asn Ala Ser Leu Ser Phe Leu Gln Asp Ile Gln Glu Val
            45                  50                  55

Gln Gly Tyr Val Leu Ile Ala His Asn Gln Val Arg Gln Val Pro Leu
        60                  65                  70

Gln Arg Leu Arg Ile Val Arg Gly Thr Gln Leu Phe Glu Asp Asn Tyr
    75                  80                  85

Ala Leu Ala Val Leu Asp Asn Gly Asp Pro Leu Asn Asn Thr Thr Pro
 90                  95                 100                 105

Val Thr Gly Ala Ser Pro Gly Gly Leu Arg Glu Leu Gln Leu Arg Ser
                110                 115                 120

Leu Thr Glu Ile Leu Lys Gly Gly Val Leu Ile Gln Arg Asn Pro Gln
            125                 130                 135
```

-continued

Leu Cys Tyr Gln Asp Thr Ile Leu Trp Lys Asp Ile Phe His Lys Asn
        140                 145                 150

Asn Gln Leu Ala Leu Thr Leu Ile Asp Thr Asn Arg Ser Arg Ala Cys
        155                 160                 165

His Pro Cys Ser Pro Met Cys Lys Gly Ser Arg Cys Trp Gly Glu Ser
170                 175                 180                 185

Ser Glu Asp Cys Gln Ser Leu Thr Arg Thr Val Cys Ala Gly Gly Cys
                190                 195                 200

Ala Arg Cys Lys Gly Pro Leu Pro Thr Asp Cys Cys His Glu Gln Cys
            205                 210                 215

Ala Ala Gly Cys Thr Gly Pro Lys His Ser Asp Cys Leu Ala Cys Leu
        220                 225                 230

His Phe Asn His Ser Gly Ile Cys Glu Leu His Cys Pro Ala Leu Val
        235                 240                 245

Thr Tyr Asn Thr Asp Thr Phe Glu Ser Met Pro Asn Pro Glu Gly Arg
250                 255                 260                 265

Tyr Thr Phe Gly Ala Ser Cys Val Thr Ala Cys Pro Tyr Asn Tyr Leu
                270                 275                 280

Ser Thr Asp Val Gly Ser Cys Thr Leu Val Cys Pro Leu His Asn Gln
            285                 290                 295

Glu Val Thr Ala Glu Asp Gly Thr Gln Arg Cys Glu Lys Cys Ser Lys
        300                 305                 310

Pro Cys Ala Arg Val Cys Tyr Gly Leu Gly Met Glu His Leu Arg Glu
        315                 320                 325

Val Arg Ala Val Thr Ser Ala Asn Ile Gln Glu Phe Ala Gly Cys Lys
330                 335                 340                 345

Lys Ile Phe Gly Ser Leu Ala Phe Leu Pro Glu Ser Phe Asp Gly Asp
                350                 355                 360

Pro Ala Ser Asn Thr Ala Pro Leu Gln Pro Glu Gln Leu Gln Val Phe
            365                 370                 375

Glu Thr Leu Glu Glu Ile Thr Gly Tyr Leu Tyr Ile Ser Ala Trp Pro
        380                 385                 390

Asp Ser Leu Pro Asp Leu Ser Val Phe Gln Asn Leu Gln Val Ile Arg
        395                 400                 405

Gly Arg Ile Leu His Asn Gly Ala Tyr Ser Leu Thr Leu Gln Gly Leu
410                 415                 420                 425

Gly Ile Ser Trp Leu Gly Leu Arg Ser Leu Arg Glu Leu Gly Ser Gly
                430                 435                 440

Leu Ala Leu Ile His His Asn Thr His Leu Cys Phe Val His Thr Val
            445                 450                 455

Pro Trp Asp Gln Leu Phe Arg Asn Pro His Gln Ala Leu Leu His Thr
        460                 465                 470

Ala Asn Arg Pro Glu Asp Glu Cys Val Gly Glu Gly Leu Ala Cys His
        475                 480                 485

Gln Leu Cys Ala Arg Gly His Cys Trp Gly Pro Gly Pro Thr Gln Cys
490                 495                 500                 505

Val Asn Cys Ser Gln Phe Leu Arg Gly Gln Glu Cys Val Glu Glu Cys
                510                 515                 520

Arg Val Leu Gln Gly Leu Pro Arg Glu Tyr Val Asn Ala Arg His Cys
            525                 530                 535

Leu Pro Cys His Pro Glu Cys Gln Pro Gln Asn Gly Ser Val Thr Cys
        540                 545                 550

-continued

Phe Gly Pro Glu Ala Asp Gln Cys Val Ala Cys Ala His Tyr Lys Asp
    555                 560             565

Pro Pro Phe Cys Val Ala Arg Cys Pro Ser Gly Val Lys Pro Asp Leu
570             575             580             585

Ser Tyr Met Pro Ile Trp Lys Phe Pro Asp Glu Glu Gly Ala Cys Gln
            590             595             600

Pro Cys Pro Ile Asn Cys Thr His Ser Cys Val Asp Leu Asp Asp Lys
            605             610             615

Gly Cys Pro Ala Glu Gln Arg Ala Ser Pro Leu Thr Ser Ile Val Ser
        620             625             630

Ala Val Val Gly Ile Leu Leu Val Val Leu Gly Val Val Phe Gly
        635             640             645

Ile Leu Ile Lys Arg Arg Gln Gln Lys Ile Arg Lys Tyr Thr Met Arg
650             655             660             665

Arg Leu Leu Gln Glu Thr Glu Leu Val Glu Pro Leu Thr Pro Ser Gly
            670             675             680

Ala Met Pro Asn Gln Ala Gln Met Arg Ile Leu Lys Glu Thr Glu Leu
            685             690             695

Arg Lys Val Lys Val Leu Gly Ser Gly Ala Phe Gly Thr Val Tyr Lys
        700             705             710

Gly Ile Trp Ile Pro Asp Gly Glu Asn Val Lys Ile Pro Val Ala Ile
    715             720             725

Lys Val Leu Arg Glu Asn Thr Ser Pro Lys Ala Asn Lys Glu Ile Leu
730             735             740             745

Asp Glu Ala Tyr Val Met Ala Gly Val Gly Ser Pro Tyr Val Ser Arg
            750             755             760

Leu Leu Gly Ile Cys Leu Thr Ser Thr Val Gln Leu Val Thr Gln Leu
        765             770             775

Met Pro Tyr Gly Cys Leu Leu Asp His Val Arg Glu Asn Arg Gly Arg
        780             785             790

Leu Gly Ser Gln Asp Leu Leu Asn Trp Cys Met Gln Ile Ala Lys Gly
    795             800             805

Met Ser Tyr Leu Glu Asp Val Arg Leu Val His Arg Asp Leu Ala Ala
810             815             820             825

Arg Asn Val Leu Val Lys Ser Pro Asn His Val Lys Ile Thr Asp Phe
            830             835             840

Gly Leu Ala Arg Leu Leu Asp Ile Asp Glu Thr Glu Tyr His Ala Asp
        845             850             855

Gly Gly Lys Val Pro Ile Lys Trp Met Ala Leu Glu Ser Ile Leu Arg
        860             865             870

Arg Arg Phe Thr His Gln Ser Asp Val Trp Ser Tyr Gly Val Thr Val
    875             880             885

Trp Glu Leu Met Thr Phe Gly Ala Lys Pro Tyr Asp Gly Ile Pro Ala
890             895             900             905

Arg Glu Ile Pro Asp Leu Leu Glu Lys Gly Glu Arg Leu Pro Gln Pro
            910             915             920

Pro Ile Cys Thr Ile Asp Val Tyr Met Ile Met Val Lys Cys Trp Met
            925             930             935

Ile Asp Ser Glu Cys Arg Pro Arg Phe Arg Glu Leu Val Ser Glu Phe
        940             945             950

Ser Arg Met Ala Arg Asp Pro Gln Arg Phe Val Val Ile Gln Asn Glu
    955             960             965

-continued

```
Asp Leu Gly Pro Ala Ser Pro Leu Asp Ser Thr Phe Tyr Arg Ser Leu
970                 975                 980                 985

Leu Glu Asp Asp Asp Met Gly Asp Leu Val Asp Ala Glu Glu Tyr Leu
                990                 995                 1000

Val Pro Gln Gln Gly Phe Phe Cys Pro Asp Pro Ala Pro Gly Ala Gly
            1005                1010                1015

Gly Met Val His His Arg His Arg Ser Ser Ser Thr Arg Ser Gly Gly
        1020                1025                1030

Gly Asp Leu Thr Leu Gly Leu Glu Pro Ser Glu Glu Glu Ala Pro Arg
    1035                1040                1045

Ser Pro Leu Ala Pro Ser Glu Gly Ala Gly Ser Asp Val Phe Asp Gly
1050                1055                1060                1065

Asp Leu Gly Met Gly Ala Ala Lys Gly Leu Gln Ser Leu Pro Thr His
                1070                1075                1080

Asp Pro Ser Pro Leu Gln Arg Tyr Ser Glu Asp Pro Thr Val Pro Leu
            1085                1090                1095

Pro Ser Glu Thr Asp Gly Tyr Val Ala Pro Leu Thr Cys Ser Pro Gln
        1100                1105                1110

Pro Glu Tyr Val Asn Gln Pro Asp Val Arg Pro Gln Pro Pro Ser Pro
    1115                1120                1125

Arg Glu Gly Pro Leu Pro Ala Ala Arg Pro Ala Gly Ala Thr Leu Glu
1130                1135                1140                1145

Arg Ala Lys Thr Leu Ser Pro Gly Lys Asn Gly Val Val Lys Asp Val
                1150                1155                1160

Phe Ala Phe Gly Gly Ala Val Glu Asn Pro Glu Tyr Leu Thr Pro Gln
            1165                1170                1175

Gly Gly Ala Ala Pro Gln Pro His Pro Pro Pro Ala Phe Ser Pro Ala
        1180                1185                1190

Phe Asp Asn Leu Tyr Tyr Trp Asp Gln Asp Pro Pro Glu Arg Gly Ala
    1195                1200                1205

Pro Pro Ser Thr Phe Lys Gly Thr Pro Thr Ala Glu Asn Pro Glu Tyr
1210                1215                1220                1225

Leu Gly Leu Asp Val Pro Val
            1230

<210> SEQ ID NO 5
<211> LENGTH: 648
<212> TYPE: DNA
<213> ORGANISM: Homo sapiens
<220> FEATURE:
<221> NAME/KEY: CDS
<222> LOCATION: (1)..(648)

<400> SEQUENCE: 5 atg ggc agc ccc cgc tcc gcg ctg agc tgc ctg ctg ttg cac ttg ctg     48
Met Gly Ser Pro Arg Ser Ala Leu Ser Cys Leu Leu Leu His Leu Leu
1               5                   10                  15 gtt ctc tgc ctc caa gcc cag gta act gtt cag tcc tca cct aat ttt     96
Val Leu Cys Leu Gln Ala Gln Val Thr Val Gln Ser Ser Pro Asn Phe
            20                  25                  30 aca cag cat gtg agg gag cag agc ctg gtg acg gat cag ctc agc cgc    144
Thr Gln His Val Arg Glu Gln Ser Leu Val Thr Asp Gln Leu Ser Arg
        35                  40                  45 cgc ctc atc cgg acc tac cag ctc tac agc cgc acc agc ggg aag cac    192
Arg Leu Ile Arg Thr Tyr Gln Leu Tyr Ser Arg Thr Ser Gly Lys His
    50                  55                  60
```

```
gtg cag gtc ctg gcc aac aag cgc atc aac gcc atg gca gaa gac gga    240
Val Gln Val Leu Ala Asn Lys Arg Ile Asn Ala Met Ala Glu Asp Gly
 65                  70                  75                  80 gac ccc ttc gcg aag ctc att gtg gag acc gat act ttt gga agc aga    288
Asp Pro Phe Ala Lys Leu Ile Val Glu Thr Asp Thr Phe Gly Ser Arg
                 85                  90                  95 gtc cga gtt cgc ggc gca gag aca ggt ctc tac atc tgc atg aac aag    336
Val Arg Val Arg Gly Ala Glu Thr Gly Leu Tyr Ile Cys Met Asn Lys
            100                 105                 110 aag ggg aag cta att gcc aag agc aac ggc aaa ggc aag gac tgc gta    384
Lys Gly Lys Leu Ile Ala Lys Ser Asn Gly Lys Gly Lys Asp Cys Val
        115                 120                 125 ttc aca gag atc gtg ctg gag aac aac tac acg gcg ctg cag aac gcc    432
Phe Thr Glu Ile Val Leu Glu Asn Asn Tyr Thr Ala Leu Gln Asn Ala
    130                 135                 140 aag tac gag ggc tgg tac atg gcc ttt acc cgc aag ggc cgg ccc cgc    480
Lys Tyr Glu Gly Trp Tyr Met Ala Phe Thr Arg Lys Gly Arg Pro Arg
145                 150                 155                 160 aag ggc tcc aag acg cgc cag cat cag cgc gag gtg cac ttc atg aag    528
Lys Gly Ser Lys Thr Arg Gln His Gln Arg Glu Val His Phe Met Lys
                165                 170                 175 cgc ctg ccg cgg ggc cac cac acc acc gag cag agc ctg cgc ttc gag    576
Arg Leu Pro Arg Gly His His Thr Thr Glu Gln Ser Leu Arg Phe Glu
            180                 185                 190 ttc ctc aac tac ccg ccc ttc acg cgc agc ctg cgc ggc agc cag agg    624
Phe Leu Asn Tyr Pro Pro Phe Thr Arg Ser Leu Arg Gly Ser Gln Arg
        195                 200                 205 act tgg gcc ccg gag ccc cga tag                                    648
Thr Trp Ala Pro Glu Pro Arg
    210                 215

<210> SEQ ID NO 6
<211> LENGTH: 215
<212> TYPE: PRT
<213> ORGANISM: Homo sapiens

<400> SEQUENCE: 6

Met Gly Ser Pro Arg Ser Ala Leu Ser Cys Leu Leu His Leu Leu
  1               5                  10                  15

Val Leu Cys Leu Gln Ala Gln Val Thr Val Gln Ser Ser Pro Asn Phe
                 20                  25                  30

Thr Gln His Val Arg Glu Gln Ser Leu Val Thr Asp Gln Leu Ser Arg
             35                  40                  45

Arg Leu Ile Arg Thr Tyr Gln Leu Tyr Ser Arg Thr Ser Gly Lys His
         50                  55                  60

Val Gln Val Leu Ala Asn Lys Arg Ile Asn Ala Met Ala Glu Asp Gly
 65                  70                  75                  80

Asp Pro Phe Ala Lys Leu Ile Val Glu Thr Asp Thr Phe Gly Ser Arg
                 85                  90                  95

Val Arg Val Arg Gly Ala Glu Thr Gly Leu Tyr Ile Cys Met Asn Lys
            100                 105                 110

Lys Gly Lys Leu Ile Ala Lys Ser Asn Gly Lys Gly Lys Asp Cys Val
        115                 120                 125

Phe Thr Glu Ile Val Leu Glu Asn Asn Tyr Thr Ala Leu Gln Asn Ala
    130                 135                 140

Lys Tyr Glu Gly Trp Tyr Met Ala Phe Thr Arg Lys Gly Arg Pro Arg
145                 150                 155                 160
```

```
Lys Gly Ser Lys Thr Arg Gln His Gln Arg Glu Val His Phe Met Lys
            165                 170                 175

Arg Leu Pro Arg Gly His His Thr Thr Glu Gln Ser Leu Arg Phe Glu
            180                 185                 190

Phe Leu Asn Tyr Pro Pro Phe Thr Arg Ser Leu Arg Gly Ser Gln Arg
            195                 200                 205

Thr Trp Ala Pro Glu Pro Arg
        210                 215

<210> SEQ ID NO 7
<211> LENGTH: 2256
<212> TYPE: DNA
<213> ORGANISM: Mus musculus
<220> FEATURE:
<221> NAME/KEY: CDS
<222> LOCATION: (1)..(2256)

<400> SEQUENCE: 7
```

| | | | | | | | | | | | | | | | | |
|---|---|---|---|---|---|---|---|---|---|---|---|---|---|---|---|---|
| atg | tgg | aac | gca | ctg | cag | gac | aga | gac | tcc | gcg | gag | gtc | ctg | gga | cac | 48 |
| Met | Trp | Asn | Ala | Leu | Gln | Asp | Arg | Asp | Ser | Ala | Glu | Val | Leu | Gly | His | |
| 1 | | | | 5 | | | | | 10 | | | | | 15 | | |
| cgc | cag | cgc | tgg | ctc | cgt | gtt | ggg | aca | ctg | gtg | ctg | gct | tta | acc | gga | 96 |
| Arg | Gln | Arg | Trp | Leu | Arg | Val | Gly | Thr | Leu | Val | Leu | Ala | Leu | Thr | Gly | |
| | | | 20 | | | | | 25 | | | | | 30 | | | |
| acc | ttc | ctc | att | ggc | ttc | ctc | ttt | ggg | tgg | ttt | ata | aaa | cct | tcc | aat | 144 |
| Thr | Phe | Leu | Ile | Gly | Phe | Leu | Phe | Gly | Trp | Phe | Ile | Lys | Pro | Ser | Asn | |
| | | 35 | | | | | 40 | | | | | 45 | | | | |
| gaa | gct | act | ggt | aat | gtt | tcc | cat | tct | ggc | atg | aag | aag | gag | ttt | ttg | 192 |
| Glu | Ala | Thr | Gly | Asn | Val | Ser | His | Ser | Gly | Met | Lys | Lys | Glu | Phe | Leu | |
| | 50 | | | | | 55 | | | | | 60 | | | | | |
| cat | gaa | ttg | aag | gct | gag | aac | atc | aaa | aaa | ttt | tta | tac | aat | ttc | aca | 240 |
| His | Glu | Leu | Lys | Ala | Glu | Asn | Ile | Lys | Lys | Phe | Leu | Tyr | Asn | Phe | Thr | |
| 65 | | | | | 70 | | | | | 75 | | | | | 80 | |
| cgg | aca | cca | cac | ttg | gca | gga | aca | caa | aat | aat | ttt | gag | ctt | gca | aag | 288 |
| Arg | Thr | Pro | His | Leu | Ala | Gly | Thr | Gln | Asn | Asn | Phe | Glu | Leu | Ala | Lys | |
| | | | | 85 | | | | | 90 | | | | | 95 | | |
| caa | att | cat | gac | cag | tgg | aaa | gaa | ttt | ggc | ctg | gat | ttg | gtt | gag | tta | 336 |
| Gln | Ile | His | Asp | Gln | Trp | Lys | Glu | Phe | Gly | Leu | Asp | Leu | Val | Glu | Leu | |
| | | | 100 | | | | | 105 | | | | | 110 | | | |
| tcc | cat | tac | gat | gtc | ttg | ctg | tcc | tat | cca | aat | aaa | act | cat | cct | aac | 384 |
| Ser | His | Tyr | Asp | Val | Leu | Leu | Ser | Tyr | Pro | Asn | Lys | Thr | His | Pro | Asn | |
| | | 115 | | | | | 120 | | | | | 125 | | | | |
| tat | atc | tca | ata | att | aat | gaa | gat | gga | aat | gag | att | ttc | aaa | aca | tca | 432 |
| Tyr | Ile | Ser | Ile | Ile | Asn | Glu | Asp | Gly | Asn | Glu | Ile | Phe | Lys | Thr | Ser | |
| | 130 | | | | | 135 | | | | | 140 | | | | | |
| tta | tct | gaa | cag | cca | ccc | cca | gga | tat | gag | aat | ata | tca | gat | gta | gtg | 480 |
| Leu | Ser | Glu | Gln | Pro | Pro | Pro | Gly | Tyr | Glu | Asn | Ile | Ser | Asp | Val | Val | |
| 145 | | | | | 150 | | | | | 155 | | | | | 160 | |
| cca | cca | tac | agt | gcc | ttc | tct | cca | caa | ggg | aca | cca | gag | ggt | gat | cta | 528 |
| Pro | Pro | Tyr | Ser | Ala | Phe | Ser | Pro | Gln | Gly | Thr | Pro | Glu | Gly | Asp | Leu | |
| | | | | 165 | | | | | 170 | | | | | 175 | | |
| gtg | tat | gtc | aac | tat | gca | cga | act | gaa | gac | ttc | ttt | aaa | ctg | gaa | cgg | 576 |
| Val | Tyr | Val | Asn | Tyr | Ala | Arg | Thr | Glu | Asp | Phe | Phe | Lys | Leu | Glu | Arg | |
| | | | 180 | | | | | 185 | | | | | 190 | | | |
| gaa | atg | aag | atc | agt | tgt | tct | ggg | aag | att | gtg | att | gcc | aga | tat | ggg | 624 |
| Glu | Met | Lys | Ile | Ser | Cys | Ser | Gly | Lys | Ile | Val | Ile | Ala | Arg | Tyr | Gly | |
| | | 195 | | | | | 200 | | | | | 205 | | | | |
| aaa | gtg | ttc | aga | gga | aat | atg | gtt | aaa | aat | gct | caa | ctg | gca | ggg | gca | 672 |
| Lys | Val | Phe | Arg | Gly | Asn | Met | Val | Lys | Asn | Ala | Gln | Leu | Ala | Gly | Ala | |
| | 210 | | | | | 215 | | | | | 220 | | | | | |

-continued

| | |
|---|---|
| aaa gga atg att ctg tac tca gac cct gct gac tac ttt gtt cct gcg<br>Lys Gly Met Ile Leu Tyr Ser Asp Pro Ala Asp Tyr Phe Val Pro Ala<br>225                  230                  235              240 | 720 |
| gtg aag tcc tat cca gat ggc tgg aac ctc cct gga ggt ggt gtc caa<br>Val Lys Ser Tyr Pro Asp Gly Trp Asn Leu Pro Gly Gly Gly Val Gln<br>                  245                  250                  255 | 768 |
| cgt gga aat gtc tta aat ctt aat ggt gca ggt gac ccg ctc aca cca<br>Arg Gly Asn Val Leu Asn Leu Asn Gly Ala Gly Asp Pro Leu Thr Pro<br>            260                  265                  270 | 816 |
| ggt tac cca gca aat gaa cat gct tat agg cat gag ttg aca aac gct<br>Gly Tyr Pro Ala Asn Glu His Ala Tyr Arg His Glu Leu Thr Asn Ala<br>                  275                  280                  285 | 864 |
| gtt ggc ctt cca agt att cct gtc cat cct att gga tat gat gat gca<br>Val Gly Leu Pro Ser Ile Pro Val His Pro Ile Gly Tyr Asp Asp Ala<br>290                  295                  300 | 912 |
| cag aaa ctc tta gaa cac atg ggt ggt cca gca ccc cct gac agt agc<br>Gln Lys Leu Leu Glu His Met Gly Gly Pro Ala Pro Pro Asp Ser Ser<br>305                  310                  315                  320 | 960 |
| tgg aag gga gga tta aaa gtg cct tac aac gtg gga cct ggc ttt gct<br>Trp Lys Gly Gly Leu Lys Val Pro Tyr Asn Val Gly Pro Gly Phe Ala<br>                  325                  330                  335 | 1008 |
| gga aac ttt tca aca caa aag gtc aag atg cat att cac tct tac act<br>Gly Asn Phe Ser Thr Gln Lys Val Lys Met His Ile His Ser Tyr Thr<br>            340                  345                  350 | 1056 |
| aaa gtg aca aga atc tat aat gtc att ggc acc ctc aaa gga gct ctg<br>Lys Val Thr Arg Ile Tyr Asn Val Ile Gly Thr Leu Lys Gly Ala Leu<br>                  355                  360                  365 | 1104 |
| gaa cca gac aga tat gtt att ctt gga ggt cac cga gac gct tgg gta<br>Glu Pro Asp Arg Tyr Val Ile Leu Gly Gly His Arg Asp Ala Trp Val<br>370                  375                  380 | 1152 |
| ttt ggt ggc att gac cct cag agt gga gca gct gtt gtt cat gaa att<br>Phe Gly Gly Ile Asp Pro Gln Ser Gly Ala Ala Val Val His Glu Ile<br>385                  390                  395                  400 | 1200 |
| gtg cgg agc ttt gga acc ctg aag aag aaa gga cgg agg cct aga agg<br>Val Arg Ser Phe Gly Thr Leu Lys Lys Lys Gly Arg Arg Pro Arg Arg<br>                  405                  410                  415 | 1248 |
| aca att ttg ttt gca agc tgg gat gca gaa gaa ttt ggc ctt ctt ggt<br>Thr Ile Leu Phe Ala Ser Trp Asp Ala Glu Glu Phe Gly Leu Leu Gly<br>            420                  425                  430 | 1296 |
| tct act gag tgg gca gag gaa cat tca aga ctc cta caa gag cga ggt<br>Ser Thr Glu Trp Ala Glu Glu His Ser Arg Leu Leu Gln Glu Arg Gly<br>                  435                  440                  445 | 1344 |
| gtg gct tat att aat gct gat tct tcc ata gaa gga aat tac act cta<br>Val Ala Tyr Ile Asn Ala Asp Ser Ser Ile Glu Gly Asn Tyr Thr Leu<br>450                  455                  460 | 1392 |
| aga gtt gat tgc aca cca ctg atg tac agc tta gtg tac aac cta aca<br>Arg Val Asp Cys Thr Pro Leu Met Tyr Ser Leu Val Tyr Asn Leu Thr<br>465                  470                  475                  480 | 1440 |
| aaa gag ctg caa agc cca gat gaa ggt ttt gaa gga aaa tct ctt tat<br>Lys Glu Leu Gln Ser Pro Asp Glu Gly Phe Glu Gly Lys Ser Leu Tyr<br>                  485                  490                  495 | 1488 |
| gac agc tgg aaa gaa aag agt cct tca cct gag ttc att gga atg ccc<br>Asp Ser Trp Lys Glu Lys Ser Pro Ser Pro Glu Phe Ile Gly Met Pro<br>            500                  505                  510 | 1536 |
| aga att agc aag ctg ggg tct ggc aat gat ttt gaa gtg ttc ttc caa<br>Arg Ile Ser Lys Leu Gly Ser Gly Asn Asp Phe Glu Val Phe Phe Gln<br>                  515                  520                  525 | 1584 |
| aga ctt gga att gct tca ggc aga gcc cga tat act aaa aat tgg aaa<br>Arg Leu Gly Ile Ala Ser Gly Arg Ala Arg Tyr Thr Lys Asn Trp Lys<br>530                  535                  540 | 1632 |

-continued

```
act aac aaa gtc agc agc tat cct ctc tat cac agt gtc tat gaa aca    1680
Thr Asn Lys Val Ser Ser Tyr Pro Leu Tyr His Ser Val Tyr Glu Thr
545                 550                 555                 560 tat gag ctg gta gta aaa ttt tat gac cca aca ttt aaa tac cac ctc    1728
Tyr Glu Leu Val Val Lys Phe Tyr Asp Pro Thr Phe Lys Tyr His Leu
        565                 570                 575 act gtg gcc cag gtt cga gga gcg atg gta ttt gaa ctt gcc aat tct    1776
Thr Val Ala Gln Val Arg Gly Ala Met Val Phe Glu Leu Ala Asn Ser
                580                 585                 590 ata gtg ctt ccc ttt gac tgc caa agt tat gct gta gct ctg aag aag    1824
Ile Val Leu Pro Phe Asp Cys Gln Ser Tyr Ala Val Ala Leu Lys Lys
            595                 600                 605 tat gct gac act atc tac aat att tca atg aaa cat cca caa gaa atg    1872
Tyr Ala Asp Thr Ile Tyr Asn Ile Ser Met Lys His Pro Gln Glu Met
610                 615                 620 aag gct tac atg ata tca ttt gat tca ctg ttt tct gca gtc aat aat    1920
Lys Ala Tyr Met Ile Ser Phe Asp Ser Leu Phe Ser Ala Val Asn Asn
625                 630                 635                 640 ttt aca gat gtt gca tct aag ttc aat cag aga ctg caa gag tta gac    1968
Phe Thr Asp Val Ala Ser Lys Phe Asn Gln Arg Leu Gln Glu Leu Asp
        645                 650                 655 aaa agc aac ccc ata tta ctg aga att atg aat gac cag ctg atg tat    2016
Lys Ser Asn Pro Ile Leu Leu Arg Ile Met Asn Asp Gln Leu Met Tyr
                660                 665                 670 ctg gaa cgt gca ttc att gat cct tta ggc tta cca gga agg cct ttc    2064
Leu Glu Arg Ala Phe Ile Asp Pro Leu Gly Leu Pro Gly Arg Pro Phe
            675                 680                 685 tac agg cat acc atc tat gct cca agc agc cac aac aag tat gca gga    2112
Tyr Arg His Thr Ile Tyr Ala Pro Ser Ser His Asn Lys Tyr Ala Gly
690                 695                 700 gaa tca ttc cct ggg att tat gat gcc ctt ttt gat ata agt agc aaa    2160
Glu Ser Phe Pro Gly Ile Tyr Asp Ala Leu Phe Asp Ile Ser Ser Lys
705                 710                 715                 720 gtc aat gct tct aag gcc tgg aac gaa gtg aag aga cag att tct att    2208
Val Asn Ala Ser Lys Ala Trp Asn Glu Val Lys Arg Gln Ile Ser Ile
        725                 730                 735 gca acc ttt aca gtg caa gct gca gca gag act ctg agg gaa gta gct    2256
Ala Thr Phe Thr Val Gln Ala Ala Ala Glu Thr Leu Arg Glu Val Ala
                740                 745                 750
```

<210> SEQ ID NO 8
<211> LENGTH: 752
<212> TYPE: PRT
<213> ORGANISM: Mus musculus

<400> SEQUENCE: 8

```
Met Trp Asn Ala Leu Gln Asp Arg Asp Ser Ala Glu Val Leu Gly His
1               5                   10                  15

Arg Gln Arg Trp Leu Arg Val Gly Thr Leu Val Leu Ala Leu Thr Gly
            20                  25                  30

Thr Phe Leu Ile Gly Phe Leu Phe Gly Trp Phe Ile Lys Pro Ser Asn
        35                  40                  45

Glu Ala Thr Gly Asn Val Ser His Ser Gly Met Lys Lys Glu Phe Leu
    50                  55                  60

His Glu Leu Lys Ala Glu Asn Ile Lys Lys Phe Leu Tyr Asn Phe Thr
65                  70                  75                  80

Arg Thr Pro His Leu Ala Gly Thr Gln Asn Asn Phe Glu Leu Ala Lys
                85                  90                  95
```

-continued

```
Gln Ile His Asp Gln Trp Lys Glu Phe Gly Leu Asp Leu Val Glu Leu
            100                 105                 110

Ser His Tyr Asp Val Leu Leu Ser Tyr Pro Asn Lys Thr His Pro Asn
            115                 120                 125

Tyr Ile Ser Ile Ile Asn Glu Asp Gly Asn Glu Ile Phe Lys Thr Ser
            130                 135                 140

Leu Ser Glu Gln Pro Pro Gly Tyr Glu Asn Ile Ser Asp Val Val
145                 150                 155                 160

Pro Pro Tyr Ser Ala Phe Ser Pro Gln Gly Thr Pro Glu Gly Asp Leu
                165                 170                 175

Val Tyr Val Asn Tyr Ala Arg Thr Glu Asp Phe Lys Leu Glu Arg
            180                 185                 190

Glu Met Lys Ile Ser Cys Ser Gly Lys Ile Val Ile Ala Arg Tyr Gly
            195                 200                 205

Lys Val Phe Arg Gly Asn Met Val Lys Asn Ala Gln Leu Ala Gly Ala
            210                 215                 220

Lys Gly Met Ile Leu Tyr Ser Asp Pro Ala Asp Tyr Phe Val Pro Ala
225                 230                 235                 240

Val Lys Ser Tyr Pro Asp Gly Trp Asn Leu Pro Gly Gly Val Gln
                245                 250                 255

Arg Gly Asn Val Leu Asn Leu Asn Gly Ala Gly Asp Pro Leu Thr Pro
            260                 265                 270

Gly Tyr Pro Ala Asn Glu His Ala Tyr Arg His Glu Leu Thr Asn Ala
            275                 280                 285

Val Gly Leu Pro Ser Ile Pro Val His Pro Ile Gly Tyr Asp Asp Ala
            290                 295                 300

Gln Lys Leu Leu Glu His Met Gly Gly Pro Ala Pro Pro Asp Ser Ser
305                 310                 315                 320

Trp Lys Gly Gly Leu Lys Val Pro Tyr Asn Val Gly Pro Gly Phe Ala
                325                 330                 335

Gly Asn Phe Ser Thr Gln Lys Val Lys Met His Ile His Ser Tyr Thr
            340                 345                 350

Lys Val Thr Arg Ile Tyr Asn Val Ile Gly Thr Leu Lys Gly Ala Leu
            355                 360                 365

Glu Pro Asp Arg Tyr Val Ile Leu Gly Gly His Arg Asp Ala Trp Val
            370                 375                 380

Phe Gly Gly Ile Asp Pro Gln Ser Gly Ala Ala Val Val His Glu Ile
385                 390                 395                 400

Val Arg Ser Phe Gly Thr Leu Lys Lys Lys Gly Arg Pro Arg Arg
            405                 410                 415

Thr Ile Leu Phe Ala Ser Trp Asp Ala Glu Glu Phe Gly Leu Leu Gly
            420                 425                 430

Ser Thr Glu Trp Ala Glu Glu His Ser Arg Leu Leu Gln Glu Arg Gly
            435                 440                 445

Val Ala Tyr Ile Asn Ala Asp Ser Ser Ile Glu Gly Asn Tyr Thr Leu
            450                 455                 460

Arg Val Asp Cys Thr Pro Leu Met Tyr Ser Leu Val Tyr Asn Leu Thr
465                 470                 475                 480

Lys Glu Leu Gln Ser Pro Asp Glu Gly Phe Glu Gly Lys Ser Leu Tyr
                485                 490                 495

Asp Ser Trp Lys Glu Lys Ser Pro Ser Pro Glu Phe Ile Gly Met Pro
            500                 505                 510
```

```
Arg Ile Ser Lys Leu Gly Ser Gly Asn Asp Phe Glu Val Phe Phe Gln
        515                 520                 525

Arg Leu Gly Ile Ala Ser Gly Arg Ala Arg Tyr Thr Lys Asn Trp Lys
        530                 535                 540

Thr Asn Lys Val Ser Ser Tyr Pro Leu Tyr His Ser Val Tyr Glu Thr
545                 550                 555                 560

Tyr Glu Leu Val Val Lys Phe Tyr Asp Pro Thr Phe Lys Tyr His Leu
                565                 570                 575

Thr Val Ala Gln Val Arg Gly Ala Met Val Phe Glu Leu Ala Asn Ser
            580                 585                 590

Ile Val Leu Pro Phe Asp Cys Gln Ser Tyr Ala Val Ala Leu Lys Lys
        595                 600                 605

Tyr Ala Asp Thr Ile Tyr Asn Ile Ser Met Lys His Pro Gln Glu Met
    610                 615                 620

Lys Ala Tyr Met Ile Ser Phe Asp Ser Leu Phe Ser Ala Val Asn Asn
625                 630                 635                 640

Phe Thr Asp Val Ala Ser Lys Phe Asn Gln Arg Leu Gln Glu Leu Asp
                645                 650                 655

Lys Ser Asn Pro Ile Leu Leu Arg Ile Met Asn Asp Gln Leu Met Tyr
            660                 665                 670

Leu Glu Arg Ala Phe Ile Asp Pro Leu Gly Leu Pro Gly Arg Pro Phe
        675                 680                 685

Tyr Arg His Thr Ile Tyr Ala Pro Ser Ser His Asn Lys Tyr Ala Gly
    690                 695                 700

Glu Ser Phe Pro Gly Ile Tyr Asp Ala Leu Phe Asp Ile Ser Ser Lys
705                 710                 715                 720

Val Asn Ala Ser Lys Ala Trp Asn Glu Val Lys Arg Gln Ile Ser Ile
                725                 730                 735

Ala Thr Phe Thr Val Gln Ala Ala Glu Thr Leu Arg Glu Val Ala
            740                 745                 750

<210> SEQ ID NO 9
<211> LENGTH: 2082
<212> TYPE: DNA
<213> ORGANISM: Mus musculus
<220> FEATURE:
<221> NAME/KEY: CDS
<222> LOCATION: (1)..(2082)

<400> SEQUENCE: 9 atg aag aag gag ttt ttg cat gaa ttg aag gct gag aac atc aaa aaa      48
Met Lys Lys Glu Phe Leu His Glu Leu Lys Ala Glu Asn Ile Lys Lys
  1               5                  10                  15 ttt tta tac aat ttc aca cgg aca cca cac ttg gca gga aca caa aat      96
Phe Leu Tyr Asn Phe Thr Arg Thr Pro His Leu Ala Gly Thr Gln Asn
             20                  25                  30 aat ttt gag ctt gca aag caa att cat gac cag tgg aaa gaa ttt ggc     144
Asn Phe Glu Leu Ala Lys Gln Ile His Asp Gln Trp Lys Glu Phe Gly
         35                  40                  45 ctg gat ttg gtt gag tta tcc cat tac gat gtc ttg ctg tcc tat cca     192
Leu Asp Leu Val Glu Leu Ser His Tyr Asp Val Leu Leu Ser Tyr Pro
     50                  55                  60 aat aaa act cat cct aac tat atc tca ata att aat gaa gat gga aat     240
Asn Lys Thr His Pro Asn Tyr Ile Ser Ile Ile Asn Glu Asp Gly Asn
 65                  70                  75                  80 gag att ttc aaa aca tca tta tct gaa cag cca ccc cca gga tat gag     288
Glu Ile Phe Lys Thr Ser Leu Ser Glu Gln Pro Pro Pro Gly Tyr Glu
                 85                  90                  95
```

-continued

| | |
|---|---|
| aat ata tca gat gta gtg cca cca tac agt gcc ttc tct cca caa ggg<br>Asn Ile Ser Asp Val Val Pro Pro Tyr Ser Ala Phe Ser Pro Gln Gly<br>              100                      105                  110 | 336 |
| aca cca gag ggt gat cta gtg tat gtc aac tat gca cga act gaa gac<br>Thr Pro Glu Gly Asp Leu Val Tyr Val Asn Tyr Ala Arg Thr Glu Asp<br>        115                      120                    125 | 384 |
| ttc ttt aaa ctg gaa cgg gaa atg aag atc agt tgt tct ggg aag att<br>Phe Phe Lys Leu Glu Arg Glu Met Lys Ile Ser Cys Ser Gly Lys Ile<br>130                      135                    140 | 432 |
| gtg att gcc aga tat ggg aaa gtg ttc aga gga aat atg gtt aaa aat<br>Val Ile Ala Arg Tyr Gly Lys Val Phe Arg Gly Asn Met Val Lys Asn<br>145                  150                    155                    160 | 480 |
| gct caa ctg gca ggg gca aaa gga atg att ctg tac tca gac cct gct<br>Ala Gln Leu Ala Gly Ala Lys Gly Met Ile Leu Tyr Ser Asp Pro Ala<br>                165                    170                    175 | 528 |
| gac tac ttt gtt cct gcg gtg aag tcc tat cca gat ggc tgg aac ctc<br>Asp Tyr Phe Val Pro Ala Val Lys Ser Tyr Pro Asp Gly Trp Asn Leu<br>                    180                    185                    190 | 576 |
| cct gga ggt ggt gtc caa cgt gga aat gtc tta aat ctt aat ggt gca<br>Pro Gly Gly Gly Val Gln Arg Gly Asn Val Leu Asn Leu Asn Gly Ala<br>        195                      200                    205 | 624 |
| ggt gac ccg ctc aca cca ggt tac cca gca aat gaa cat gct tat agg<br>Gly Asp Pro Leu Thr Pro Gly Tyr Pro Ala Asn Glu His Ala Tyr Arg<br>210                      215                    220 | 672 |
| cat gag ttg aca aac gct gtt ggc ctt cca agt att cct gtc cat cct<br>His Glu Leu Thr Asn Ala Val Gly Leu Pro Ser Ile Pro Val His Pro<br>225                      230                    235                    240 | 720 |
| att gga tat gat gat gca cag aaa ctc tta gaa cac atg ggt ggt cca<br>Ile Gly Tyr Asp Asp Ala Gln Lys Leu Leu Glu His Met Gly Gly Pro<br>                        245                    250                    255 | 768 |
| gca ccc cct gac agt agc tgg aag gga gga tta aaa gtg cct tac aac<br>Ala Pro Pro Asp Ser Ser Trp Lys Gly Gly Leu Lys Val Pro Tyr Asn<br>                    260                    265                    270 | 816 |
| gtg gga cct ggc ttt gct gga aac ttt tca aca caa aag gtc aag atg<br>Val Gly Pro Gly Phe Ala Gly Asn Phe Ser Thr Gln Lys Val Lys Met<br>        275                      280                    285 | 864 |
| cat att cac tct tac act aaa gtg aca aga atc tat aat gtc att ggc<br>His Ile His Ser Tyr Thr Lys Val Thr Arg Ile Tyr Asn Val Ile Gly<br>290                      295                    300 | 912 |
| acc ctc aaa gga gct ctg gaa cca gac aga tat gtt att ctt gga ggt<br>Thr Leu Lys Gly Ala Leu Glu Pro Asp Arg Tyr Val Ile Leu Gly Gly<br>305                      310                    315                    320 | 960 |
| cac cga gac gct tgg gta ttt ggt ggc att gac cct cag agt gga gca<br>His Arg Asp Ala Trp Val Phe Gly Gly Ile Asp Pro Gln Ser Gly Ala<br>                        325                    330                    335 | 1008 |
| gct gtt gtt cat gaa att gtg cgg agc ttt gga acc ctg aag aag aaa<br>Ala Val Val His Glu Ile Val Arg Ser Phe Gly Thr Leu Lys Lys Lys<br>                  340                    345                    350 | 1056 |
| gga cgg agg cct aga agg aca att ttg ttt gca agc tgg gat gca gaa<br>Gly Arg Arg Pro Arg Arg Thr Ile Leu Phe Ala Ser Trp Asp Ala Glu<br>        355                      360                    365 | 1104 |
| gaa ttt ggc ctt ctt ggt tct act gag tgg gca gag gaa cat tca aga<br>Glu Phe Gly Leu Leu Gly Ser Thr Glu Trp Ala Glu Glu His Ser Arg<br>370                      375                    380 | 1152 |
| ctc cta caa gag cga ggt gtg gct tat att aat gct gat tct tcc ata<br>Leu Leu Gln Glu Arg Gly Val Ala Tyr Ile Asn Ala Asp Ser Ser Ile<br>385                      390                    395                    400 | 1200 |
| gaa gga aat tac act cta aga gtt gat tgc aca cca ctg atg tac agc<br>Glu Gly Asn Tyr Thr Leu Arg Val Asp Cys Thr Pro Leu Met Tyr Ser<br>                        405                    410                    415 | 1248 |

|  |  |  |  |  |  |  |  |  |  |  |  |  |  |  |  |
|---|---|---|---|---|---|---|---|---|---|---|---|---|---|---|---|
| tta | gtg | tac | aac | cta | aca | aaa | gag | ctg | caa | agc | cca | gat | gaa | ggt | ttt |
| Leu | Val | Tyr | Asn | Leu | Thr | Lys | Glu | Leu | Gln | Ser | Pro | Asp | Glu | Gly | Phe |

```
                tta gtg tac aac cta aca aaa gag ctg caa agc cca gat gaa ggt ttt      1296
                Leu Val Tyr Asn Leu Thr Lys Glu Leu Gln Ser Pro Asp Glu Gly Phe
                                420                 425                 430 gaa gga aaa tct ctt tat gac agc tgg aaa gaa aag agt cct tca cct      1344
                Glu Gly Lys Ser Leu Tyr Asp Ser Trp Lys Glu Lys Ser Pro Ser Pro
                                    435                 440                 445 gag ttc att gga atg ccc aga att agc aag ctg ggg tct ggc aat gat      1392
                Glu Phe Ile Gly Met Pro Arg Ile Ser Lys Leu Gly Ser Gly Asn Asp
                450                 455                 460 ttt gaa gtg ttc ttc caa aga ctt gga att gct tca ggc aga gcc cga      1440
                Phe Glu Val Phe Phe Gln Arg Leu Gly Ile Ala Ser Gly Arg Ala Arg
                465                 470                 475                 480 tat act aaa aat tgg aaa act aac aaa gtc agc agc tat cct ctc tat      1488
                Tyr Thr Lys Asn Trp Lys Thr Asn Lys Val Ser Ser Tyr Pro Leu Tyr
                                    485                 490                 495 cac agt gtc tat gaa aca tat gag ctg gta gta aaa ttt tat gac cca      1536
                His Ser Val Tyr Glu Thr Tyr Glu Leu Val Val Lys Phe Tyr Asp Pro
                                500                 505                 510 aca ttt aaa tac cac ctc act gtg gcc cag gtt cga gga gcg atg gta      1584
                Thr Phe Lys Tyr His Leu Thr Val Ala Gln Val Arg Gly Ala Met Val
                                515                 520                 525 ttt gaa ctt gcc aat tct ata gtg ctt ccc ttt gac tgc caa agt tat      1632
                Phe Glu Leu Ala Asn Ser Ile Val Leu Pro Phe Asp Cys Gln Ser Tyr
                530                 535                 540 gct gta gct ctg aag aag tat gct gac act atc tac aat att tca atg      1680
                Ala Val Ala Leu Lys Lys Tyr Ala Asp Thr Ile Tyr Asn Ile Ser Met
                545                 550                 555                 560 aaa cat cca caa gaa atg aag gct tac atg ata tca ttt gat tca ctg      1728
                Lys His Pro Gln Glu Met Lys Ala Tyr Met Ile Ser Phe Asp Ser Leu
                                565                 570                 575 ttt tct gca gtc aat aat ttt aca gat gtt gca tct aag ttc aat cag      1776
                Phe Ser Ala Val Asn Asn Phe Thr Asp Val Ala Ser Lys Phe Asn Gln
                                580                 585                 590 aga ctg caa gag tta gac aaa agc aac ccc ata tta ctg aga att atg      1824
                Arg Leu Gln Glu Leu Asp Lys Ser Asn Pro Ile Leu Leu Arg Ile Met
                                595                 600                 605 aat gac cag ctg atg tat ctg gaa cgt gca ttc att gat cct tta ggc      1872
                Asn Asp Gln Leu Met Tyr Leu Glu Arg Ala Phe Ile Asp Pro Leu Gly
                610                 615                 620 tta cca gga agg cct ttc tac agg cat acc atc tat gct cca agc agc      1920
                Leu Pro Gly Arg Pro Phe Tyr Arg His Thr Ile Tyr Ala Pro Ser Ser
                625                 630                 635                 640 cac aac aag tat gca gga gaa tca ttc cct ggg att tat gat gcc ctt      1968
                His Asn Lys Tyr Ala Gly Glu Ser Phe Pro Gly Ile Tyr Asp Ala Leu
                                645                 650                 655 ttt gat ata agt agc aaa gtc aat gct tct aag gcc tgg aac gaa gtg      2016
                Phe Asp Ile Ser Ser Lys Val Asn Ala Ser Lys Ala Trp Asn Glu Val
                                660                 665                 670 aag aga cag att tct att gca acc ttt aca gtg caa gct gca gca gag      2064
                Lys Arg Gln Ile Ser Ile Ala Thr Phe Thr Val Gln Ala Ala Ala Glu
                                675                 680                 685 act ctg agg gaa gta gct                                              2082
                Thr Leu Arg Glu Val Ala
                    690

<210> SEQ ID NO 10
<211> LENGTH: 694
<212> TYPE: PRT
<213> ORGANISM: Mus musculus
```

-continued

```
<400> SEQUENCE: 10

Met Lys Lys Glu Phe Leu His Glu Leu Lys Ala Glu Asn Ile Lys Lys
  1               5                  10                  15

Phe Leu Tyr Asn Phe Thr Arg Thr Pro His Leu Ala Gly Thr Gln Asn
             20                  25                  30

Asn Phe Glu Leu Ala Lys Gln Ile His Asp Gln Trp Lys Glu Phe Gly
         35                  40                  45

Leu Asp Leu Val Glu Leu Ser His Tyr Asp Val Leu Leu Ser Tyr Pro
     50                  55                  60

Asn Lys Thr His Pro Asn Tyr Ile Ser Ile Asn Glu Asp Gly Asn
 65                  70                  75                  80

Glu Ile Phe Lys Thr Ser Leu Ser Gln Pro Pro Gly Tyr Glu
                 85                  90                  95

Asn Ile Ser Asp Val Pro Pro Tyr Ser Ala Phe Ser Pro Gln Gly
                100                 105                 110

Thr Pro Glu Gly Asp Leu Val Tyr Val Asn Tyr Ala Arg Thr Glu Asp
            115                 120                 125

Phe Phe Lys Leu Glu Arg Glu Met Lys Ile Ser Cys Ser Gly Lys Ile
130                 135                 140

Val Ile Ala Arg Tyr Gly Lys Val Phe Arg Gly Asn Met Val Lys Asn
145                 150                 155                 160

Ala Gln Leu Ala Gly Ala Lys Gly Met Ile Leu Tyr Ser Asp Pro Ala
                165                 170                 175

Asp Tyr Phe Val Pro Ala Val Lys Ser Tyr Pro Asp Gly Trp Asn Leu
            180                 185                 190

Pro Gly Gly Gly Val Gln Arg Gly Asn Val Leu Asn Leu Asn Gly Ala
        195                 200                 205

Gly Asp Pro Leu Thr Pro Gly Tyr Pro Ala Asn Glu His Ala Tyr Arg
    210                 215                 220

His Glu Leu Thr Asn Ala Val Gly Leu Pro Ser Ile Pro Val His Pro
225                 230                 235                 240

Ile Gly Tyr Asp Asp Ala Gln Lys Leu Leu Glu His Met Gly Gly Pro
                245                 250                 255

Ala Pro Pro Asp Ser Ser Trp Lys Gly Gly Leu Lys Val Pro Tyr Asn
            260                 265                 270

Val Gly Pro Gly Phe Ala Gly Asn Phe Ser Thr Gln Lys Val Lys Met
        275                 280                 285

His Ile His Ser Tyr Thr Lys Val Thr Arg Ile Tyr Asn Val Ile Gly
    290                 295                 300

Thr Leu Lys Gly Ala Leu Glu Pro Asp Arg Tyr Val Ile Leu Gly Gly
305                 310                 315                 320

His Arg Asp Ala Trp Val Phe Gly Gly Ile Asp Pro Gln Ser Gly Ala
                325                 330                 335

Ala Val His Glu Ile Val Arg Ser Phe Gly Thr Leu Lys Lys
            340                 345                 350

Gly Arg Arg Pro Arg Arg Thr Ile Leu Phe Ala Ser Trp Asp Ala Glu
        355                 360                 365

Glu Phe Gly Leu Leu Gly Ser Thr Glu Trp Ala Glu Glu His Ser Arg
    370                 375                 380

Leu Leu Gln Glu Arg Gly Val Ala Tyr Ile Asn Ala Asp Ser Ser Ile
385                 390                 395                 400

Glu Gly Asn Tyr Thr Leu Arg Val Asp Cys Thr Pro Leu Met Tyr Ser
                405                 410                 415
```

-continued

```
Leu Val Tyr Asn Leu Thr Lys Glu Leu Gln Ser Pro Asp Glu Gly Phe
            420                 425                 430

Glu Gly Lys Ser Leu Tyr Asp Ser Trp Lys Glu Lys Ser Pro Ser Pro
        435                 440                 445

Glu Phe Ile Gly Met Pro Arg Ile Ser Lys Leu Gly Ser Gly Asn Asp
    450                 455                 460

Phe Glu Val Phe Phe Gln Arg Leu Gly Ile Ala Ser Gly Arg Ala Arg
465                 470                 475                 480

Tyr Thr Lys Asn Trp Lys Thr Asn Lys Val Ser Ser Tyr Pro Leu Tyr
                485                 490                 495

His Ser Val Tyr Glu Thr Tyr Glu Leu Val Val Lys Phe Tyr Asp Pro
            500                 505                 510

Thr Phe Lys Tyr His Leu Thr Val Ala Gln Val Arg Gly Ala Met Val
        515                 520                 525

Phe Glu Leu Ala Asn Ser Ile Val Leu Pro Phe Asp Cys Gln Ser Tyr
    530                 535                 540

Ala Val Ala Leu Lys Lys Tyr Ala Asp Thr Ile Tyr Asn Ile Ser Met
545                 550                 555                 560

Lys His Pro Gln Glu Met Lys Ala Tyr Met Ile Ser Phe Asp Ser Leu
                565                 570                 575

Phe Ser Ala Val Asn Asn Phe Thr Asp Val Ala Ser Lys Phe Asn Gln
            580                 585                 590

Arg Leu Gln Glu Leu Asp Lys Ser Asn Pro Ile Leu Leu Arg Ile Met
        595                 600                 605

Asn Asp Gln Leu Met Tyr Leu Glu Arg Ala Phe Ile Asp Pro Leu Gly
    610                 615                 620

Leu Pro Gly Arg Pro Phe Tyr Arg His Thr Ile Tyr Ala Pro Ser Ser
625                 630                 635                 640

His Asn Lys Tyr Ala Gly Glu Ser Phe Pro Gly Ile Tyr Asp Ala Leu
                645                 650                 655

Phe Asp Ile Ser Ser Lys Val Asn Ala Ser Lys Ala Trp Asn Glu Val
            660                 665                 670

Lys Arg Gln Ile Ser Ile Ala Thr Phe Thr Val Gln Ala Ala Ala Glu
        675                 680                 685

Thr Leu Arg Glu Val Ala
        690
```

<210> SEQ ID NO 11
<211> LENGTH: 45
<212> TYPE: DNA
<213> ORGANISM: Clostridium tetani
<220> FEATURE:
<221> NAME/KEY: CDS
<222> LOCATION: (1)..(45)

<400> SEQUENCE: 11

```
cag tac atc aaa gct aac tcc aaa ttc atc ggt atc acc gag ctg        45
Gln Tyr Ile Lys Ala Asn Ser Lys Phe Ile Gly Ile Thr Glu Leu
  1               5                  10                  15
```

<210> SEQ ID NO 12
<211> LENGTH: 15
<212> TYPE: PRT
<213> ORGANISM: Clostridium tetani

<400> SEQUENCE: 12

```
Gln Tyr Ile Lys Ala Asn Ser Lys Phe Ile Gly Ile Thr Glu Leu
  1               5                  10                  15
```

```
<210> SEQ ID NO 13
<211> LENGTH: 63
<212> TYPE: DNA
<213> ORGANISM: Clostridium tetani
<220> FEATURE:
<221> NAME/KEY: CDS
<222> LOCATION: (1)..(63)

<400> SEQUENCE: 13 ttc aac aac ttc acc gta agc ttc tgg ctg cgt gtt ccg aaa gtt agc      48
Phe Asn Asn Phe Thr Val Ser Phe Trp Leu Arg Val Pro Lys Val Ser
 1               5                  10                  15 gct agc cac ctg gaa                                                  63
Ala Ser His Leu Glu
            20

<210> SEQ ID NO 14
<211> LENGTH: 21
<212> TYPE: PRT
<213> ORGANISM: Clostridium tetani

<400> SEQUENCE: 14

Phe Asn Asn Phe Thr Val Ser Phe Trp Leu Arg Val Pro Lys Val Ser
 1               5                  10                  15

Ala Ser His Leu Glu
            20

<210> SEQ ID NO 15
<211> LENGTH: 25
<212> TYPE: PRT
<213> ORGANISM: Artificial Sequence
<220> FEATURE:
<223> OTHER INFORMATION: Description of Artificial Sequence: Fusion of
      tetanus toxoid epitope and PSM

<400> SEQUENCE: 15

Gln Glu Arg Gly Val Gln Tyr Ile Lys Ala Asn Ser Lys Phe Ile Gly
 1               5                  10                  15

Ile Thr Glu Leu Arg Val Asp Cys Thr
            20                  25

<210> SEQ ID NO 16
<211> LENGTH: 25
<212> TYPE: PRT
<213> ORGANISM: Artificial Sequence
<220> FEATURE:
<223> OTHER INFORMATION: Description of Artificial Sequence: Fusion of
      tetanus toxoid epitope and PSM

<400> SEQUENCE: 16

Ala Val Val Leu Arg Gln Tyr Ile Lys Ala Asn Ser Lys Phe Ile Gly
 1               5                  10                  15

Ile Thr Glu Leu Glu Met Lys Thr Tyr
            20                  25

<210> SEQ ID NO 17
<211> LENGTH: 25
<212> TYPE: PRT
<213> ORGANISM: Artificial Sequence
<220> FEATURE:
<223> OTHER INFORMATION: Description of Artificial Sequence: Fusion of
      tetanus toxoid epitope and PSM
```

```
<400> SEQUENCE: 17

Met Phe Leu Glu Arg Gln Tyr Ile Lys Ala Asn Ser Lys Phe Ile Gly
  1               5                  10                  15

Ile Thr Glu Leu His Val Ile Tyr Ala
            20                  25

<210> SEQ ID NO 18
<211> LENGTH: 31
<212> TYPE: PRT
<213> ORGANISM: Artificial Sequence
<220> FEATURE:
<223> OTHER INFORMATION: Description of Artificial Sequence: Fusion of
      tetanus toxoid epitope and PSM

<400> SEQUENCE: 18

Asn Ser Arg Leu Leu Phe Asn Asn Phe Thr Val Ser Phe Trp Leu Arg
  1               5                  10                  15

Val Pro Lys Val Ser Ala Ser His Leu Glu Val Asp Cys Thr Pro
            20                  25                  30

<210> SEQ ID NO 19
<211> LENGTH: 31
<212> TYPE: PRT
<213> ORGANISM: Artificial Sequence
<220> FEATURE:
<223> OTHER INFORMATION: Description of Artificial Sequence: Fusion of
      tetanus toxoid epitope and PSM

<400> SEQUENCE: 19

Val Val Leu Arg Lys Phe Asn Asn Phe Thr Val Ser Phe Trp Leu Arg
  1               5                  10                  15

Val Pro Lys Val Ser Ala Ser His Leu Glu Ser Phe Asp Ser Leu
            20                  25                  30

<210> SEQ ID NO 20
<211> LENGTH: 31
<212> TYPE: PRT
<213> ORGANISM: Artificial Sequence
<220> FEATURE:
<223> OTHER INFORMATION: Description of Artificial Sequence: Fusion of
      tetanus toxoid epitope and PSM

<400> SEQUENCE: 20

Leu Met Phe Leu Glu Phe Asn Asn Phe Thr Val Ser Phe Trp Leu Arg
  1               5                  10                  15

Val Pro Lys Val Ser Ala Ser His Leu Glu Pro Ser Ser His Asn
            20                  25                  30

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Artificial
      His tag
<221> NAME/KEY: CDS
<222> LOCATION: (1)..(18)

<400> SEQUENCE: 21 cat cat cat cat cat cat                                          18
His His His His His His
  1               5
```

-continued

```
<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Artificial
      His tag

<400> SEQUENCE: 22

His His His His His His
  1               5

<210> SEQ ID NO 23
<211> LENGTH: 42
<212> TYPE: DNA
<213> ORGANISM: Artificial Sequence
<220> FEATURE:
<223> OTHER INFORMATION: Description of Artificial Sequence: Artificial
      His tag
<221> NAME/KEY: CDS
<222> LOCATION: (1)..(42)

<400> SEQUENCE: 23 atg aaa cac caa cac caa cat caa cat caa cat caa                       42
Met Lys His Gln His Gln His Gln His Gln His Gln
  1               5                  10

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Artificial
      His tag

<400> SEQUENCE: 24

Met Lys His Gln His Gln His Gln His Gln His Gln His Gln
  1               5                  10

<210> SEQ ID NO 25
<211> LENGTH: 69
<212> TYPE: DNA
<213> ORGANISM: Mus musculus
<220> FEATURE:
<221> NAME/KEY: CDS
<222> LOCATION: (1)..(69)

<400> SEQUENCE: 25 atg gat gca atg aag aga ggg ctc tgc tgt gtg ctg ctg tgt gga          48
Met Asp Ala Met Lys Arg Gly Leu Cys Cys Val Leu Leu Cys Gly
  1               5                  10                  15 gca gtc ttc gtt tcg ccc agc                                           69
Ala Val Phe Val Ser Pro Ser
                 20

<210> SEQ ID NO 26
<211> LENGTH: 23
<212> TYPE: PRT
<213> ORGANISM: Mus musculus

<400> SEQUENCE: 26

Met Asp Ala Met Lys Arg Gly Leu Cys Cys Val Leu Leu Cys Gly
  1               5                  10                  15

Ala Val Phe Val Ser Pro Ser
                 20
```

```
<210> SEQ ID NO 27
<211> LENGTH: 33
<212> TYPE: DNA
<213> ORGANISM: Homo sapiens
<220> FEATURE:
<221> NAME/KEY: CDS
<222> LOCATION: (1)..(33)

<400> SEQUENCE: 27 gaa caa aaa ctc atc tca gaa gag gat ctg aat                              33
Glu Gln Lys Leu Ile Ser Glu Glu Asp Leu Asn
 1               5                  10

<210> SEQ ID NO 28
<211> LENGTH: 11
<212> TYPE: PRT
<213> ORGANISM: Homo sapiens

<400> SEQUENCE: 28

Glu Gln Lys Leu Ile Ser Glu Glu Asp Leu Asn
 1               5                  10

<210> SEQ ID NO 29
<211> LENGTH: 75
<212> TYPE: DNA
<213> ORGANISM: Homo sapiens
<220> FEATURE:
<221> NAME/KEY: CDS
<222> LOCATION: (1)..(75)

<400> SEQUENCE: 29 atg aag gat tcc tgc atc act gtg atg gcc atg gcg ctg ctg tct ggg         48
Met Lys Asp Ser Cys Ile Thr Val Met Ala Met Ala Leu Leu Ser Gly
 1               5                  10                  15 ttc ttt ttc ttc gcg ccg gcc tcg agc                                      75
Phe Phe Phe Phe Ala Pro Ala Ser Ser
                20                  25

<210> SEQ ID NO 30
<211> LENGTH: 25
<212> TYPE: PRT
<213> ORGANISM: Homo sapiens

<400> SEQUENCE: 30

Met Lys Asp Ser Cys Ile Thr Val Met Ala Met Ala Leu Leu Ser Gly
 1               5                  10                  15

Phe Phe Phe Phe Ala Pro Ala Ser Ser
                20                  25

<210> SEQ ID NO 31
<211> LENGTH: 60
<212> TYPE: DNA
<213> ORGANISM: Mus musculus
<220> FEATURE:
<221> NAME/KEY: CDS
<222> LOCATION: (1)..(60)

<400> SEQUENCE: 31 atg aga agg atg ctt ctg cac ttg agt gtt ctg act ctc agc tgt gtc         48
Met Arg Arg Met Leu Leu His Leu Ser Val Leu Thr Leu Ser Cys Val
 1               5                  10                  15 tgg gcc act gcc                                                          60
Trp Ala Thr Ala
                20
```

-continued

```
<210> SEQ ID NO 32
<211> LENGTH: 20
<212> TYPE: PRT
<213> ORGANISM: Mus musculus

<400> SEQUENCE: 32

Met Arg Arg Met Leu Leu His Leu Ser Val Leu Thr Leu Ser Cys Val
 1               5                  10                  15

Trp Ala Thr Ala
            20

<210> SEQ ID NO 33
<211> LENGTH: 20
<212> TYPE: PRT
<213> ORGANISM: Homo sapiens

<400> SEQUENCE: 33

Pro Ala Pro Gly Ser Thr Ala Pro Ala His Gly Val Thr Ser Ala
 1               5                  10                  15

Pro Asp Thr Arg
            20

Figures 5A, 5B:
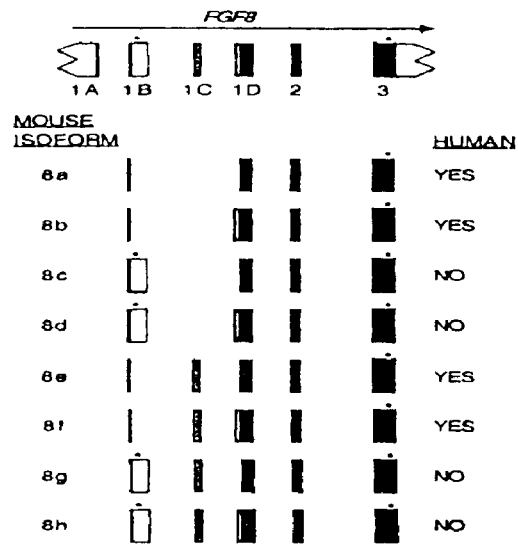

<210> SEQ ID NO 34
<211> LENGTH: 244
<212> TYPE: PRT
<213> ORGANISM: Artificial Sequence
<220> FEATURE:
<223> OTHER INFORMATION: Fig. 5B - Various FGF8 isoforms

<400> SEQUENCE: 34

Met Gly Ser Pro Arg Ser Ala Leu Ser Cys Leu Leu Leu His Leu Leu
 1               5                  10                  15

Val Leu Cys Leu Gln Ala Gln Glu Gly Pro Gly Arg Gly Pro Ala Leu
                20                  25                  30

Gly Arg Glu Leu Ala Ser Leu Phe Arg Ala Gly Arg Glu Pro Gln Gly
            35                  40                  45

Val Ser Gln Gln Val Thr Val Gln Ser Ser Pro Asn Phe Thr Gln His
        50                  55                  60

Val Arg Glu Gln Ser Leu Val Thr Asp Gln Leu Ser Arg Arg Leu Ile
65                  70                  75                  80

Arg Thr Tyr Gln Leu Tyr Ser Arg Thr Ser Gly Lys His Val Gln Val
                85                  90                  95

Leu Ala Asn Lys Arg Ile Asn Ala Met Ala Glu Asp Gly Asp Pro Phe
            100                 105                 110

Ala Lys Leu Ile Val Glu Thr Asp Thr Phe Gly Ser Arg Val Arg Val
        115                 120                 125

Arg Gly Ala Glu Thr Gly Leu Tyr Ile Cys Met Asn Lys Lys Gly Lys
    130                 135                 140

Leu Ile Ala Lys Ser Asn Gly Lys Gly Lys Asp Cys Val Phe Thr Glu
145                 150                 155                 160

Ile Val Leu Glu Asn Asn Tyr Thr Ala Leu Gln Asn Ala Lys Tyr Glu
                165                 170                 175

Gly Trp Tyr Met Ala Phe Thr Arg Lys Gly Arg Pro Arg Lys Gly Ser
            180                 185                 190

Lys Thr Arg Gln His Gln Arg Glu Val His Phe Met Lys Arg Leu Pro
        195                 200                 205

Arg Gly His His Thr Thr Glu Gln Ser Leu Arg Phe Glu Phe Leu Asn
    210                 215                 220
```

```
Tyr Pro Pro Phe Thr Arg Ser Leu Arg Gly Ser Gln Arg Thr Trp Ala
225                 230                 235                 240

Pro Glu Pro Arg

<210> SEQ ID NO 35
<211> LENGTH: 215
<212> TYPE: PRT
<213> ORGANISM: Homo sapiens
<220> FEATURE:
<221> NAME/KEY: misc_feature
<222> LOCATION: (1)..(215)
<223> OTHER INFORMATION: Fig. 6 - Wild Type (WT) FGF8b

<400> SEQUENCE: 35

Met Gly Ser Pro Arg Ser Ala Leu Ser Cys Leu Leu Leu His Leu Leu
1               5                   10                  15

Val Leu Cys Leu Gln Ala Gln Val Thr Val Gln Ser Ser Pro Asn Phe
                20                  25                  30

Thr Gln His Val Arg Glu Gln Ser Leu Val Thr Asp Gln Leu Ser Arg
            35                  40                  45

Arg Leu Ile Arg Thr Tyr Gln Leu Tyr Ser Arg Thr Ser Gly Lys His
    50                  55                  60

Val Gln Val Leu Ala Asn Lys Arg Ile Asn Ala Met Ala Glu Asp Gly
65                  70                  75                  80

Asp Pro Phe Ala Lys Leu Ile Val Glu Thr Asp Thr Phe Gly Ser Arg
                85                  90                  95

Val Arg Val Arg Gly Ala Glu Thr Gly Leu Tyr Ile Cys Met Asn Lys
            100                 105                 110

Lys Gly Lys Leu Ile Ala Lys Ser Asn Gly Lys Gly Lys Asp Cys Val
    115                 120                 125

Phe Thr Glu Ile Gly Leu Glu Asn Asn Tyr Thr Ala Leu Gln Asn Ala
130                 135                 140

Lys Tyr Glu Gly Trp Tyr Met Ala Phe Thr Arg Lys Gly Arg Pro Arg
145                 150                 155                 160

Lys Gly Ser Lys Thr Arg Gln His Gln Arg Glu Val His Phe Met Lys
                165                 170                 175

Arg Leu Pro Arg Gly His His Thr Thr Glu Gln Ser Leu Arg Phe Glu
            180                 185                 190

Phe Leu Asn Tyr Pro Pro Phe Thr Arg Ser Leu Arg Gly Ser Gln Arg
        195                 200                 205

Thr Trp Ala Pro Glu Pro Arg
    210                 215

<210> SEQ ID NO 36
<211> LENGTH: 195
<212> TYPE: PRT
<213> ORGANISM: Artificial Sequence
<220> FEATURE:
<223> OTHER INFORMATION: Fig. 6 - F30N: Variant of FGF8b with P30
      epitope in the N-terminal

<400> SEQUENCE: 36

Met Ala Gln Val Thr Val Phe Asn Asn Phe Thr Val Ser Phe Trp Leu
1               5                   10                  15

Arg Val Pro Lys Val Ser Ala Ser His Leu Glu Arg Arg Leu Ile Arg
                20                  25                  30

Thr Tyr Gln Leu Tyr Ser Arg Thr Ser Gly Lys His Val Gln Val Leu
            35                  40                  45
```

```
Ala Asn Lys Arg Ile Asn Ala Met Ala Glu Asp Gly Asp Pro Phe Ala
         50                  55                  60

Lys Leu Ile Val Glu Thr Asp Thr Phe Gly Ser Arg Val Arg Val Arg
 65                  70                  75                  80

Gly Ala Glu Thr Gly Leu Tyr Ile Cys Met Asn Lys Lys Gly Lys Leu
                 85                  90                  95

Ile Ala Lys Ser Asn Gly Lys Gly Lys Asp Cys Val Phe Thr Glu Ile
            100                 105                 110

Gly Leu Glu Asn Asn Tyr Thr Ala Leu Gln Asn Ala Lys Tyr Glu Gly
            115                 120                 125

Trp Tyr Met Ala Phe Thr Arg Lys Gly Arg Pro Arg Lys Gly Ser Lys
        130                 135                 140

Thr Arg Gln His Gln Arg Glu Val His Phe Met Lys Arg Leu Pro Arg
145                 150                 155                 160

Gly His His Thr Thr Glu Gln Ser Leu Arg Phe Glu Phe Leu Asn Tyr
                165                 170                 175

Pro Pro Phe Thr Arg Ser Leu Arg Gly Ser Gln Arg Thr Trp Ala Pro
            180                 185                 190

Glu Pro Arg
        195

<210> SEQ ID NO 37
<211> LENGTH: 208
<212> TYPE: PRT
<213> ORGANISM: Artificial Sequence
<220> FEATURE:
<223> OTHER INFORMATION: Fig. 6 - F2I: Internal variant of FGF8b
      constructed by replacing external loops in the FGF2 structure with
      P2 epitope

<400> SEQUENCE: 37

Met Ala Gln Val Thr Val Gln Ser Ser Pro Asn Phe Thr Gln His Val
 1               5                  10                  15

Arg Glu Gln Ser Leu Val Thr Asp Gln Leu Ser Arg Arg Leu Ile Arg
             20                  25                  30

Thr Tyr Gln Leu Tyr Ser Arg Thr Ser Gly Lys His Val Gln Val Leu
         35                  40                  45

Ala Asn Lys Arg Ile Asn Ala Met Ala Glu Asp Gly Asp Pro Phe Ala
     50                  55                  60

Lys Leu Ile Val Glu Thr Asp Gln Tyr Ile Lys Ala Asn Ser Lys Phe
 65                  70                  75                  80

Ile Gly Ile Thr Glu Leu Gly Ser Arg Val Arg Val Arg Gly Ala Glu
                 85                  90                  95

Thr Gly Leu Tyr Ile Cys Met Asn Lys Lys Gly Lys Leu Ile Ala Lys
            100                 105                 110

Ser Asn Gly Lys Gly Lys Asp Cys Val Phe Thr Glu Ile Gly Leu Glu
            115                 120                 125

Asn Asn Tyr Thr Ala Leu Gln Asn Ala Lys Tyr Glu Gly Trp Tyr Met
        130                 135                 140

Ala Phe Thr Arg Lys Gly Arg Pro Arg Lys Gly Ser Lys Thr Arg Gln
145                 150                 155                 160

His Gln Arg Glu Val His Phe Met Lys Arg Leu Pro Arg Gly His His
                165                 170                 175

Thr Thr Glu Gln Ser Leu Arg Phe Glu Phe Leu Asn Tyr Pro Pro Phe
            180                 185                 190
```

```
Thr Arg Ser Leu Arg Gly Ser Gln Arg Thr Trp Ala Pro Glu Pro Arg
        195                 200                 205
```

<210> SEQ ID NO 38
<211> LENGTH: 213
<212> TYPE: PRT
<213> ORGANISM: Artificial Sequence
<220> FEATURE:
<223> OTHER INFORMATION: Fig. 6 - F30I: Internal variant of FGF8b
      constructed by replacing external loops in the FGF2 structure with
      P30 epitope

<400> SEQUENCE:

-continued

```
Lys Leu Ile Val Glu Thr Asp Thr Phe Gly Ser Arg Val Arg Val Arg
65                  70                  75                  80

Gly Ala Glu Thr Gly Leu Tyr Ile Cys Met Asn Lys Lys Gly Lys Leu
                85                  90                  95

Ile Ala Lys Ser Asn Gly Lys Gly Lys Asp Cys Val Phe Thr Glu Ile
            100                 105                 110

Gly Leu Glu Asn Asn Tyr Thr Ala Leu Gln Asn Ala Lys Tyr Glu Gly
        115                 120                 125

Trp Tyr Met Ala Phe Thr Arg Lys Gly Arg Pro Arg Lys Gly Ser Lys
    130                 135                 140

Thr Arg Gln His Gln Arg Glu Val His Phe Met Lys Arg Leu Pro Arg
145                 150                 155                 160

Gly His His Thr Thr Glu Gln Ser Leu Arg Phe Glu Phe Leu Asn Tyr
                165                 170                 175

Pro Pro Phe Thr Gln Tyr Ile Lys Ala Asn Ser Lys Phe Ile Gly Ile
            180                 185                 190

Thr Glu Leu Pro Glu Pro Arg
        195

<210> SEQ ID NO 40
<211> LENGTH: 13
<212> TYPE: PRT
<213> ORGANISM: Artificial Sequence
<220> FEATURE:
<223> OTHER INFORMATION: A preferred pan DR epitope (PADRE) peptide has
      this sequence

<400> SEQUENCE: 40

Ala Lys Phe Val Ala Ala Trp Thr Leu Lys Ala Ala Ala
1               5                   10

<210> SEQ ID NO 41
<211> LENGTH: 11
<212> TYPE: PRT
<213> ORGANISM: Artificial Sequence
<220> FEATURE:
<223> OTHER INFORMATION: FGF8b specific peptide

<400> SEQUENCE: 41

Gln Val Thr Val Gln Ser Ser Pro Asn Phe Thr
1               5                   10
```

METHODS FOR THERAPEUTIC VACCINATION

FIELD OF THE INVENTION

This application is the national phase under 35 U.S.C. § 371 of PCT International Application No. PCT/DKS99/00525 which has an International filing date of Oct. 5, 1999, which designated the United States of America. This application also claims priority under 35 U.S.C. § 119(e) on U.S. Provisional Application No. 60/105,011 filed on Oct. 20, 1998.

The present invention relates to novel methods for combatting diseases, such as cancers, which are characterized by the presence of cell-associated gene expression products which are non-immunogenic or poorly immunogenic. In particular, the present invention relates to methods for inducing an immune response conducted by cytotoxic T-lymphocytes (CTLs), whereby cells carrying epitopes from the gene expression products are attacked and killed by the CTLs. The invention also relates to a method of preparing immunogenic, modified polypeptide antigens which are derived from weakly immunogenic antigens.

The invention further relates to a series of applications of Applicants' AutoVac technology (which is the subject of WO 95/05849) within the field of therapeutic vaccination against cancer.

BACKGROUND OF THE INVENTION

The idea of vaccinating against cancer has been around for more than hundred years and has enjoyed recurrent bursts of activity, particularly since the turn of this century.

However, during the past 10 years the understanding of the fundamental molecular mechanisms of the immune response has improved considerably. Among the most important milestones achieved during this period has been the discovery of the still growing list of cytokines and growth factors, the understanding of the mechanisms of interaction between T and B cells as well as the establishment of the cellular antigen processing pathways including the role and structure of the MHC class I and II molecules in antigen presentation.

Important discoveries with regard to cancer immunology—although still not fully understood—were also the elucidation of the mechanisms underlying induction of immunological tolerance in a host. All this research has led to a huge amount of efforts in order to develop new treatments for human cancer.

Depending on how tumour immunity is acquired by the patient, immunotherapy regimens can be categorised as either passive or active. In passive immunotherapy regimens the patient passively receives immune components such as cytokines, antibodies, cytotoxic T-cells, or lymphocyte activated killer (LAK) cells. In contrast, active specific immunotherapy protocols encompass actively inducing tumour immunity by vaccination with the tumour cell or its antigenic components. This latter form of treatment is preferred because the immunity is prolonged.

Passive and active cancer vaccines have focussed on inducing either humoral or cellular immune responses. For active vaccines it is well established that induction of CD4 positive T helper cells is necessary in order to secondarily induce either antibodies or cytotoxic CD8 positive T cells.

Passive Vaccination with Antibodies

Since the discovery of the monoclonal antibody technology in the mid-seventies, a large number of therapeutic monoclonal antibodies directed against tumour specific or tumour associated antigens has been developed. Monoclonal antibody therapy, however, gives rise to several serious problems:

Injection of these foreign substances induces an immune response in the patient towards the injected antibodies, which may lead to less efficient treatment as well as to serious allergic side-effects in the patients.

Monoclonal antibodies usually must be administered in large amounts. This is a problem, since the production costs of monoclonal antibodies are huge.

Monoclonal antibodies must be administered via the parenteral route and due to the relatively large amounts needed, the patients frequently must be hospitalised during the treatment.

Injections of monoclonal antibodies must be repeated at rather short intervals (weeks) in order to maintain therapeutic effect.

Monoclonal antibodies are usually not able to activate secondary effector systems of the immune system such as complement, NK-cells or macrophage killing of tumour cells.

The latter disadvantage is of particular importance in cancer therapy and may be an important reason why monoclonal antibody therapy of cancer in several cases has not been particularly successful. The so-called humanised monoclonal antibodies now used by many companies are less immunogenic, but unfortunately they are even less capable of activating the secondary immune effector systems. Furthermore, examples of secondary out-growth of tumours lacking the original tumour antigen have been observed, since these antibodies do not induce "innocent bystander" effects on tumour cells not carrying the tumour antigen.

The poor effector capability of the monoclonal antibodies has led to the development of monoclonal antibodies chemically conjugated to different toxins and radioisotopes. Pharmacia Upjohn AB has e.g. developed a conjugate between a monoclonal tumour specific antibody and the *Staphylococcus aureus* toxin A with the purpose of activating T cells in the tumour. Medarex Inc. has developed bispecific monoclonal antibodies containing a tumour specific Fab fragment as well as an Fc-receptor specific antibody fragment with the purpose of activating macrophage killing of tumour cells. Both constructs are more effective than the monoclonal antibody alone, but they are also more expensive and immunogenic. Antibodies conjugated to radioisotopes are also expensive as well as immunogenic and other general toxic side-effects are observed.

The appearance of the monoclonal antibody technology was a major step forward which enabled the production of well-defined, high-affinity binding molecules. However, being monoclonal these antibodies only react with a single type of epitope on a tumour antigen. This is the major reason why they usually are not able to activate the complement system or binding to the Fc-receptors of NK-cells and macrophages. These very powerful effector systems usually require the co-localisation of multiple Fc antibody fragments protruding from the antigen.

Other researchers have therefore attempted to use two monoclonal antibodies in combination and this has led to an improved effect. It therefore seems very reasonable instead to attack tumour cells with highly specific polyclonal antibodies directed against a tumour specific, or against (over-expressed) tumour associated antigens or growth factor receptors. Such antibodies would be fully capable of activating the secondary effector systems mentioned above. Furthermore, it is likely that the local inflammatory reaction induced by these effector systems could lead to secondary effects on "innocent bystander" cells not expressing the tumour antigen in question as well as to activation of tumour specific TIL's (tumour infiltrating lymphocytes) in the tumour tissue. Such effects have been observed by Medarex Inc. using their bi-specific monoclonal antibody conjugates.

Since the discovery of the monoclonal antibody technology the potential use of polyclonal antibodies for cancer therapy has not been explored very much (except for the antigens described below). One major reason is that well-defined tumour specific or tumour associated surface antigens only have been characterised within the recent years, but—more importantly—many of these have turned out to be self-antigens and therefore non-immunogenic. Accordingly, xenogenic polyclonal antibodies would necessarily have been used to study the effects. However, such antibodies induce a vigorous immune response towards the injected foreign polyclonal antibodies which rapidly eliminate the therapeutic effects.

Active Vaccination to Induce Antibodies

Recent attempts to induce therapeutic polyclonal autoantibodies in cancer patients by active vaccination have been successful. Vaccines against membrane bound carbohydrate self-antigens (such as the O-linked aberrantly expressed Tn and sTn-antigens and the ganglioside liposaccharides GM2 and GD3) have been developed. These small carbohydrate structures are, however, very poor antigens so conjugates of these molecules with carrier molecules such as keyhole limpet haemocyanin (KLH) or sheep mucins (containing Tn- and sTn) must be used. In melanoma patients the induction of anti-GM2 antibodies were associated with a prolonged disease-free interval and overall survival after a minimum follow-up of fifty-one months. Also randomised phase II studies have been conducted on breast cancer patients using a conjugate of sTn and KLH in the DETOX-B adjuvant (BIOMIRA Inc.) showing that sTn immune patients had a significantly longer median survival compared to controls. Another example of the active induction of polyclonal antibodies in cancer is the use of idiotype specific vaccination against B-cell lymphomas, which—although it has been promising—is limited to this cancer type only.

Finally, the US company Aphton Inc. has developed active conjugate vaccines against gonadotropin releasing hormone (GnRH) and gastrin. It has been demonstrated, that this vaccine is capable of controlling the biological activity of these hormones, which also can function as autocrine growth factors for certain tumour cells. Successful phase II clinical trials have been conducted on gastrointestinal cancer patients and phase III clinical trials are underway.

Cytotoxic T-Cells

It has been clearly demonstrated by several groups that tumour specific cytotoxic T cells (CTL's) are present in many tumours. These CTL's are termed tumour infiltrating lymphocytes (TIL's). However, these cells are somehow rendered non-responsive or anergic by several different possible mechanisms including secretion of immunosuppressive cytokines by the tumour cells, lack of co-stimulatory signals, down regulation of MHC class I molecules etc.

There has been many attempts to isolate the tumour specific HLA class I bound peptides recognised by TILs, and in some cases it has also been successful (e.g. peptides from the melanoma associated antigens). Such peptides have been used to induce a tumour specific immune response in the host, but the practical use of tumour specific peptides in vaccines is restricted to a limited segment of the population due to the narrow HLA class I binding specificity of the peptides.

Furthermore, it is usually relatively difficult to evoke a CTL response in vivo using synthetic peptides due to the low biological half-life of these substances as well as the difficulties with exogenous priming of MHC class I molecules.

Many other approaches have been attempted in order to evoke a tumour specific CTL response including the use of cytokines (e.g. IL-2, IFN-(, IL-6, IL-4, IL-10 or GM-CSF) or co-stimulatory molecules (B7) either in soluble form or expressed by the transfected tumour cell. Furthermore, immunisations with allogenic or autologous whole cells, or of tumour antigens prepared in specialised adjuvants designed to present the antigen via the MHC class I antigen presentation route, or tumour antigens expressed in e.g. vaccinia vectors etc. have been used with varying success. Still the general belief among tumour immunologists is therefore that one of the best ways to eliminate tumours would be to induce a strong specific anti-tumour CTL response.

Apart from the fact that these treatments usually are very expensive and difficult to reproduce, it has also turned out to be difficult to obtain a good immune response towards the tumour since many of the tumour associated antigens are true self-proteins to which most T cells appear to be tolerant. Therefore, it seems necessary to induce a controlled cellular autoimmune condition in the patient.

OBJECT OF THE INVENTION

It is an object of the present invention to provide improved methods and agents for inducing immune responses in host organisms against undesirable antigens, e.g. tumour antigens. It is a further object to provide a method for preparing polypeptide analogues of such undesirable antigens, analogues which are capable of inducing an effective immune response against the undesired antigen.

SUMMARY OF THE INVENTION

Presentation of antigens has dogmatically been thought of as two discrete pathways, a class II exogenous and a class I endogenous pathway.

Briefly, a foreign protein from outside the cell or from the cell membrane is taken up by the APC as an endosome which fuses with an intracellular compartment which contains proteolytic enzymes and MHC class II molecules. Some of the produced peptides bind to class II, which then are translocated to the cell membrane.

The class I endogenous pathway is characterised by the predominant presentation of cytosolic proteins. This is believed to occur by proteasome mediated cleavage followed by transportation of the peptides into the endoplasmic reticulum (ER) via TAP molecules located in the membrane of the ER. In ER the peptides bind to class I followed by transportation to the plasma membrane.

However, these 2 pathways are not fully distinct. For example it is known that dendritic cells and to some extend macrophages are capable of endocytosing (pinocytosing) extracellular proteins and subsequently present them in the context of MHC class I. It has also previously been demonstrated that using specialised administration routes, e.g. by coupling to iron oxide beads, exogenous antigens are capable of entering the Class I pathway (Rock, 1996). This mechanism seems central, because of the importance of a concomitant expression of both class I and class II on the same APC to elicit a three cell type cluster. This three cell type cluster of interaction has been proposed by Mitchison (1987) and later by other authors. They showed the importance of concomitant presentation of class I and class II epitopes on the same APC. According to the recently described mechanism for CTL activation (cf. Lanzavecchia, 1998, Nature 393: 413, Matzinger, 1999, Nature Med. 5: 616, Ridge et al., 1998, Nature 393: 474, Bennett et al., 1998, Nature 393: 478, Schoenberger et al., 1998, Nature 393: 480, Ossendrop et al., 1998, J. Exp. Med 187: 693, and Mackey et al., 1998, J. Immunol 161: 2094), professional APCs presenting antigen on MHC class II are recognized by T helper cells. This results in an activation of the APC (mediated by interaction by CD40L on the T helper cell and CD40 on the APC). This enables the APC to directly stimulate CTLs which are thereby activated. Cf. also FIG. 2.

It has previously been demonstrated that insertion of a foreign MHC class II restricted T helper cell epitope into a self-antigen results in the provision of an antigen capable of inducing strong cross-reactive antibody responses directed against the non-modified self-antigen (cf. applicant's WO 95/05849). It was shown that the autoantibody induction is caused by specific T cell help induced by the inserted foreign epitope.

However, we have come to the conclusion that modified self-antigens—with the aid of appropriate adjuvants—ought to be capable of also inducing strong CTL responses against MHC class I restricted self-epitopes and hence the technology described in WO 95/05849 can be adapted to also provide vaccination against intracellular and other cell-associated antigens which have epitopes presented in the context of MHC Class I.

The autovaccine technology described in WO 95/05849 has the effect that specific T cell help is provided to self-reactive B cells when a modified self-antigen is administered for uptake into the MHC class II antigen processing pathway (cf. FIG. 1, and Dalum I et al., 1996, J. Immunol. 157: 4796–4804 as well as Dalum I et al., 1999, Nature Biotechnol. 17: 666–669). It was shown that potentially self-reactive B-lymphocytes recognizing self-proteins are physiologically present in normal individuals. However, in order for these B-lymphocytes to be induced to actually produce antibodies reactive with the relevant self-proteins, assistance is needed from cytokine producing T-helper lymphocytes ($T_H$-cells or $T_H$-lymphocytes). Normally this help is not provided because T-lymphocytes in general do not recognize T-cell epitopes derived from self-proteins when presented by antigen presenting cells (APCs). However, by providing an element of "foreignness" in a self-protein (i.e. by introducing an immunologically significant modification), T-cells recognizing the foreign element are activated upon recognizing the foreign epitope on an APC (such as, initially, a mononuclear cell). Polyclonal B-lymphocytes (which present T-cell epitopes) capable of recognising self-epitopes on the modified self-protein also internalise the antigen and subsequently presents the foreign T-cell epitope(s) thereof, and the activated T-lymphocytes subsequently provide cytokine help to these self-reactive polyclonal B-lymphocytes. Since the antibodies produced by these polyclonal B-lymphocytes are reactive with different epitopes on the modified polypeptide, including those which are also present in the native polypeptide, an antibody cross-reactive with the non-modified self-protein is induced. In conclusion, the T-lymphocytes can be led to act as if the population of polyclonal B-lymphocytes have recognised an entirely foreign antigen, whereas in fact only the inserted epitope(s) is/are foreign to the host. In this way, antibodies capable of cross-reacting with non-modified self-antigens are induced.

As mentioned above, CTL's also require specific T cell help, although the mechanism for this is still not clear.

We have based the present invention on our novel theory that the self-proteins containing foreign MHC class II epitopes, following exogenous uptake, can gain access into the MHC class I antigen processing pathway of e.g. macrophages and dendritic cells. In this way a strong CTL response against subdominant epitopes in the self-protein could be induced. Alternatively, genes encoding modified tumour antigens could be administrated as nucleic acid vaccines eventually also leading to MHC class II as well as MHC class I mediated immune responses.

Figure 2:
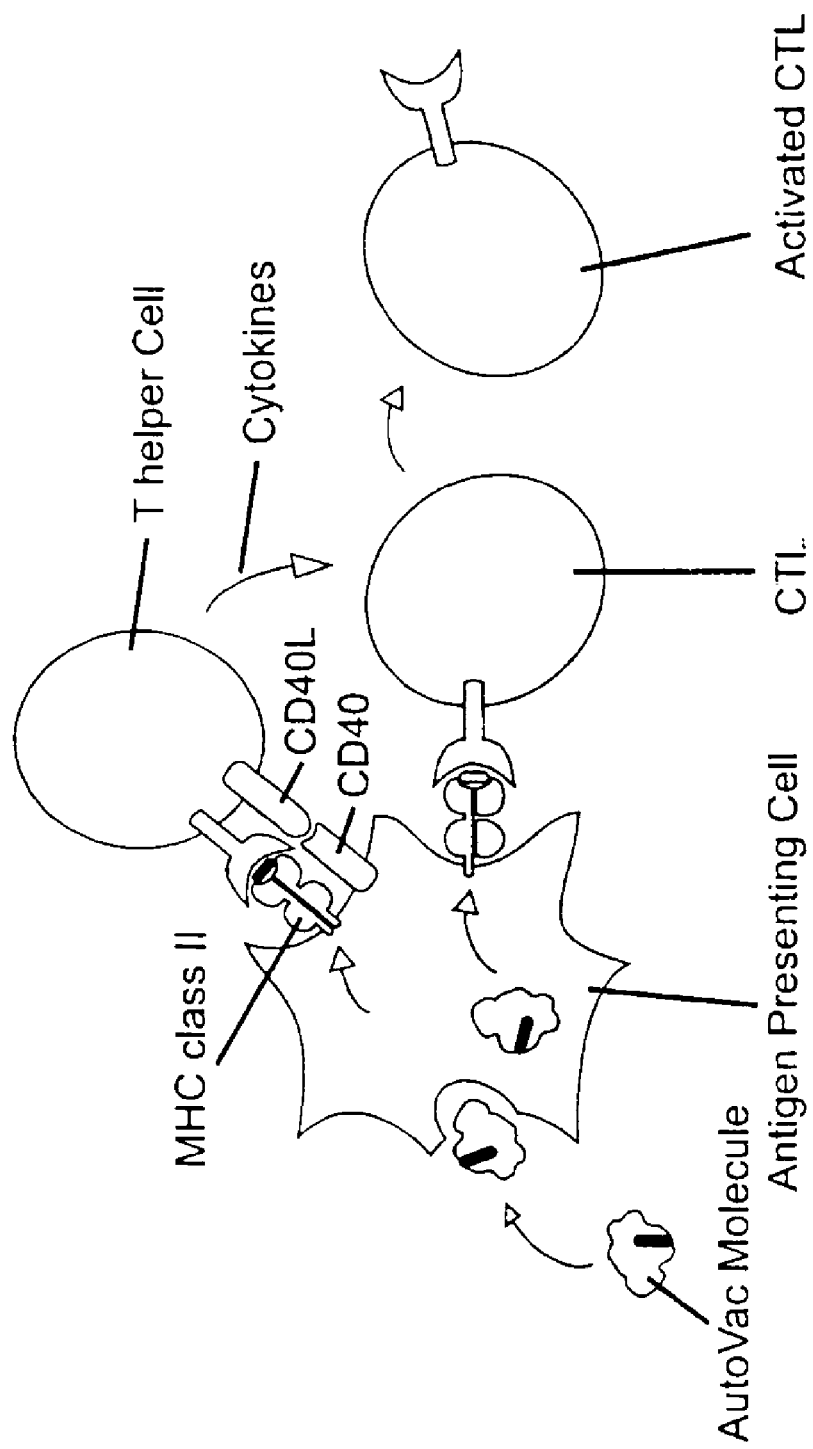

Tumour cells are very poor antigen presenting cells due to insufficient MHC class I expression, lack of co-stimulatory molecules or secretion of immunosuppressive cytokines etc. Using the autovaccine constructs and vaccination protocol mentioned above the modified tumour antigen could be presented by MHC class I as well as by MHC class II molecules on professional antigen presenting cells. Co-presentation of subdominant self-epitopes on MHC class I and immunodominant foreign epitopes on MHC class II molecules would mediate a direct cytokine help from activated MHC class II restricted T-helper cells to MHC class I restricted CTLs (FIG. 2). This will in our opinion lead to a specific break of the T cell autotolerance towards the tumour antigen and this is exactly what is desired in cancer immunotherapy.

In conclusion, a vaccine constructed using the technology outlined above will induce a humoral autoantibody response with secondary activation of complement and antibody dependent cellular cytotoxicity (ADCC) activity. It is also expected that it will induce a cytotoxic T cell response directed against e.g. a tumour specific membrane antigen.

Hence, in the broadest and most general scope, the present invention relates to a method for inducing an immune response against a polypeptide antigen in an animal, including a human being, said polypeptide antigen being weakly immunogenic or non-immunogenic in the animal, the method comprising effecting simultaneous presentation by antigen presenting cells (APCS) from the animal's immune system of an immunogenically effective amount of
1) at least one CTL epitope derived from the polypeptide antigen and/or at least one B-cell epitope derived from the cell-associated polypeptide antigen, and
2) at least one first T helper cell epitope ($T_H$ epitope) which is foreign to the animal.

In a more specific variant of the inventive method, the invention relates to a method for down-regulating a cell-associated polypeptide antigen in an animal, including a human being, said polypeptide antigen being weakly immunogenic or non-immunogenic in the animal, by inducing a specific cytotoxic T-lymphocyte (CTL) response against cells carrying the cell-associated polypeptide antigen on their surface or harbouring the cell-associated polypeptide antigen in their intracellular compartment, the method comprising effecting, in the animal, simultaneous presentation by a suitable antigen presenting cell (APC) of
1) at least one CTL epitope derived from the cell-associated polypeptide antigen, and
2) at least one first T-helper lymphocyte ($T_H$) epitope which is foreign to the animal.

Also, the novel strategy for preparing an immunogenic agent is part of the invention. This novel strategy encompasses the selection and production of analogues of weak cell-associated antigens, where the preservation of a substantial fraction of known and predicted CTL epitopes is aimed at while at the same time introducing at least one foreign $T_H$ epitope. Furthermore, the invention relates to certain specific immunogenic constructs based on known tumour-associated antigens as well as to compositions containing these constructs.

Finally, the invention relates to nucleic acid fragments, vectors, transformed cells and other tools useful in molecular biological methods for the production of the analogues of the tumour-associated antigens.

LEGENDS TO THE FIGURE

FIG. 1: The traditional AutoVac concept. A: Tolerodominant self-epitopes presented on MHC class II on an antigen presenting cell (APC) are ignored due to depletion in the T helper cell (Th) repertoire (T helper cell indicated with dotted lines). Inserted foreign immunodominant T cell epitopes presented on MHC class II activate T helper cells and B cells (B) specific for native parts of the self-protein presenting foreign immunodominant T cell epitopes on MHC class II are activated by the cytokine help provided by the T helper cell.

FIG. 2: The AutoVac concept for inducing a CTL response. Inserted foreign immunodominant T cell epitopes presented on MHC class II activate T helper cells. CTL's recognising subdominant self-epitopes presented on MHC class I are activated by the adjacent activated T helper cell.

Figure 3:
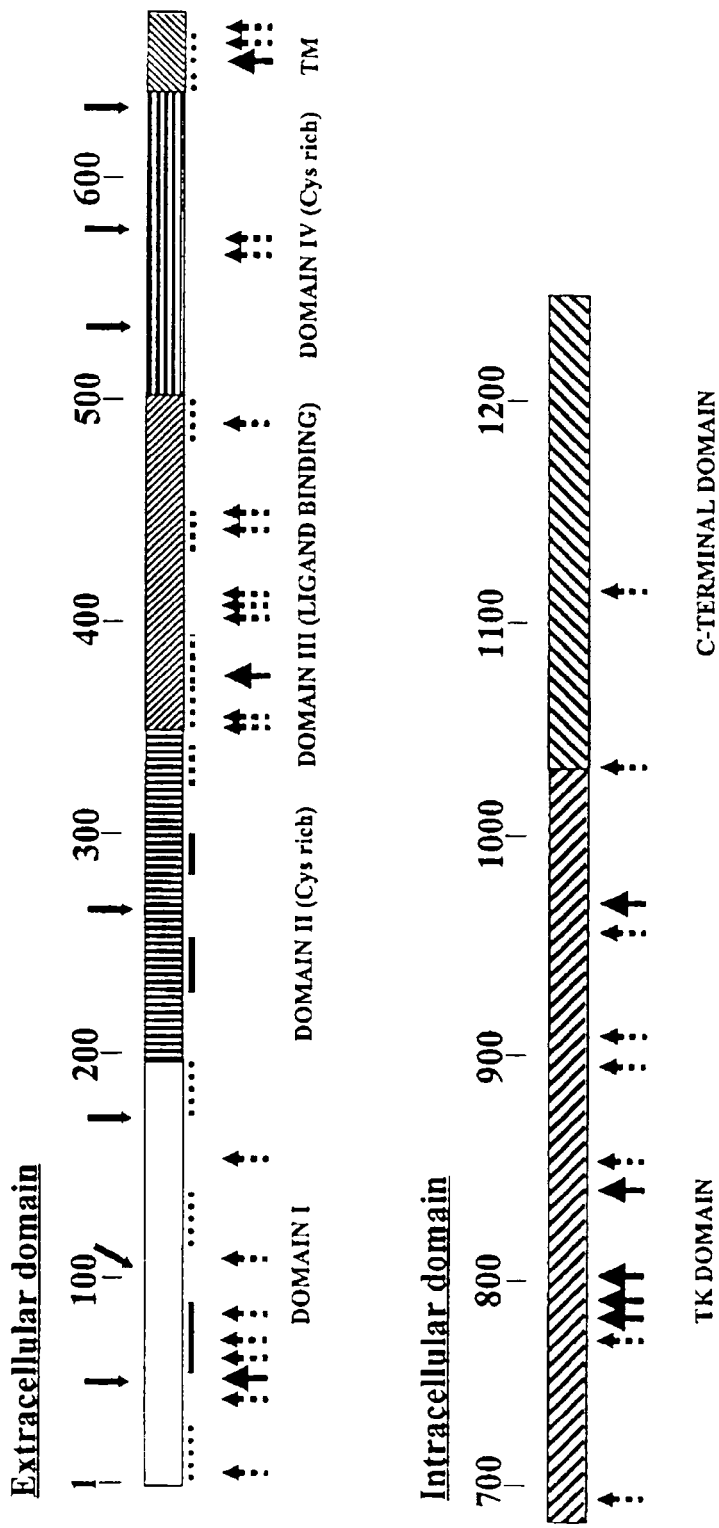

FIG. 3: A schematic representation of the Her2 polypeptide with indications of epitopic regions and N-glycosylation sites. The 4 extracellular domains, the transmembrane (TM) domain and the 2 intracellular domains are represented with indications of sites with varying degrees of homology and sites containing putative/determined CTL epitopes.

Figure 4:
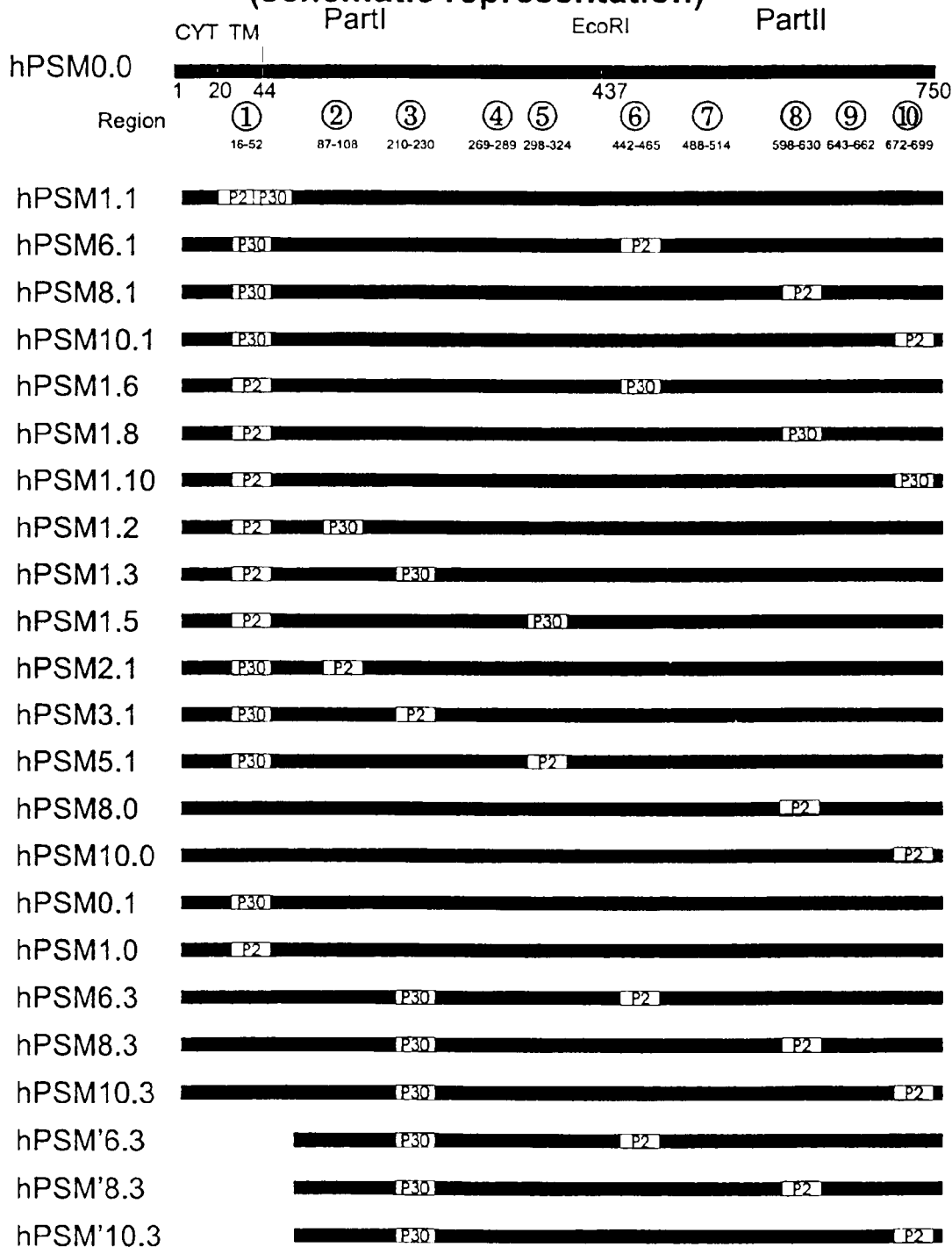

FIG. 4: A schematic representation of the human PSM polypeptide with indications of insertion regions for the P2 and P30 epitopes.

FIG. 5: The FGF genes and proteins. A: Exon-intron structure of the human and mouse FGF8 genes. Below is illustrated the eight different splice forms (from Gemel 1996). B: Amino acid sequence (SEQ ID NO: 34) of the different FGF8 isoforms. The polypeptide stretches unique to FGF8b, FGF8f, and FGF8e are indicated by bold and italic or underlined typefaces. FGF8a is the shortest variant containing none of these highlighted sequences. The signal peptide is expected to be cleaved C-terminally to Ala22. The two cysteine residues found in mature FGF8(all isoforms) are indicated by thick underlining. The two potential N-glycosylation sites of FGF8b are indicated by N. Numbering is according to FGF8b.

FIG. 6: Illustrations of the four different variants of FGF8b designed for autovaccination. Upper panel: Theoretical models of the insertion-points of the epitopes using the FGF2 crystal structure as template. Lower panel: Amino acid sequences of the wild type FGF8b (WT) and the four variants F30N, F2I, F30I, and F2C (SEQ ID NOS: 35–39, respectively). The signal peptide is marked with single underlining. The inserted peptides are marked with double underlining. The N-terminal sequence (MetAla) of all variants is due to generation of a Kozak-sequence (Kozak 1991) for better translation in eukaryotic systems.

DETAILED DISCLOSURE OF THE INVENTION

Definitions

In the following a number of terms used in the present specification and claims will be defined and explained in detail in order to clarify the metes and bounds of the invention.

A "cell-associated polypeptide antigen" is in the present specification and claims intended to denote a polypeptide which is confined to a cell which is somehow related to a pathological process. Furthermore, the cell presents CTL epitopes of the polypeptide antigen bound to MHC Class I molecules on its surface. Cell-associated polypeptide antigens can therefore be truly intracellular antigens (and thereby unreachable for a humoral immune response) or antigens bound to the surface of the cells. The cell-associated antigen can be the product of the cell's own gene expression, of a intracellular parasite, of a virus, or of another cell. In the a latter case the polypeptide antigen is subsequently associated with the cell which is involved in the pathological process.

The terms "T-lymphocyte" and "T-cell" will be used interchangeably for lymphocytes of thymic origin which are responsible for various cell mediated immune responses as well as for effector functions such as helper activity in the humoral immune response. Likewise, the terms "B-lymphocyte" and "B-cell" will be used interchangeably for antibody-producing lymphocytes.

An "antigen presenting cell" (APC) is a cell which presents epitopes to T-cells. Typical antigen-presenting cells are macrophages, dendritic cells and other phagocytizing and pinocytizing cells. It should be noted that B-cells also functions as APCs by presenting $T_H$ epitopes bound to MCH class II molecules to $T_H$ cells but when generally using the term APC in the present specification and claims it is intended to refer to the above-mentioned phagocytizing and pinocytizing cells.

"Helper T-lymphocytes" or "$T_H$ cells" denotes CD4 positive T-cells which provide help to B-cells and cytotoxic T-cells via the recognition of $T_H$ epitopes bound to MHC Class II molecules on antigen presenting cells.

The term "cytotoxic T-lymphocyte" (CTL) will be used for CD8 positive T-cells which require the assistance of $T_H$ cells in order to become activated.

A "specific" immune response is in the present context intended to denote a polyclonal immune response directed predominantly against a molecule or a group of quasi-identical molecules or, alternatively, against cells which present CTL epitopes of the molecule or the group of quasi-identical molecules.

A "weak or non-immunogenic polypeptide antigen" is herein intended to denote polypeptides having the amino acid sequence of the weak cell-associated protein antigens derived from the animal in question (e.g. a human), but also polypeptides having the amino acid sequence identical to analogues of such proteins isolated from other species are embraced by the term. Also forms of the polypeptides having differing glycosylation patterns because of their production in heterologous systems (e.g. yeasts or other non-mammalian eukaryotic expression systems or even prokaryotic systems) are included within the boundaries of the term. It should, however, be noted that when using the term, it is intended that the polypeptide in question is normally non-immunogenic or only weakly immunogenic in its natural localisation in the animal to be treated.

The term "polypeptide" is in the present context intended to mean both short peptides of from 2 to 10 amino acid residues, oligopeptides of from 11 to 100 amino acid residues, and polypeptides of more than 100 amino acid residues. Furthermore, the term is also intended to include proteins, i.e. functional biomolecules comprising at least one polypeptide; when comprising at least two polypeptides, these may form complexes, be covalently linked, or may be non-covalently linked. The polypeptide(s) in a protein can be glycosylated and/or lipidated and/or comprise prosthetic groups.

The term "subsequence" means any consecutive stretch of at least 3 amino acids or, when relevant, of at least 3 nucleotides, derived directly from a naturally occurring amino acid sequence or nucleic acid sequence, respectively.

The term "animal" is in the present context in general intended to denote an animal species (preferably mammalian), such as Homo sapiens, Canis domesticus, etc. and not just one single animal. However, the term also denotes a population of such an animal species, since it is important that the individuals immunized according to the method of the invention all harbour substantially the same weak, cell-associated polypeptide antigen allowing for immunization of the animals with the same immunogen(s). If, for instance, genetic variants of polypeptides exist in different human populations it may be necessary to use different immunogens in these different populations in order to be able to break the autotolerance towards the weak, cell-associated polypeptide antigen in each population.

By the term "down-regulation a cell-associated polypeptide antigen" is herein meant reduction in the living organism of the amount and/or activity of the antigen in question. The down-regulation can be obtained by means of several mechanisms: Of these, simple interference with the active site in the antigen by antibody binding is the most simple. However, it is also within the scope of the present invention that the antibody binding results in removal of the polypeptide by scavenger cells (such as macrophages and other phagocytizing cells), and even more important, that cells carrying or harbouring the antigen are killed by CTLs in the animal.

The expression "effecting simultaneous presentation by a suitable APC" is intended to denote that the animal's immune system is subjected to an immunogenic challenge in a controlled manner which results in the simultaneous presentation by APCs of the epitopes in question. As will appear from the disclosure below, such challenge of the immune system can be effected in a number of ways of which the most important are vaccination with polypeptide containing "pharmaccines" (i.e. a vaccine which is administered to treat or ameliorate ongoing disease) or nucleic acid "pharmaccine" vaccination. The important result to achieve is that immune competent cells in the animal are confronted with APCs displaying the relevant epitopes in an immunologically effective manner.

The term "immunogenically effective amount" has its usual meaning in the art, i.e. an amount of an immunogen which is capable of inducing an immune response which significantly engages pathogenic agents which share immunological features with the immunogen.

When using the expression that the weak cell-associated polypeptide antigens have been subjected to a "modification" is herein meant a chemical modification of the polypeptide which constitutes the backbone of the polypeptide in question. Such a modification can e.g. be derivatization (e.g. alkylation) of certain amino acid residues in the amino acid sequence, but as will be appreciated from the disclosure below, the preferred modifications comprise changes of the primary structure of the amino acid sequence.

When discussing "tolerance" and "autotolerance" is understood that since the polypeptides which are the targets of the present inventive method are self-proteins in the population to be vaccinated or proteins which do not result in induction of an effective immune response, normal individuals in the population do not mount an immune response against the polypeptide. It cannot be excluded, though, that occasional individuals in an animal population might be able to produce antibodies against the native polypeptide antigen, e.g. as part of a autoimmune disorder. At any rate, an animal will normally only be autotolerant towards its own polypeptide antigen, but it cannot be excluded that analogues derived from other animal species or from a population having a different phenotype would also be tolerated by said animal.

A "foreign T-cell epitope" is a peptide which is able to bind to an MHC molecule and stimulates T-cells in an animal species. Preferred foreign epitopes are "promiscuous" epitopes, i.e. epitopes which binds to a substantial fraction of MHC class II molecules in an animal species or population. Only a very limited number of such promiscuous T-cell epitopes are known, and they will be discussed in detail below. It should be noted that in order for the immunogens which are used according to the present invention to be effective in as large a fraction of an animal population as possible, it may be necessary to 1) insert several foreign T-cell epitopes in the same analogue or 2) prepare several analogues wherein each analogue has a different promiscuous epitope inserted. It should be noted that the concept of foreign T-cell epitopes also encompasses use of cryptic T-cell epitopes, i.e. epitopes which are derived from a self-protein and which only exerts immunogenic behaviour when existing in isolated form without being part of the self-protein in question.

A "foreign T helper lymphocyte epitope" (a foreign $T_H$ epitope) is a foreign T cell epitope which binds an MHC Class Class II molecule and can be presented on the surface of an antigen presenting cell (APC) bound to the MHC Class II molecule.

A "CTL" epitope is a peptide which is able to bind to an MHC class I molecule.

A "functional part" of a (bio)molecule is in the present context intended to mean the part of the molecule which is responsible for at least one of the biochemical or physiological effects exerted by the molecule. It is well-known in the art that many enzymes and other effector molecules have an active site which is responsible for the effects exerted by the molecule in question. Other parts of the molecule may serve a stabilizing or solubility enhancing purpose and can therefore be left out if these purposes are not of relevance in the context of a certain embodiment of the present invention. For instance it is possible to use certain cytokines as a modifying moiety in the analogue (cf. the detailed discussion below), and in such a case, the issue of stability may be irrelevant since the coupling to the analogue provides the stability necessary.

The term "adjuvant" has its usual meaning in the art of vaccine technology, i.e. a substance or a composition of matter which is 1) not in itself capable of mounting a specific immune response against the immunogen of the vaccine, but which is 2) nevertheless capable of enhancing the immune response against the immunogen. Or, in other words, vaccination with the adjuvant alone does not provide an immune response against the immunogen, vaccination with the immunogen may or may not give rise to an immune response against the immunogen, but the combined vaccination with immunogen and adjuvant induces an immune response against the immunogen which is stronger than that induced by the immunogen alone.

"Targeting" of a molecule is in the present context intended to denote the situation where a molecule upon introduction in the animal will appear preferentially in certain tissue(s) or will be preferentially associated with certain cells or cell types. The effect can be accomplished in a number of ways including formulation of the molecule in composition facilitating targeting or by introduction in the molecule of groups which facilitates targeting. These issues will be discussed in detail below.

"Stimulation of the immune system" means that a substance or composition of matter exhibits a general, non-specific immunostimulatory effect. A number of adjuvants and putative adjuvants (such as certain cytokines) share the ability to stimulate the immune system. The result of using an immunostimulating agent is an increased "alertness" of the immune system meaning that simultaneous or subsequent immunization with an immunogen induces a significantly more effective immune response compared to isolated use of the immunogen.

Preferred Embodiments

In order to induce a CTL response against a cell which presents epitopes derived from the polypeptide antigen on its surface, it is normally necessary that at least one CTL epitope, when presented, is associated with an MHC Class I molecule on the surface of the APC. Furthermore it is preferred that the at least one first foreign $T_H$ epitope, when presented, is associated with an MHC Class II molecule on the surface of the APC.

Preferred APCs presenting the epitopes are dendritic cells and macrophages, but any pino- or phagocytizing APC which is capable of simultaneously presenting 1) CTL epitopes bound to MHC class I molecules and 2) $T_H$ epitopes bound to MHC class II molecules, is a preferred APC according to the invention.

According to the invention, the cell-associated polypeptide antigen is preferably selected from a tumour-associated antigens and other self-proteins which are related to pathological processes but also viral antigens and antigens derived from an intracellular parasite or bacterium will. It is well-known in the art that such pathogen-associated antigens are often relatively poor immunogens (e.g. antigens from mycobacteria such as *Mycobacterium tuberculosis* and *Mycobacterium leprae*, but also from protozoans such as *Plasmodium* spp.). It is believed that the method of the invention, apart from rendering possible the production of antibody and CTL responses against true self-protein antigens, is capable of enhancing the often insufficient immune response mounted by the organism against such intracellular antigens.

Normally, it will be advantageous to confront the immune system with a large fraction of the amino acid sequence of the polypeptide antigen which is the vaccine target. Hence, in a preferred embodiment, presentation by the APC of the CTL epitope and the first foreign $T_H$ epitope is effected by presenting the animal's immune system with at least one first analogue of the cell-associated polypeptide antigen, said first analogue comprising a variation of the amino acid sequence of the cell-associated polypeptide antigen, said variation containing at least the CTL epitope and the first foreign $T_H$ epitope. This is in contrast to e.g. a DNA vaccination strategy where the CTL and $T_H$ epitopes are expressed by the same cell but as parts of separate polypeptides; such a DNA vaccination strategy is also an embodiment of the invention, but it is believed that having the two epitopes as part of the same polypeptide will normally enhance the immune response and, at any rate, the provision of only one expression product will be necessary.

In order to maximize the chances of mounting an effective immune response, it is preferred that the above-mentioned first analogue contains a substantial fraction of known and predicted CTL epitopes of the cell-associated polypeptide antigen, i.e. a fraction of the known and predicted CTL epitopes which binds a sufficient fractions of MHC Class I molecules in a population. For instance, it is preferred that the substantial fraction of known and predicted CTL epitopes in the amino acid sequence of the analogue are recognized by at least 50% of the MHC-I haplotypes recognizing all known and predicted CTL epitopes in the cell-associated polypeptide antigen, but higher percentages are preferred, such as at least 60, at least 70, at least 80, and at least 90%. Especially preferred is the use of analogues which preserves substantially all known CTL epitopes of the cell-associated polypeptide antigen are present in the analogue, i.e. close to 100% of the known CTL epitopes. Accordingly, it is also especially preferred that substantially all predicted CTL epitopes of the cell-associated polypeptide antigen are present in the at least first analogue.

Methods for predicting the presence of CTL epitopes are well-known in the art, cf. e.g. Rothbard et al. EMBO J. 7: 93–100 (1988).

As will be apparent from the present specification and claims it is expected that the inventive method described herein will render possible the effective induction of CTL responses against cell-associated polypeptide antigens.

In cases where the cell-associated polypeptide antigen is truly intracellular, the induction of a CTL response against cells harbouring the antigen is the only way to achieve its down-regulation by specific immunological means. However, in the case of membrane-associated antigens, it is advantageous to induce a antibody response against the weak, cell-associated polypeptide antigen. However, when raising a humoral immune response against a weak cell-associated antigen it is preferred to substantially restrict the antibody response to interaction with the parts of the antigen which are normally exposed to possible interaction with antibodies. Otherwise the result would most likely be the induction of an antibody response against parts of the antigen which is not normally engaging the humoral immune system, and this will in turn increase the risk of inducing cross-reactivity with antigens not related to any pathology. One elegant way of obtaining this restriction is to perform nucleic acid vaccination with an analogue of the weak cell-associated antigen, where the extracellular part thereof is either unaltered or includes a $T_H$ epitope which does not substantially alter the 3D structure of the extracellular part of the antigen. As one possible alternative, immunization can be performed with both a CTL directed immunogen and a B-cell directed immunogen where the B-cell directed immunogen is substantially incapable of effecting immunization against the intracellular part of the target antigen (the B-cell directed immunogen could e.g. lack any non-extracellular material from the antigen.

Induction of antibody responses can be achieved in a number of ways known to the person skilled in the art. For instance, the at least one first analogue may comprise a part consisting of a modification of the structure of the cell-associated polypeptide antigen, said modification having as a result that immunization of the animal with the first analogue induces production of antibodies in the animal against the cell-associated polypeptide antigen—this variant is as mentioned above especially suited for nucleic acid vaccination. Alternatively, the method of the invention can involve effecting presentation to the animal's immune system of an immunogenically effective amount of at least one second analogue of the cell-associated polypeptide antigen which contains such a modification. A convenient way to achieve that the modification has the desired antibody-inducing effect is to include at least one second foreign $T_H$ epitope in the second analogue, i.e. a strategy like the one used for the first analogue.

In the cases where it is desired to also mount an effective humoral immune response, it is advantageous that the first and/or second analogue(s) comprise(s) a substantial fraction of the cell-associated polypeptide antigen's B-cell epitopes, especially a substantial fraction of such B-cell epitopes which are extracellular in the naturally occurring form of the antigen in the pertinent animal.

The above-discussed variations and modifications of the weak, cell-associated polypeptide antigen can take different forms. It is preferred that the variation and/or modification involves amino acid substitution and/or deletion and/or insertion and/or addition. These fundamental operations relating to the manipulation of an amino acid sequence are intended to cover both single-amino acid changes as well as operations involving stretches of amino acids (i.a. shuffling of amino acid stretches within the polypeptide antigen; this is especially interesting when the antigen is a true intracellular antigen, since only considerations concerning preservation of CTL epitopes are relevant). It will be understood, that the introduction of e.g. one single amino acid insertion or deletion may give rise to the emergence of a foreign $T_H$ epitope in the sequence of the analogue, i.e. the emergence of an MHC Class II molecule binding sequence. However, in most situations it is preferable (and even necessary) to introduce a known foreign $T_H$ epitope, and such an operation will require acid substitution and/or insertion (or sometimes addition in the form of either conjugation to a carrier protein or provision of a fusion polypeptide by means of molecular biology methods. It is preferred that the number of amino acid insertions, deletions, substitutions or additions is at least 2, such as 3, 4, 5, 6, 7, 8, 9, 10, 11, 12, 13, 14, 15, 16, 17, 18, 19, 20, and 25 insertions, substitutions, additions or deletions. It is furthermore preferred that the number of amino acid substitutions is not in excess of 150, such as at most 100, at most 90, at most 80, and at most 70. It is especially preferred that the number of substitutions, insertions, deletions, or additions does not exceed 60, and in particular the number should not exceed 50 or even 40. Most preferred is a number of not more than 30.

Preferred embodiments of the invention includes modification by introducing at least one foreign immunodominant $T_H$ epitope. It will be understood that the question of immune dominance of a T-cell epitope depends on the animal species in question. As used herein, the term "immunodominance" simply refers to epitopes which in the vaccinated individual/population gives rise to a significant immune response, but it is a well-known fact that a T-cell epitope which is immunodominant in one individual is not necessarily immunodominant in another individual of the same species, even though it may be capable of binding MHC-II molecules in the latter individual. True immune dominant $T_H$ epitopes are those which, independent of the polypeptide wherein they form a subsequence, give rise to activation of $T_H$ cells—in other words, some $T_H$ epitopes have, as an intrinsic feature, the characteristic of substantially never being cryptic since they are substantially always processed by APCs and presented in the context of an MHC II molecule on the surface of the APC.

Another important point is the issue of MHC restriction of T-cell epitopes. In general, naturally occurring T-cell epitopes are MHC restricted, i.e. a certain peptides constituting a T-cell epitope will only bind effectively to a subset of MHC Class II molecules. This in turn has the effect that in most cases the use of one specific T-cell epitope will result in a vaccine component which is only effective in a fraction of the population, and depending on the size of that fraction, it can be necessary to include more T-cell epitopes in the same molecule, or alternatively prepare a multi-component vaccine wherein the components are variants of the antigen which are distinguished from each other by the nature of the T-cell epitope introduced.

If the MHC restriction of the T-cells used is completely unknown (for instance in a situation where the vaccinated animal has a poorly defined MHC composition), the fraction of the population covered by a specific vaccine composition can be determined by means of the following formula $$f_{population} = 1 - \prod_{i=1}^{n} (1 - p_i) \qquad \text{(II)}$$

where $p_i$ is the frequency in the population of responders to the $i^{th}$ foreign T-cell epitope present in the vaccine composition, and n is the total number of foreign T-cell epitopes in the vaccine composition. Thus, a vaccine composition containing 3 foreign T-cell epitopes having response frequencies in the population of 0.8, 0.7, and 0.6, respectively, would give

1−0.2H 0.3H 0.4=0.976 i.e. 97.6 percent of the population will statistically mount an MHC-II mediated response to the vaccine.

The above formula does not apply in situations where a more or less precise MHC restriction pattern of the peptides used is known. If, for instance a certain peptide only binds the human MHC-II molecules encoded by HLA-DR alleles DR1, DR3, DR5, and DR7, then the use of this peptide together with another peptide which binds the remaining MHC-II molecules encoded by HLA-DR alleles will accomplish 100% coverage in the population in question. Likewise, if the second peptide only binds DR3 and DR5, the addition of this peptide will not increase the coverage at all. If one bases the calculation of population response purely on MHC restriction of T-cell epitopes in the vaccine, the fraction of the population covered by a specific vaccine composition can be determined by means of the following formula:

$$f_{population} = 1 - \prod_{j=1}^{3} (1 - \phi_j)^2 \qquad \text{(III)}$$

wherein $N_j$ is the sum of frequencies in the population of allelic haplotypes encoding MHC molecules which bind any one of the T-cell epitopes in the vaccine and which belong to the $j^{th}$ of the 3 known HLA loci (DP, DR and DQ); in practice, it is first determined which MHC molecules will recognize each T-cell epitope in the vaccine and thereafter these are listed by type (DP, DR and DQ)—then, the individual frequencies of the different listed allelic haplotypes are summed for each type, thereby yielding $N_1$, $N_2$, and $N_3$.

It may occur that the value $p_i$ in formula II exceeds the corresponding theoretical value $B_i$:

$$\pi_i = 1 - \prod_{j=1}^{3} (1-v_j)^2 \qquad (IV)$$

wherein $A_j$ is the sum of frequencies in the population of allelic haplotype encoding MHC molecules which bind the $i^{th}$ T-cell epitope in the vaccine and which belong to the $j^{th}$ of the 3 known HLA loci (DP, DR and DQ). This means that in $1-B_i$ of the population is a frequency of responders of $f_{residual\_i}=(p_i-B_i)/(1-B_i)$. Therefore, formula III can be adjusted so as to yield formula V:

$$f_{population} = 1 - \prod_{j=1}^{3} (1 - \phi_j)^2 + \left(1 - \sum_{i=1}^{n} (1 - f_{\text{residual\_i}})\right) \tag{V}$$

where the term $1-f_{residual\text{-}i}$ is set to zero if negative. It should be noted that formula V requires that all epitopes have been haplotype mapped against identical sets of haplotypes.

Therefore, when selecting T-cell epitopes to be introduced in the analogue, it is important to include all knowledge of the epitopes which is available: 1) The frequency of responders in the population to each epitope, 2) MHC restriction data, and 3) frequency in the population of the relevant haplotypes.

There exist a number of naturally occurring "promiscuous" T-cell epitopes which are active in a large proportion of individuals of an animal species or an animal population and these are preferably introduced in the vaccine thereby reducing the need for a very large number of different analogues in the same vaccine.

The promiscuous epitope can according to the invention be a naturally occurring human T-cell epitope such as epitopes from tetanus toxoid (e.g. the P2 and P30 epitopes), diphtheria toxoid, Influenza virus hemagluttinin (HA), and *P. falciparum* CS antigen.

Over the years a number of other promiscuous T-cell epitopes have been identified. Especially peptides capable of binding a large proportion of HLA-DR molecules encoded by the different HLA-DR alleles have been identified and these are all possible T-cell epitopes to be introduced in analogues used according to the present invention. Cf. also the epitopes discussed in the following references which are hereby all incorporated by reference herein: WO 98/23635 (Frazer IH et al., assigned to The University of Queensland); Southwood S et. al, 1998, J. Immunol. 160: 3363–3373; Sinigaglia F et al., 1988, Nature 336: 778–780; Rammensee HG et al., 1995, Immunogenetics 41: 4 178–228; Chicz RM et al., 1993, J. Exp. Med 178: 27–47; Hammer J et al., 1993, Cell 74: 197–203; and Falk K et al., 1994, Immunogenetics 39: 230–242. The latter reference also deals with HLA-DQ and -DP ligands. All epitopes listed in these 5 references are relevant as candidate natural epitopes to be used in the present invention, as are epitopes which share common motifs with these.

Alternatively, the epitope can be any artificial T-cell epitope which is capable of binding a large proportion of haplotypes. In this context the pan DR epitope peptides ("PADRE") described in WO 95/07707 and in the corresponding paper Alexander J et al., 1994, Immunity 1: 751–761 (both disclosures are incorporated by reference herein) are interesting candidates for epitopes to be used according to the present invention. It should be noted that the most effective PADRE peptides disclosed in these papers carry D-amino acids in the C- and N-termini in order to improve stability when administered. However, the present invention primarily aims at incorporating the relevant epitopes as part of the modified antigen which should then subsequently be broken down enzymatically inside the lysosomal compartment of APCs to allow subsequent presentation in the context of an MHC-II molecule and therefore it is not expedient to incorporate D-amino acids in the epitopes used in the present invention.

One especially preferred PADRE, peptide is the one having the amino acid sequence AKFVAAWTLKAAA (SEQ ID NO: 40) or an immunologically effective subsequence thereof. This, and other epitopes having the same lack of MHC restriction are preferred T-cell epitopes which should be present in the analogues used in the inventive method. Such super-promiscuous epitopes will allow for the most simple embodiments of the invention wherein only one single analogue is presented to the vaccinated animal's immune system.

The nature of the above-discussed variation/modification preferably comprises that at least one first moiety is included in the first and/or second analogue(s), said first moiety effecting targeting of the analogue to an antigen presenting cell (APC), and/or at least one second moiety is included in the first and/or second analogue(s), said second moiety stimulating the immune system, and/or at least one third moiety is included in the first and/or second analogue(s), said third moiety optimizing presentation of the analogue to the immune system.

The functional and structural features relating these first, second and third moieties will be discussed in the following:

They can be present in the form of side groups attached covalently or non-covalently to suitable chemical groups in the amino acid sequence of the cell-associated polypeptide antigen or a subsequence thereof. This is to mean that stretches of amino acid residues derived from the polypeptide antigen are derivatized without altering the primary amino acid sequence, or at least without introducing changes in the peptide bonds between the individual amino acids in the chain.

The moieties can also be in the form of fusion partners to the amino acid sequence derived from the cell-associated polypeptide antigen. In this connection it should be mentioned that both possibilities include the option of conjugating the amino acid sequence to a carrier, cf. the discussion of these below. In other words, in the present context the term "fusion protein is not merely restricted to a fusion construct prepared by means of expression of a DNA fragment encoding the construct but also to a conjugate between two proteins which are joined by means of a peptide bond in a subsequent chemical reaction.

As mentioned above, the analogue can also include the introduction of a first moiety which targets the analogue to an APC or a B-lymphocyte. For instance, the first moiety can be a specific binding partner for a B-lymphocyte specific surface antigen or for an APC specific surface antigen. Many such specific surface antigens are known in the art. For instance, the moiety can be a carbohydrate for which there is a receptor on the B-lymphocyte or the APC (e.g. mannan or mannose). Alternatively, the second moiety can be a hapten. Also an antibody fragment which specifically recognizes a surface molecule on APCs or lymphocytes can be used as a first moiety (the surface molecule can e.g. be an FC(receptor of macrophages and monocytes, such as FC(RI or, alternatively any other specific surface marker such as CD40 or CTLA-4). It should be noted that all these exemplary targeting molecules can be used as part of an adjuvant, cf. below. CD40 ligand, antibodies against CD40, or variants thereof which bind CD40 will target the analogue to dendritic cells. At the same time, recent results have shown that the interaction with the CD40 molecule renders the $T_H$ cells unessential for obtaining a CTL response. Hence, it is contemplated that the general use of CD40 binding molecules as the first moiety (or as adjuvants, cf. below) will enhance the CTL response considerably; in fact, the use of such CD40 binding molecules as adjuvants and "first moieties" in the meaning of the present invention is believed to be inventive in its own right.

As an alternative or supplement to targeting the analogue to a certain cell type in order to achieve an enhanced immune response, it is possible to increase the level of responsiveness of the immune system by including the above-mentioned second moiety which stimulates the immune system. Typical examples of such second moieties are cytokines, heat-shock proteins, and hormones, as well as effective parts thereof.

Suitable cytokines to be used according to the invention are those which will normally also function as adjuvants in a vaccine composition, e.g. interferon ((IFN-( ), Flt3 ligand (Flt3L), interleukin 1 (IL-1), interleukin 2 (IL-2), interleukin 4 (IL-4), interleukin 6 (IL-6), interleukin 12 (IL-12), interleukin 13 (IL-13), interleukin 15 (IL-15), and granulocyte-macrophage colony stimulating factor (GM-CSF); alternatively, the functional part of the cytokine molecule may suffice as the second moiety. With respect to the use of such cytokines as adjuvant substances, cf. the discussion below.

Alternatively, the second moiety can be a toxin, such as listeriolycin (LLO), lipid A and heat-labile enterotoxin. Also, a number of mycobacterial derivatives such as MDP (muramyl dipeptide), CFA (complete Freund's adjuvant) and the trehalose diesters TDM and TDE are interesting possibilities.

According to the invention, suitable heat shock proteins used as the second moiety can be HSP70, HSP90, HSC70, GRP94, and calreticulin (CRT).

Also the possibility of introducing a third moiety which enhances the presentation of the analogue to the immune system is an important embodiment of the invention. The art has shown several examples of this principle. For instance, it is known that the palmitoyl lipidation anchor in the *Borrelia burgdorferi* protein OspA can be utilised so as to provide self-adjuvating polypeptides (cf. e.g. WO 96/40718). It seems that the lipidated proteins form up micelle-like structures with a core consisting of the lipidation anchor parts of the polypeptides and the remaining parts of the molecule protruding therefrom, resulting in multiple presentations of the antigenic determinants. Hence, the use of this and related approaches using different lipidation anchors (e.g. a myristyl group, a farnesyl group, a geranyl-geranyl group, a GPI-anchor, and an N-acyl diglyceride group) are preferred embodiments of the invention, especially since the provision of such a lipidation anchor in a recombinantly produced protein is fairly straightforward and merely requires use of e.g. a naturally occurring signal sequence as a fusion partner for the analogue. Another possibility is use of the C3d fragment of complement factor C3 or C3 itself (cf. Dempsey et al., 1996, Science 271, 348–350 and Lou & Kohler, 1998, Nature Biotechnology 16, 458–462).

It is important to note that when attempting to use the method of the invention against e.g. membrane bound polypeptide antigens which are exposed to the extracellular compartment, it is most preferred that the first and/or second analogue(s) has/have substantially the overall tertiary structure of the cell-associated polypeptide antigen. In the present specification and claims this is intended to mean that the overall tertiary structure of the part of the polypeptide antigen which is extracellularly exposed is preserved, since, as mentioned above, the tertiary structure of the obligate intracellular polypeptides do not engage the humeral immune system. In fact, as part of the vaccination strategy it is often desired to avoid exposure to the extracellular compartment of putative B-cell epitopes derived from intracellular part of the polypeptide antigens; in this way, potentially adverse effects caused by cross-reactivity with other antigens can be minimized.

For the purposes of the present invention, it is however sufficient if the variation/modification (be it an insertion, addition, deletion or substitution) gives rise to a foreign T-cell epitope and at the same time preserves a substantial number of the CTL epitopes in the polypeptide antigen (and sometimes also a substantial number of B-cell epitopes).

The following formula describes the constructs generally covered by the invention:

$$(MOD_1)_{s1}(PAG_{e1})_{n1}(MOD_2)_{s2}(PAG_{e2})_{n2} \ldots (MOD_x)_{sx}(PAG_{ex})_{nx} \qquad (I)$$

where $PAG_{e1}$–$PAG_{ex}$ are x CTL and/or B-Cell epitope containing subsequences of the relevant polypeptide antigen which independently are identical or non-identical and which may contain or not contain foreign side groups, x is an integer ∃ 3, n1–nx are x integers ∃ 0 (at least one is ∃ 1), $MOD_1$–$MOD_x$ are x modifications introduced between the preserved epitopes, and s1–sx are x integers ∃ 0 (at least one is ∃ 1 if no side groups are introduced in the sequences). Thus, given the general functional restraints on the immunogenicity of the constructs, the invention allows for all kinds of permutations of the original antigen sequence, and all kinds of modifications therein. Thus, included in the invention are analogues obtained by omission of parts of the polypeptide antigen sequence which e.g. exhibit adverse effects in vivo or omission of parts which are normally intracellular and thus could give rise to undesired immunological reactions, cf. the detailed discussion below.

A further elaboration of the above principle include use of CTL and/or B-cell epitopes from more than one pathology-related antigen. For instance, there are several cancer related antigens that exert their oncogenic effects when they are in a mutated form only—examples are mutated K-ras and P53 which both are crucial proteins in normal cell cycle regulation and which both are expression products in most normal cells. In some cases, CTLs have been shown to recognise mutated peptides from these antigens. It is therefore important that the immune system responds to te mutated peptide only, and not to the unmutated parts, if antigen specific immunotherapy is instigated.

We have devised a strategy whereby sequences of 8–25 amino acids of such disease-related proteins could be used as further epitopes in an AutoVac construct—in preferred embodiments, the introduced epitopes would at the same time provide for the emergence of $T_H$ epitopes in the final construct, cf. the discussion above. The epitopes used for this purpose would be those which comprise the mutated region of the disease-related protein. By using such an approach, it would be possible to generate CTLs (and possibly antibodies, where applicable) against only the mutated form of the disease-related antigen. In the cases where the disease-related antigen provides for the emergence of a $T_H$ epitope, the use of a truly foreign $T_H$ epitope could be completely omitted. An embodiment of this principle could e.g. be vaccination with a nucleic acid vaccine which encode an analogue of a polypeptide antigen (e.g. Her2 or PSM) wherein has been introduced at least one $T_H$ epitope and at least one peptide derived from another disease-related antigen (e.g. a peptide from the mutated part of an oncogenic protein). In a preferred embodiment, the at least one $T_H$ epitope is introduced as a consequence of the introduction of the peptide.

It is furthermore preferred that the variation and/or modification includes duplication, when applicable, of the at least one B-cell epitope, or of at least one CTL epitope of the cell-associated polypeptide antigen. This strategy will give the result that multiple copies of preferred epitopic regions are presented to the immune system and thus maximizing the probability of an effective immune response. Hence, this embodiment of the invention utilises multiple presentations of epitopes derived from the polypeptide antigen (i.e. formula I wherein at least one B-cell epitope is present in two positions).

This effect can be achieved in various ways, e.g. by simply preparing fusion polypeptides comprising the structure $(PAG)_m$, where m is an integer ∃ 2 and then introduce the modifications discussed herein in at least one of the polypeptide antigen sequences.

An alternative embodiment of the invention which also results in the preferred presentation of multiple (e.g. at least 2) copies of the important epitopic regions of the antigen to the immune system is the covalent coupling of the antigen, subsequence or variants thereof to certain molecules. For instance, polymers can be used, e.g. carbohydrates such as dextran, cf. e.g. Lees A et al., 1994, Vaccine 12: 1160–1166; Lees A et al., 1990, J. Immunol. 145: 3594–3600, but also mannose and mannan are useful alternatives. Integral membrane proteins from e.g. *E. coli* and other bacteria are also useful conjugation partners. The traditional carrier molecules such as keyhole limpet haemocyanin (KLH), tetanus toxoid, diphtheria toxoid, and bovine serum albumin (BSA) are also preferred and useful conjugation partners.

Maintenance of the sometimes advantageous substantial fraction of B-cell epitopes or even the overall tertiary structure of a protein which is subjected to modification as described herein can be achieved in several ways. One is simply to prepare a polyclonal antiserum directed against the polypeptide antigen (e.g. an antiserum prepared in a rabbit) and thereafter use this antiserum as a test reagent (e.g. in a competitive ELISA) against the modified proteins which are produced. Modified versions (analogues) which react to the same extent with the antiserum as does the polypeptide antigen must be regarded as having the same overall tertiary structure as the polypeptide antigen whereas analogues exhibiting a limited (but still significant and specific) reactivity with such an antiserum are regarded as having maintained a substantial fraction of the original B-cell epitopes.

Alternatively, a selection of monoclonal antibodies reactive with distinct epitopes on the polypeptide antigen can be prepared and used as a test panel. This approach has the advantage of allowing 1) an epitope mapping of the polypeptide antigen in question and 2) a mapping of the epitopes which are maintained in the analogues prepared.

Of course, a third approach would be to resolve the 3-dimensional structure of the polypeptide antigen or of a biologically active truncate thereof (cf. above) and compare this to the resolved three-dimensional structure of the analogues prepared. Three-dimensional structure can be resolved by the aid of X-ray diffraction studies and NMR-spectroscopy. Further information relating to the tertiary structure can to some extent be obtained from circular dichroism studies which have the advantage of merely requiring the polypeptide in pure form (whereas X-ray diffraction requires the provision of crystallized polypeptide and NMR requires the provision of isotopic variants of the polypeptide) in order to provide useful information about the tertiary structure of a given molecule. However, ultimately X-ray diffraction and/or NMR are necessary to obtain conclusive data since circular dichroism can only provide indirect evidence of correct 3-dimensional structure via information of secondary structure elements.

In essence there are at present three feasible ways of obtaining the presentation of the relevant epitopes to the immune system: Traditional sub-unit vaccination with polypeptide antigens, administration of a genetically modified live vaccine, and nucleic acid vaccination. These three possibilities will be discussed separately in the following:

Polypeptide Vaccination

This entails administration to the animal in question of an immunogenically effective amount of the at least one first analogue, and, when relevant, administration of an immunologically effective amount of the at least one second analogue. Preferably, the at least one first and/or second analogue(s) is/are formulated together with a pharmaceutically and immunologically acceptable carrier and/or vehicle and, optionally an adjuvant.

When effecting presentation of the analogue to an animal's immune system by means of administration thereof to the animal, the formulation of the polypeptide follows the principles generally acknowledged in the art.

Preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables either as liquid solutions or suspensions; solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccines; cf. the detailed discussion of adjuvants below.

The vaccines are conventionally administered parenterally, by injection, for example, either subcutaneously, intradermally, subdermally or intramuscularly. Additional formulations which are suitable for other modes of administration include suppositories and, in some cases, oral, buccal, sublinqual, intraperitoneal, intravaginal, anal and intracranial formulations. For suppositories, traditional binders and carriers may include, for example, polyalkalene glycols or triglycerides; such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10–95% of active ingredient, preferably 25–70%. For oral formulations, cholera toxin is an interesting formulation partner (and also a possible conjugation partner). The polypeptides may be formulated into the vaccine as neutral or salt forms. Pharmaceutically acceptable salts include acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1:g to 2000:g (even though higher amounts in the 1–10 mg range are contemplated), such as in the range from about 0.5:g to 1000:g, preferably in the range from 1:g to 500:g and especially in the range from about 10:g to 100:g. Suitable regimens for initial administration and booster shots are also variable but are typified by an initial administration followed by subsequent inoculations or other administrations.

The manner of application may be varied widely. Any of the conventional methods for administration of a vaccine are applicable. These include oral application on a solid physiologically acceptable base or in a physiologically acceptable dispersion, parenterally, by injection or the like. The dosage of the vaccine will depend on the route of administration and will vary according to the age of the person to be vaccinated and the formulation of the antigen.

Some of the polypeptides of the vaccine are sufficiently immunogenic in a vaccine, but for some of the others the immune response will be enhanced if the vaccine further comprises an adjuvant substance. It is especially preferred to use an adjuvant which can be demonstrated to facilitate breaking of the autotolerance to autoantigens.

Various methods of achieving adjuvant effect for the vaccine are known. General principles and methods are detailed in "The Theory and Practical Application of Adjuvants", 1995, Duncan E.S. Stewart-Tull (ed.), John Wiley & Sons Ltd, ISBN 0-471-95170-6, and also in "Vaccines: New Generationn Immunological Adjuvants", 1995, Gregoriadis G et al. (eds.), Plenum Press, New York, ISBN 0-306-45283-9, both of which are hereby incorporated by reference herein.

Preferred adjuvants facilitate uptake of the vaccine molecules by APCs, such as dendritic cells, and activate these. Non-limiting examples are selected from the group consisting of an immune targeting adjuvant; an immune modulating adjuvant such as a toxin, a cytokine, and a mycobacterial derivative; an oil formulation; a polymer; a micelle forming adjuvant; a saponin; an immunostimulating complex matrix (ISCOM matrix); a particle; DDA; aluminium adjuvants; DNA adjuvants; (-inulin; and an encapsulating adjuvant. In general it should be noted that the disclosures above which relate to compounds and agents useful as first, second and third moieties in the analogues also refer mutatis mutandis to their use in the adjuvant of a vaccine of the invention.

The application of adjuvants include use of agents such as aluminum hydroxide or phosphate (alum), commonly used as 0.05 to 0.1 percent solution in buffered saline, admixture with synthetic polymers of sugars (e.g. Carbopol®) used as 0.25 percent solution, aggregation of the protein in the vaccine by heat treatment with temperatures ranging between 70E to 101EC for 30 second to 2 minute periods respectively and also aggregation by means of cross-linking agents are possible. Aggregation by reactivation with pepsin treated antibodies (Fab fragments) to albumin, mixture with bacterial cells such as C. parvum or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. Admixture with oils such as squalene and IFA is also preferred.

According to the invention DDA (dimethyldioctadecylammonium bromide) is an interesting candidate for an adjuvant as is DNA and (-inulin, but also Freund's complete and incomplete adjuvants as well as quillaja saponins such as QuilA and QS21 are interesting. Further possibilities are monophosphoryl lipid A (MPL), and the above mentioned C3 and C3d.

Liposome formulations are also known to confer adjuvant effects, and therefore liposome adjuvants are preferred according to the invention.

Also immunostimulating complex matrix type (ISCOM® matrix) adjuvants are preferred choices according to the invention, especially since it has been shown that this type of adjuvants are capable of up-regulating MHC Class II expression by APCs. An ISCOM® matrix consists of (optionally fractionated) saponins (triterpenoids) from Quillaja saponaria, cholesterol, and phospholipid. When admixed with the immunogenic protein, the resulting particulate formulation is what is known as an ISCOM particle where the saponin constitutes 60–70% w/w, the cholesterol and phospholipid 10–15% w/w, and the protein 10–15% w/w. Details relating to composition and use of immunostimulating complexes can e.g. be found in the above-mentioned text-books dealing with adjuvants, but also Morein B et al., 1995, Clin. Immunother. 3: 461–475 as well as Barr IG and Mitchell GF, 1996, Immunol. and Cell Biol. 74: 8–25 (both incorporated by reference herein) provide useful instructions for the preparation of complete immunostimulating complexes.

Another highly interesting (and thus, preferred) possibility of achieving adjuvant effect is to employ the technique described in Gosselin et al., 1992 (which is hereby incorporated by reference herein). In brief, the presentation of a relevant antigen such as an antigen of the present invention can be enhanced by conjugating the antigen to antibodies (or antigen binding antibody fragments) against the Fc(receptors on monocytes/macrophages. Especially conjugates between antigen and anti-Fc(RI have been demonstrated to enhance immunogenicity for the purposes of vaccination.

Other possibilities involve the use of the targeting and immune modulating substances (i.a. cytokines) mentioned above as candidates for the first and second moieties in the modified analogues. In this connection, also synthetic inducers of cytokines like poly I:C are possibilities.

Suitable mycobacterial derivatives are selected from the group consisting of muramyl dipeptide, complete Freund's adjuvant, RIBI, and a diester of trehalose such as TDM and TDE.

Suitable immune targeting adjuvants are selected from the group consisting of CD40 ligand and CD40 antibodies or specifically binding fragments thereof (cf. the discussion above), mannose, a Fab fragment, and CTLA-4.

Suitable polymer adjuvants are selected from the group consisting of a carbohydrate such as dextran, PEG, starch, mannan, and mannose; a plastic polymer; and latex such as latex beads.

Yet another interesting way of modulating an immune response is to include the immunogen (optionally together with adjuvants and pharmaceutically acceptable carriers and vehicles) in a "virtual lymph node" (VLN) (a proprietary medical device developed by ImmunoTherapy, Inc., 360 Lexington Avenue, New York, N.Y. 10017–6501). The VLN (a thin tubular device) mimics the structrue and function of a lymph node.

Insertion of a VLN under the skin creates a site of sterile inflammation with an upsurge of cytokines and chemokines. T- and B-cells as well as APCs rapidly respond to the danger signals, home to the inflamed site and accumulate inside the porous matrix of the VLN. It has been shown that the necessary antigen dose required to mount an immune response to an antigen is reduced when using the VLN and that immune protection conferred by vaccination using a VLN surpassed conventional immunization using Ribi as an adjuvant. The technology is i.a. described briefly in Gelber C et al., 1998, "Elicitation of Robust Cellular and Humoral Immune Responses to Small Amounts of Immunogens Using a Novel Medical Device Designated the Virtual Lymph Node", in: "From the Laboratory to the Clinic, Book of Abstracts, Oct. $12^{th}$–$15^{th}$ $^{1998}$, Seascape Resort, Aptos, Calif.".

Recent findings have demonstrated that the co-administration of H2 agonists enhances the in-tumour survival of Natural Killer Cells and CTLs. Hence, it is also contemplated to include H2 agonists as adjuvants in the methods of the invention.

It is expected that the vaccine should be administered at least once a year, such as at least 1, 2, 3, 4, 5, 6, and 12 times a year. More specifically, 1–12 times per year is expected, such as 1, 2, 3, 4, 5, 6, 7, 8, 9, 10, 11, or 12 times a year to an individual in need thereof. It has previously been shown that the memory immunity induced by the use of the preferred autovaccines according to the invention is not permanent, and therefor the immune system needs to be periodically challenged with the analogues.

Due to genetic variation, different individuals may react with immune responses of varying strength to the same polypeptide. Therefore, the vaccine according to the invention may comprise several different polypeptides in order to increase the immune response, cf. also the discussion above concerning the choice of foreign T-cell epitope introductions. The vaccine may comprise two or more polypeptides, where all of the polypeptides are as defined above.

The vaccine may consequently comprise 3–20 different modified or unmodified polypeptides, such as 3–10 different polypeptides. However, normally the number of peptides will be sought kept to a minimum such as 1 or 2 peptides.

Live Vaccines

The second alternative for effecting presentation to the immune system is the use of live vaccine technology. In live vaccination, presentation to the immune system is effected by administering, to the animal, a non-pathogenic microorganism which has been transformed with a nucleic acid fragment encoding the necessary epitopic regions or a complete $1^{st}$ and/or $2^{nd}$ analogue. Alternatively, the microorganism is transformed with a vector incorporating such a nucleic acid fragment. The non-pathogenic microorganism can be any suitable attenuated bacterial strain (attenuated by means of passaging or by means of removal of pathogenic expression products by recombinant DNA technology), e.g. *Mycobacterium bovis* BCG., non-pathogenic *Streptococcus* spp., *E. coli, Salmonella* spp., *Vibrio cholerae, Shigella*, etc. Reviews dealing with preparation of state-of-the-art live vaccines can e.g. be found in Saliou P, 1995, Rev. Prat. 45: 1492–1496 and Walker PD, 1992, Vaccine 10: 977–990, both incorporated by reference herein. For details about the nucleic acid fragments and vectors used in such live vaccines, cf. the discussion below.

As for the polypeptide vaccine, the $T_H$ epitope and/or the first and/or second and/or third moieties can, if present, be in the form of fusion partners to the amino acid sequence derived from the cell-associated polypeptide antigen.

As an alternative to bacterial live vaccines, the nucleic acid fragment of the invention discussed below can be incorporated in a non-virulent viral vaccine vector. One possibility is a pox virus such as vaccinia, MVA (modified Vaccina virus), canary pox, avi-pox, and chicken pox etc. Alternatively, a herpes simplex virus variant can be used.

Normally, the non-pathogenic microorganism or virus is administered only once to the animal, but in certain cases it may be necessary to administer the microorganism more than once in a lifetime.

Also, the microorganism can be transformed with nucleic acid(s) containing regions encoding the $1^{st}$, $2^{nd}$ and/or $3^{rd}$ moieties, e.g. in the form of the immunomodulating substances described above such as the cytokines discussed as useful adjuvants. A preferred version of this embodiment encompasses having the coding region for the analogue and the coding region for the immunomodulator in different open reading frames or at least under the control of different promoters. Thereby it is avoided that the analogue or epitopes are produced as fusion partners to the immunomodulator. Alternatively, two distinct nucleotide fragments can be used as transforming agents.

Nucleic Acid Vaccination

As an alternative to classic administration of a peptide-based vaccine, the technology of nucleic acid vaccination (also known as "nucleic acid immunisation", "genetic immunisation", "gene immunisation" and "DNA vaccination") offers a number of attractive features.

First, in contrast to the traditional vaccine approach, nucleic acid vaccination does not require resource consuming large-scale production of the immunogenic agent (e.g. in the form of industrial scale fermentation of microorganisms producing the analogues necessary in polypeptide vaccination). Furthermore, there is no need to device purification and refolding schemes for the immunogen. And finally, since nucleic acid vaccination relies on the biochemical apparatus of the vaccinated individual in order to produce the expression product of the nucleic acid introduced, the optimum posttranslational processing of the expression product is expected to occur; this is especially important in the case of autovaccination, since, as mentioned above, a significant fraction of the original B-cell epitopes should be preserved in the analogues derived from extracellularly exposed polypeptide sequences, and since B-cell epitopes in principle can be constituted by parts of any (bio)molecule (e.g.

carbohydrate, lipid, protein etc.). Therefore, native glycosylation and lipidation patterns of the immunogen may very well be of importance for the overall immunogenicity and this is best ensured by having the host producing the immunogen.

Hence, an important embodiment of the method of the invention involves that presentation is effected by in vivo introducing, into the APC, at least one nucleic acid fragment which encodes and expresses the at least one CTL epitope and/or the at least one B-cell epitope, and the at least one first foreign $T_H$ epitope (an alternative encompasses administration of at least 2 distinct nucleic acid fragments, where one encodes the at least one CTL epitope and the other encodes the at least one foreign $T_H$ epitope). Preferably, this is done by using a nucleic acid fragment which encodes and expresses the above-discussed first analogue. If the first analogue is equipped with the above-detailed $T_H$ epitopes and/or first and/or second and/or third moieties, these are then present in the form of fusion partners to the amino acid sequence derived from the cell-associated polypeptide antigen, the fusion construct being encoded by the nucleic acid fragment.

As for the traditional vaccination approach, the nucleic acid vaccination can be combined with in vivo introduction, into the APC, of at least one nucleic acid fragment encoding and expressing the second analogue. The considerations pertaining to $1^{st}$, $2^{nd}$ and $3^{rd}$ moieties and $T_H$ epitopes apply also here.

In this embodiment, the introduced nucleic acid is preferably DNA which can be in the form of naked DNA, DNA formulated with charged or uncharged lipids, DNA formulated in liposomes, DNA included in a viral vector, DNA formulated with a transfection-facilitating protein or polypeptide, DNA formulated with a targeting protein or polypeptide, DNA formulated with Calcium precipitating agents, DNA coupled to an inert carrier molecule, and DNA formulated with an adjuvant. In this context it is noted that practically all considerations pertaining to the use of adjuvants in traditional vaccine formulation apply for the formulation of DNA vaccines. Hence, all disclosures herein which relate to use of adjuvants in the context of polypeptide based vaccines apply mutatis mutandis to their use in nucleic acid vaccination technology. The same holds true for other considerations relating to formulation and mode and route of administration and, hence, also these considerations discussed above in connection with a traditional vaccine apply mutatis mutandis to their use in nucleic acid vaccination technology.

One especially preferred type of formulation of nucleic acid vaccines are microparticles containing the DNA. Suitable microparticles are e.g. described in WO 98/31398.

Furthermore, the nucleic acid(s) used as an immunization agent can contain regions encoding the $1^{st}$, $2^{nd}$ and/or $3^{rd}$ moieties, e.g. in the form of the immunomodulating substances described above such as the cytokines discussed as useful adjuvants. A preferred version of this embodiment encompasses having the coding region for the analogue and the coding region for the immunomodulator in different open reading frames or at least under the control of different promoters. Thereby it is avoided that the analogue or epitope is produced as a fusion partner to the immunomodulator. Alternatively, two distinct nucleotide fragments can be used, but this is less preferred because of the advantage of ensured co-expression when having both coding regions included in the same molecule.

Under normal circumstances, the nucleic acid of the vaccine is introduced in the form of a vector wherein expression is under control of a viral promoter. For more detailed discussions of vectors according to the invention, cf. the discussion below. Also, detailed disclosures relating to the formulation and use of nucleic acid vaccines are available, cf. Donnelly JJ et al, 1997, Annu. Rev. Immunol. 15: 617–648 and Donnelly JJ et al., 1997, Life Sciences 60: 163–172. Both of these references are incorporated by reference herein.

An important part of the invention pertains to a novel method for selecting an appropriate immunogenic analogue of a cell-associated polypeptide antigen which is weakly immunogenic or non-immunogenic in an animal, said immunogenic analogue being capable of inducing a CTL response in the animal against cells displaying an MHC Class I molecule bound to an epitope derived from the cell-associated polypeptide antigen. This method comprises the steps of a) identifying at least one subsequence of the amino acid sequence of the cell-associated polypeptide antigen, where said subsequence does not contain known or predicted CTL epitopes, b) preparing at least one putatively immunogenic analogue of the cell-associated polypeptide antigen by introducing, in the amino acid sequence of the cell-associated polypeptide antigen, at least one $T_H$ epitope foreign to the animal in a position within the at least one subsequence identified in step a), and c) selecting the/those analogues prepared in step b) which are verifiably capable of inducing a CTL response in the animal.

Alternatively, the above selection method involves the preparation of a nucleic acid fragment for nucleic acid vaccination purposes. In that situation, it is required that the encoded peptide includes at least one $T_H$ epitope.

When the analogue is derived from an antigen which is exposed to the extracellular phase, it is preferred that the subsequence identified in step a) further does not contain cysteine residues, or, alternatively, that the $T_H$ epitope introduced in step b) does not substantially alter the pattern of cysteine residues. This approach facilitates the preservation of spatial B-cell epitopes in the resulting construct which are similar to the B-cell epitopes in the weak, cell-associated polypeptide antigen.

For the same reasons it is preferred that the subsequence identified in step a) further does not contain known or predicted glycosylation sites, or, alternatively, wherein the $T_H$ epitope introduced in step b) does not substantially alter the glycosylation pattern.

Certain of the weak, cell-associated polypeptide antigens exert undesired effects by having a pathophysiological role. It is desired that these effects are not exerted by the vaccination constructs, and therefore it is preferred that the subsequence identified in step a) contributes significantly to a pathophysiological effect exerted by the cell-associated polypeptide antigen, and that the introduction in step b) of the foreign $T_H$ epitope reduces or abolishes said pathophysiological effect. An example of this approach is to remove the active site in an enzyme, hormone or cytokine and exchange this with the foreign $T_H$ epitope.

Another important consideration pertains to the question of immunological cross-reactivity of the vaccine's polypeptide product with other self-proteins which are not related to a pathology. Such cross-reactivity should preferably be avoided and hence an important embodiment of this method of the invention is one where the subsequence identified in step a) is homologous to an amino acid sequence of a different protein antigen of the animal, and where the introduction of the $T_H$ epitope in step b) substantially removes the homology.

Related to this embodiment is an embodiment where any amino acid sequences which 1) are not normally exposed to the extracellular phase and 2) which may constitute B-cell epitopes of the weak, cell-associated polypeptide antigen, are not preserved in the analogue. This can be achieved by exchanging such amino acid sequences with $T_H$ epitopes which do not constitute B-cell epitopes, by completely removing them, or by partly removing them.

On the other hand, it is preferred that any "true" B-cell epitopes of the weak cell-associated polypeptide antigen are preserved to a high degree, and therefore an important embodiment of the selection method of the invention involves that the introduction in step b) of the foreign $T_H$ epitope results in preservation of a substantial fraction of B-cell epitopes of the cell-associated polypeptide antigen. It is especially preferred that the analogue preserves the overall tertiary structure of the cell-associated polypeptide antigen.

The preparation in step b) is preferably accomplished by molecular biological means or by means of solid or liquid phase peptide synthesis. Shorter peptides are preferably prepared by means of the well-known techniques of solid- or liquid-phase peptide synthesis. However, recent advances in this technology has rendered possible the production of full-length polypeptides and proteins by these means, and therefore it is also within the scope of the present invention to prepare the long constructs by synthetic means.

After having identified the useful analogues according to the above-discussed method, it is necessary to produce the analogue in larger scale. The polypeptides are prepared according to methods well-known in the art.

This can be done by molecular biological means comprising a first step of preparing a transformed cell by introducing, into a vector, a nucleic acid sequence encoding an analogue which has been selected according to the method and transforming a suitable host cell with the vector. The next step is to culture the transformed cell under conditions facilitating the expression of the nucleic acid fragment encoding the analogue of the cell-associated antigen, and subsequently recovering the analogue from the culture supernatant or directly from the cells, e.g. in the form of a lysate). Alternatively, the analogue can be prepared by large-scale solid or liquid phase peptide synthesis, cf. above.

Finally, the product can, depending on the cell chosen as a host cell or the synthesis method used, be subjected to artificial post-translational modifications. These can be refolding schemes known in the art, treatment with enzymes (in order to obtain glycosylation or removal of undesired fusion partners, chemical modifications (again glycosylation is a possibility), and conjugation, e.g. to traditionally carrier molecules.

It should be noted that preferred analogues of the invention (and also the relevant analogues used in the methods of the invention) comprise modifications which results in a polypeptide having a sequence identity of at least 70% with the polypeptide antigen or with a subsequence thereof of at least 10 amino acids in length. Higher sequence identities are preferred, e.g. at least 75% or even at least 80% or 85%. The sequence identity for proteins and nucleic acids can be calculated as $(N_{ref}-N_{dif})A100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}$=2 and $N_{ref}$=8).

Specific Exemplary Targets for the Method of the Invention

As discussed above, preferred weak, cell-associated polypeptide antigens are tumour-associated antigens. A non-limiting list of these are given in the following table.

| Antigen | Reference |
|---|---|
| 5 alpha reductase | Délos S, Carsol J L, Fina F, Raynaud J P, Martin P M. 5alpha-reductase and 17beta-hydroxysteroid dehydrogenase expression in epithelial cells from hyperplastic and malignant human prostate. Int J Cancer Mar. 16, 1998 75:6 840–6 |
| ∀-fetoprotein | Esteban C, Terrier P, Frayssinet C, Uriel J. Expression of the alpha-fetoprotein gene in human breast cancer. Tumour Biol 1996 17:5 299–305 |
| AM-1 | Harada Y, Ohuchi N, Masuko T, Funaki Y, Mori S, Satomi S, Hashimoto Y. Characterization of a new breast cancer-associated antigen and its relationship to MUC1 and TAG-72 antigens. Tohoku J Exp Med November 1996 180:3 273–88 |
| APC | Dihlmann S, Amler L C, Schwab M, Wenzel A. Variations in the expression of the adenomatous polyposis coli (APC) tumor suppressor gene in human cancer cell lines of different tissue origin. Oncol Res 1997 9:3 119–27 |
| APRIL | LE, Sordat B, Rimoldi D, Tschopp J. APRIL, a new ligand of the tumor necrosis factor family, stimulates tumor cell growth. J Exp Med Sep. 21, 1998 188:6 1185–90 |
| BAGE | Böel P, Wildmann C, Sensi M L, Brasseur R, Renauld J-C, Coulie P, Boon T, and Van der Bruggen P. BAGE: a new gene encoding an antigen recognized on human melanomas by cytolytic lymphocytes. Immunity 1995, 2: 167–175. |
| ∃-catenin | Hugh T J, Dillon S A, O'Dowd G, Getty B, Pignatelli M, Poston G J, Kinsella A R. beta-catenin expression in primary and metastatic colorectal carcinoma. Int J Cancer Aug. 12, 1999 82:4 504–11 |
| Bc12 | Koty P P, Zhang H, Levitt M L. Antisense bcl-2 treatment increases programmed cell death in non-small cell lung cancer cell lines. Lung Cancer February 1999 23:2 115–27 |
| bcr-abl (b3a2) | Verfaillie C M, Bhatia R, Miller W, Mortari F, Roy V, Burger S, McCullough J, Stieglbauer K, Dewald G, Heimfeld S, Miller J S, McGlave P B. BCR/ABL-negative primitive progenitors suitable for transplantation can be selected from the marrow of most early-chronic phase but not accelerated-phase chronic myelogenous leukemia patients. Blood Jun. 1, 1996 87:11 4770–9 |
| CA-125 | Bast R C Jr, Xu F J, Yu Y H, Barnhill S, Zhang Z, Mills G B. CA 125: the past and the future. Int J Biol Markers October–December 1998 13:4 179–87 |
| CASP-8/FLICE | Mandruzzato S, Brasseur F, Andry G, Boon T, van der Bruggen P., A CASP-8 mutation recognized by cytolytic T lymphocytes on a human head and neck carcinoma. J Exp Med Aug. 29, 1997 186:5 785–93. |
| Cathepsins | Thomssen C, Schmitt M, Goretzki L, Oppelt P, Pache L, Dettmar F, Jänicke F, Graeff H. Prognostic value of the cysteine proteases cathepsins B and cathepsin L in human breast cancer. Clin Cancer Res July 1995 1:7 741–6 |
| CD19 | Scheuermann R H, Racila E. CD19 antigen in leukemia and lymphoma diagnosis and immunotherapy. Leuk Lymphoma August 1995 18:5–6 385–97 |
| CD20 | Knox S J, Goris M L, Trisler K, Negrin R, Davis T, Liles T M, Grillo-López A, Chinn P, Varns C, Ning S C, Fowler S, Deb N, Becker M, Marquez C, Levy R. Yttrium-90-labeled anti-CD20 monoclonal antibody therapy of recurrent B-cell lymphoma. Clin Cancer Res March 1996 2:3 457–70 |

-continued

| Antigen | Reference |
|---|---|
| CD21 | Shubinsky G, Schlesinger M, Polliack A, Rabinowitz R. Pathways controlling the expression of surface CD21 (CR2) and CD23 (Fc(epsilon)IIR) proteins in human malignant B cells. Leuk Lymphoma May 1997 25:5–6 521–30 |
| CD23 | Shubinsky G, Schlesinger M, Polliack A, Rabinowitz R. Pathways controlling the expression of surface CD21 (CR2) and CD23 (Fc(epsilon)IIR) proteins in human malignant B cells. Leuk Lymphoma May 1997 25:5–6 521–30 |
| CD22 | French R R, Penney C A, Browning A C, Stirpe F, George A J, Glennie M J. Delivery of the ribosome-inactivating protein, gelonin, to lymphoma cells via CD22 and CD38 using bispecific antibodies. Br J Cancer May 1995 71:5 986–94 |
| CD33 | Nakase K, Kita K, Shiku H, Tanaka I, Nasu K, Dohy H, Kyo T, Tsutani H, Kamada N. Myeloid antigen, CD13, CD14, and/or CD33 expression is restricted to certain lymphoid neoplasms. Am J Clin Pathol June 1996 105:6 761–8 |
| CD35 | Yamakawa M, Yamada K, Tsuge T, Ohrui H, Ogata T, Dobashi M, Imai Y. Protection of thyroid cancer cells by complement-regulatory factors. Cancer Jun. 1, 1994 73:11 2808–17 |
| CD44 | Naot D, Sionov R V, Ish-Shalom D. CD44: structure, function, and association with the malignant process. Adv Cancer Res 1997 71: 241–319 |
| CD45 | Buzzi M, Lu L, Lombardi A J Jr, Posner M R, Brautigan D L, Fast L D, Frackelton A R Jr. Differentiation-induced changes in protein-tyrosine phosphatase activity and commensurate expression of CD45 in human leukemia cell lines. Cancer Res Jul. 15, 1992 52:14 4027–35 |
| CD46 | Yamakawa M, Yamada K, Tsuge T, Ohrui H, Ogata T, Dobashi M, Imai Y. Protection of thyroid cancer cells by complement-regulatory factors. Cancer Jun. 1, 1994 73:11 2808–17 |
| CD5 | Stein R, Witz I P, Ovadia J, Goldenberg D M, Yron I. CD5+ B cells and naturally occurring autoantibodies in cancer patients. Clin Exp Immunol September 1991 85:3 418–23 |
| CD52 | Ginaldi L, De Martinis M, Matutes E, Farahat N, Morilla R, Dyer M J, Catovsky D. Levels of expression of CD52 in normal and leukemic B and T cells: correlation with in vivo therapeutic responses to Campath-1H. Leuk Res February 1998 22:2 185–91 |
| CD55 (791Tgp72) | Spendlove, I, L. Li, J. Carmichael, & L. G. Durrant. Decay accelerating factor (CD55): A target for cancer vaccine? (1999) Cancer Research 59: 2282–2286. |
| CD59 | Jarvis G A, Li J, Hakulinen J, Brady K A, Nordling S, Dahiya R, Meri S. Expression and function of the complement membrane attack complex inhibitor protectin (CD59) in human prostate cancer. Int J Cancer Jun. 11, 1997 71:6 1049–55 |
| CDC27 | Wang R F, Wang X, Atwood A C, Topalian S L, Rosenberg S A. Cloning genes encoding MHC class II-restricted antigens: mutated CDC27 as a tumor antigen. Science May 21, 1999 284:5418 1351–4 |
| CDK4 | Wölfel, T., Hauer, M., Schneider, J., Serrano, M., Wölfel, C., Klehmann-Hieb, E., de Plaen, E., Hankeln, T., Meyer zum Büüschenfelde, K, and Beach, D. A p16INK4a-insensitive CDK4 mutant targeted by cytolytic T lymphocytes in a human melanoma. Science Sep. 1, 1995 269:5228 1281–4 |
| CEA | Kass E, Schlom J, Thompson J, Guadagni F, Graziano P, Greiner J W. Induction of protective host immunity to carcinoembryonic antigen (CEA), a self-antigen in CEA transgenic mice, by immunizing with a recombinant vaccinia-CEA virus. Cancer Res Feb. 1, 1999 59:3 676–83 |
| c-myc | Watson P H, Pon R T, Shiu R P. Inhibition of c-myc expression by phosphorothioate antisense oligonucleotide identifies a critical role for c-myc in the growth of human breast cancer. Cancer Res Aug. 1, 1991 51:15 3996–4000 |
| Cox-2 | Tsujii M et al, Cycloxygenase regulates angiogenesis induced by colon cancer cells. Cell 1998; 93: 705–716 |
| DCC | Gotley D C, Reeder J A, Fawcett J, Walsh M D, Bates P, Simmons D L, Antalis T M. The deleted in colon cancer (DCC) gene is consistently expressed in colorectal cancers and metastases. Oncogene Aug. 15, 1996 13:4 787–95 |
| DcR3 | Genomic amplihpication of a decoy receptor for Fas ligand in lung and colon cancer. Pitti R et al, Nature 396, 699–703. 1998. |
| E6/E7 | Steller M A, Zou Z, Schiller J T, Baserga R. Transformation by human papillomavirus 16 E6 and E7: role of the insulin-like growth factor 1 receptor. Cancer Res Nov. 1, 1996 56:21 5087–91 |
| EGFR | Yang X D, Jia X C, Corvalan J R, Wang F, Davis C G, Jakobovits A: Eradication of established tumors by a fully human monoclonal antibody to the epidermal growth factor receptor without concomitant chemotherapy. Cancer Res 1999, 59(6): 1236–43. |
| EMBP | Clinical study on estramustine binding protein (EMBP) in human prostate. Shiina H, Igawa M, Ishibe T. Prostate September 1996 29:3 169–76. |
| Ena78 | D. A. Arenberg et. al., Epithelial-neutrophil activating peptide (ENA-78) is an important angiogenic factor in non-small cell lung cancer. J. Clin. Invest. (1998) 102; 465–472. |
| farsyl transferase | |
| FGF8b and FGF8a | Dorkin T J, Robinson M C, Marsh C, Bjartell A, Neal D E, Leung H Y. FGF8 over-expression in prostate cancer is associated with decreased patient survival and persists in androgen independent disease. Oncogene Apr. 29, 1999 18:17 2755–61 |
| FLK-1/KDR | T. Annie T. Fong et al, SU5416 is a potent and selective inhibitor of the vascular endothelial growth factor receptor (Flk-1/KDR) that inhibits tyrosine kinase catalysis, tumor vacularization and growth of multiple tumor type. Cancer Res, 59, 99–106, 1999 |
| Folic Acid Receptor | Dixon K H, Mulligan T, Chung K N, Elwood P C, Cowan K H. Effects of folate receptor expression following stable transfection into wild type and methotrexate transport deficient ZR-75-1 human breast cancer cells. J Biol Chem Nov. 25, 1992 267:33 24140–7 |
| G250 | Divgi C R, Bander N H, Scott A M, O'Donoghue J A, Sgouros G, Welt S, Finn R D, Morrissey F, Capitelli P, Williams J M, Deland D, Nakhre A, Oosterwijk E, Gulec S, Graham M C, Larson S M, Old L J. Phase I/II radioimmunotherapy trial with iodine-131-labeled monoclonal antibody G250 in metastatic renal cell carcinoma. Clin Cancer Res November 1998 4:11 2729–39 |
| GAGE-Family | De Backer O, 10 others, Boon T, van der Bruggen P. Characterization of the GAGE genes that are expressed in various human cancers and in normal testis. Cancer Res Jul. 1, 1999; 59(13): 3157–3165. |
| gastrin 17 | Watson S A, Michaeli D, Grimes S, Morris T M, Crosbee D, Wilkinson M, Robinson G, Robertson J F, Steele R J, Hardcastle J D. Anti-gastrin antibodies raised by gastrimmune inhibit growth of the human colorectal tumour AP5. Int J Cancer Apr. 10, 1995 61:2 233–40 |
| Gastrin-releasing hormone (Bombesin) | Wang Q J, Knezetic J A, Schally A V, Pour P M, Adrian T E. Bombesin may stimulate proliferation of human pancreatic cancer cells through an autocrine pathway. Int J Cancer Nov. 15, 1996 68:4 528–34 |
| GD2/GD3/GM2 | Wiesner D A, Sweeley C C. Circulating gangliosides of breast-cancer patients. Int J Cancer Jan. 27, 1995 60:3 294–9 |
| GnRH | Bahk J Y, Hyun J S, Lee H, Kim M O, Cho G J, Lee B H, Choi W S. Expression of gonadotropin-releasing hormone (GnRH) and GnRH receptor mRNA in prostate cancer cells and effect of GnRH on the proliferation of prostate cancer cells. Urol Res 1998 26:4 259–64 |

-continued

| Antigen | Reference |
|---|---|
| GnTV | Hengstler J G, Arand M, Herrero M E, Oesch F. Polymorphisms of N-acetyltransferases, glutathione S-transferases, microsomal epoxide hydrolase and sulfotransferases: influence on cancer susceptibility. Recent Results Cancer Res 1998 154: 47–85 |
| GP1 | |
| gp100/Pmel17 | Wagner S N, Wagner C, Schultewolter T, Goos M. Analysis of Pmel17/gp100 expression in primary human tissue specimens: implications for melanoma immuno- and gene-therapy. Cancer Immunol Immunother June 1997 44:4 239–47 |
| gp-100-in4 | Kirkin A F, Dzhandzhugazyan K, Zeuthen J. Melanoma-associated antigens recognized by cytotoxic T lymphocytes. APMIS July 1998 106:7 665–79 |
| gp15 | Maeurer M J, et al. New treatment options for patients with melanoma: review of melanoma-derived T-cell epitope-based peptide vaccines. Melanoma Res. February 1996; 6(1): 11–24. |
| gp75/TRP-1 | Lewis J J, Houghton A N. Definition of tumor antigens suitable for vaccine construction. Semin Cancer Biol December 1995 6:6 321–7 |
| hCG | Hoermann R, Gerbes A L, Spoettl G, Jüüngst D, Mann K. Immunoreactive human chorionic gonadotropin and its free beta subunit in serum and ascites of patients with malignant tumors. Cancer Res Mar. 15, 1992 52:6 1520–4 |
| Heparanase | Vlodavsky I, Friedmann Y, Elkin M, Aingorn H, Atzmon R, Ishai-Michaeli R, Bitan M, Pappo O, Peretz T, Michal I, Spector L, Pecker I. Mammalian heparanase: gene cloning, expression and function in tumor progression and metastasis [see comments]. Nat Med July 1999 5:7 793–802 |
| Her2/neu | Lewis J J, Houghton A N. Definition of tumor antigens suitable for vaccine construction. Semin Cancer Biol December 1995 6:6 321–7 |
| HMTV | Kahl L P, Carroll A R, Rhodes P, Wood J, Read N G. An evaluation of the putative human mammary tumour retrovirus associated with peripheral blood monocytes. Br J Cancer April 1991 63:4 534–40 |
| Hsp70 | Jaattela M, et al. Hsp70 exerts its anti-apoptotic function downstream of caspase-3-like proteases. EMBO J. Nov. 2, 1998; 17(21): 6124–34. |
| hTERT (telomerase) | Vonderheide R H, Hahn W C, Schultze J L, Nadler L M. The telomerase catalytic subunit is a widely expressed tumor-associated antigen recognized by cytotoxic T lymphocytes. Immunity June; 10: 673–679. 1999. |
| IGFR1 | M. J. Ellis et. al., Insulin-like growth factors in human breast cancer. Breast Cancer Res. Treat. (1998) 52; 175–184. |
| IL-13R | Murata T, Obiri N I, Debinski W, Puri R K. Structure of IL-13 receptor: analysis of subunit composition in cancer and immune cells. Biochem Biophys Res Commun Sep. 8, 1997 238:1 90–4 |
| iNOS | Klotz T, Bloch W, Volberg C, Engelmann U, Addicks K. Selective expression of inducible nitric oxide synthase in human prostate carcinoma. Cancer May 15, 1998 82:10 1897–903 |
| Ki 67 | Gerdes, J., U. Schwab, H. Lemke, and H. Stein. Production of a mouse monoclonal antibody reactive with a human nuclear antigen associated with cell proliferation. Int J Cancer 31, 13–20, 1983 |
| KIAA0205 | Guéguen M, Patard J J, Gaugler B, Brasseur F, Renauld J C, Van Cangh P J, Boon T, Van den Eynde B J. An antigen recognized by autologous CTLs on a human bladder carcinoma. J Immunol Jun. 15, 1998 160:12 6188–94 |
| K-ras, H-ras, N-ras | Abrams S I, Hand P H, Tsang K Y, Schlom J. Mutant ras epitopes as targets for cancer vaccines. Semin Oncol February 1996 23:1 118–34 |
| KSA (CO17-1A) | Zhang S, Zhang H S, Reuter V E, Slovin S F, Scher H I, Livingston P O. Expression of potential target antigens for immunotherapy on primary and metastatic prostate cancers. Clin Cancer Res February 1998 4:2 295–302 |
| LDLR-FUT | Caruso M G, Osella A R, Notarnicola M, Berloco P. Leo S, Bonfiglio C, Di Leo A. Prognostic value of low density lipoprotein receptor expression in colorectal carcinoma. Oncol Rep July–August 1998 5:4 927–30 |
| MAGE Family (MAGE1, MAGE3) | Marchand M, et al., Tumor regressions observed in patients with metastatic melanoma treated with an antigenic peptide encoded by gene MAGE-3 and presented by HLA-A1. Int J Cancer Jan. 18, 1999; 80(2): 219–30. |
| Mammaglobin | Watson M A, Dintzis S, Darrow C M, Voss L E, DiPersio J, Jensen R, Fleming T P, Mammaglobin expression in primary, metastatic, and occult breast cancer. Cancer Res Jul. 1, 1999 59:13 3028–31. |
| MAP17 | Kocher O, Cheresh P, Lee S W. Identification and partial characterization of a novel membrane-associated protein (MAP17) up-regulated in human carcinomas and modulating cell replication and tumor growth. Am J Pathol August 1996 149:2 493–500 |
| Melan-A/ MART-1 | Lewis J J, Houghton A N. Definition of tumor antigens suitable for vaccine construction. Semin Cancer Biol December 1995 6:6 321–7 |
| mesothelin | Chang K, et al. Molecular cloning of mesothelin, a differentiation antigen present on mesothelium, mesotheliomas, and ovarian cancers. Proc Natl Acad Sci USA. Jan. 9, 1996; 93(1): 136–40 |
| MIC A/B | Groh V, Steinle A, Bauer S, and Spies T. Recognition of stress-induced MHC molecules by intestinal epithelial gammadelta T cells. Science 1998, 279: 1737–1740. |
| MT-MMP's, such as MMP2, MMP3, MMP7, and MMP9 | Sato H and Seiki M., Membrane-type matrix metalloproteinases (MT-MMPs) in tumormetastasis., J Biochem (Tokyo) February 1996; 119(2): 209–15 |
| Mox1 | Candia A F, Hu J, Crosby J, Lalley P A, Noden D, Nadeau J H, Wright C V. Mox-1 and Mox-2 define a novel homeobox gene subfamily and are differentially expressed during early mesodermal patterning in mouse embryos. Development December 1992 116:4 1123–36 |
| Mucin, such as MUC-1, MUC-2, MUC-3, and MUC-4 | Lewis J J, Houghton A N. Definition of tumor antigens suitable for vaccine construction. Semin Cancer Biol December 1995 6:6 321–7 |
| MUM-1 | Kirkin A F, Dzhandzhugazyan K, Zeuthen J. Melanoma-associated antigens recognized by cytotoxic T lymphocytes. APMIS July 1998 106:7 665–79 |
| NY-ESO-1 | Jager, E. et. al. Simultaneous humoral and cellular immune response against cancer-testis antigen NY-ESO-1: definition of human histocompatibility leukocyte antigen (HLA)-A2-binding peptide epitopes. J. Exp. Med. 1998, 187: 265–270. |
| Osteonectin | Graham J D, Balleine R L, Milliken J S, Bilous A M, Clarke C L. Expression of osteonectin mRNA in human breast tumours is inversely correlated with oestrogen receptor content. Eur J Cancer September 1997 33:10 1654–60 |
| p15 | Yoshida S, Todoroki T, Ichikawa Y, Hanai S, Suzuki H, Hori M, Fukao K, Miwa M, Uchida K. Mutations of p16Ink4/CDKN2 and p15Ink4B/MTS2 genes in biliary tract cancers. Cancer Res Jul. 1, 1995 55:13 2756–60 |
| P170/MDR1 | Trock B J, Leonessa F, Clarke R. Multidrug resistance in breast cancer: a meta-analysis of MDR1/gp170 expression and its possible functional significance. J Natl Cancer Inst Jul. 2, 1997 89:13 917–31 |
| p53 | Roth J, Dittmer D, Rea D, Tartaglia J, Paoletti E, Levine A J. p53 as a target for cancer vaccines: recombinant canarypox virus vectors expressing p53 protect mice against lethal tumor cell challenge. Proc Natl Acad Sci USA May 14, 1996 93:10 4781–6. |
| p97/melano-transferrin | Furukawa K S, Furukawa K, Real F X, Old L J, Lloyd K O. A unique antigenic epitope of human melanoma is carried on the common melanoma glyco-protein gp95/p97. J Exp Med Feb. 1, 1989 169:2 585–90 |

-continued

| Antigen | Reference |
| --- | --- |
| PAI-1 | Grøndahl-Hansen J, Christensen I J, Rosenquist C, Brünner N, Mouridsen H T, Danø K, Blichert-Toft M. High levels of urokinase-type plasminogen activator and its inhibitor PAI-1 in cytosolic extracts of breast carcinomas are associated with poor prognosis. Cancer Res Jun. 1, 1993 53:11 2513–21 |
| PDGF | Vassbotn F S, Andersson M, Westermark B, Heldin C H, Ostman A. Reversion of autocrine transformation by a dominant negative platelet-derived growth factor mutant. Mol Cell Biol July 1993 13:7 4066–76 |
| Plasminogen (uPA) | Naitoh H, Eguchi Y, Ueyama H, Kodama M, Hattori T. Localization of urokinase-type plasminogen activator, plasminogen activator inhibitor-1, 2 and plasminogen in colon cancer. Jpn J Cancer Res January 1995 86:1 48–56 |
| PRAME | Kirkin A F, Dzhandzhugazyan K, Zeuthen J. Melanoma-associated antigens recognized by cytotoxic T lymphocytes. APMIS July 1998 106:7 665–79 |
| Probasin | Matuo Y, Nishi N, Muguruma Y, Yoshitake Y, Kurata N, Wada F. Localization of prostatic basic protein ("probasin") in the rat prostates by use of monoclonal antibody. Biochem Biophys Res Commun Jul. 16, 1985 130:1 293–300 |
| Progenipoietin | |
| PSA | Sanda M G, Smith D C, Charles L G, Hwang C, Pienta K J, Schlom J, Milenic D, Panicali O, Montie J E. Recombinant vaccinia-PSA (PROSTVAC) can induce a prostate-specific immune response in androgen-modulated human prostate cancer. Urology February 1999 53:2 260–6. |
| PSM | Kawakami M, Nakayama J. Enhanced expression of prostate-specific membrane antigen gene in prostate cancer as revealed by in situ hybridization. Cancer Res Jun. 15, 1997 57:12 2321–4 |
| RAGE-1 | Gaugler B, 7 others, Van den Eynde B J. A new gene coding for an antigen recognized by autologous cytolytic T lymphocytes on a human renal carcinoma. Immunogenetics 1996; 44(5): 323–330. |
| Rb | Dosaka-Akita H, Hu S X, Fujino M, Harada M, Kinoshita I, Xu H J, Kuzumaki N, Kawakami Y, Benedict W F. Altered retinoblastoma protein expression in nonsmall cell lung cancer: its synergistic effects with altered ras and p53 protein status on prognosis. Cancer Apr. 1, 1997 79:7 1329–37 |
| RCAS1 | Sonoda K, Nakashima M, Kaku T, Kamura T, Nakano H, Watanabe T. A novel tumor-associated antigen expressed in human uterine and ovarian carcinomas. Cancer Apr. 15, 1996; 77(8): 1501–1509. |
| SART-1 | Kikuchi M, Nakao M, Inoue Y, Matsunaga K, Shichijo S, Yamana H, Itoh K. Identification of a SART-1-derived peptide capable of inducing HLA-A24-restricted and tumor-specific cytotoxic T lymphocytes. Int J Cancer May 5, 1999 81:3 459–66 |
| SSX gene family | Gure A O, Tüüreci O, Sahin U, Tsang S, Scanlan M J, Jäger E, Knuth A, Pfreundschuh M, Old L J, Chen Y T. SSX: a multigene family with several members transcribed in normal testis and human cancer. Int J Cancer Sep. 17, 1997 72:6 965–71 |
| STAT3 | Bromberg J F, Wrzeszczynska M H, Devgan G, Zhao Y, Pestell R G, Albanese C, Darnell J E Jr. Stat3 as an oncogene. Cell Aug. 6, 1999; 98(3): 295–303 |
| STn (mucin assoc.) | Sandmaier B M, Oparin D V, Holmberg L A, Reddish M A, MacLean G D, Longenecker B M. Evidence of a cellular immune response against sialyl-Tn in breast and ovarian cancer patients after high-dose chemotherapy, stem cell rescue, and immunization with Theratope STn-KLH cancer vaccine. J Immunother January 1999 22:1 54–66 |
| TAG-72 | Kuroki M, Fernsten P D, Wunderlich D, Colcher D, Simpson J F, Poole D J, Schlom J. Serological mapping of the TAG-72 tumor-associated antigen using 19 distinct monoclonal antibodies. Cancer Res Aug. 15, 1990 50:16 4872–9 |
| TGF-α | Imanishi K, Yamaguchi K, Suzuki M, Honda S, Yanaihara N, Abe K. Production of transforming growth factor-alpha in human tumour cell lines. Br J Cancer May 1989 59:5 761–5 |
| TGF-β | Picon A, Gold L I, Wang J, Cohen A, Friedman E. A subset of metastatic human colon cancers expresses elevated levels of transforming growth factor beta1. Cancer Epidemiol Biomarkers Prev June 1998 7:6 497–504 |
| Thymosin β 15 | Bao, L., Loda, M., Janmey, P. A., Stewart, R., Anand-Apte, B., and Zetter, B. R. Thymosin beta 15: a novel regulator of tumor cell motility upregulated in metastatic prostate cancer. Nature Medicine. 2(12), 1322–1328. 1996 |
| TNF-α | Moradi M M, Carson L F, Weinberg B, Haney A F, Twiggs L B, Ramakrishnan S. Serum and ascitic fluid levels of interleukin-1, interleukin-6, and tumor necrosis factor-alpha in patients with ovarian epithelial cancer. Cancer Oct. 15, 1993 72:8 2433–40 |
| TPA | Maulard C, Toubert M E, Chretien Y, Delanian S, Dufour B, Housset M. Serum tissue polypeptide antigen (S-TPA) in bladder cancer as a tumor marker. A prospective study. Cancer Jan. 15, 1994 73:2 394–8 |
| TPI | Nishida Y, Sumi H, Mihara H. A thiol protease inhibitor released from cultured human malignant melanoma cells. Cancer Res August 1984 44:8 3324–9 |
| TRP-2 | Parkhurst M R, Fitzgerald E B, Southwood S, Sette A, Rosenberg S A, Kawakami Y. Identification of a shared HLA-A*0201-restricted T-cell epitope from the melanoma antigen tyrosinase-related protein 2 (TRP2). Cancer Res Nov. 1, 1998 58:21 4895–901 |
| Tyrosinase | Kirkin A F, Dzhandzhugazyan K, Zeuthen J. Melanoma-associated antigens recognized by cytotoxic T lymphocytes. APMIS July 1998 106:7 665–79 |
| VEGF | Hyodo I, Doi T, Endo H, Hosokawa Y, Nishikawa Y, Tanimizu M, Jinno K, Kotani Y. Clinical significance of plasma vascular endothelial growth factor in gastrointestinal cancer. Eur J Cancer December 1998 34:13 2041–5 |
| ZAG | Sanchez L M, Chirino A J, Bjorkman P j. 1999, Crystal structure of human ZAG, a fat-depleting factor related to MHC molecules. Science 19; 283(5409): 1914–9 |
| p16INK4 | Quelle D E, Ashmun R A, Hannon G J, Rehberger P A, Trono D, Richter K H, Walker C, Beach D, Sherr C J, Serrano M. Cloning and characterization of murine p16INK4a and p15INK4b genes. Oncogene Aug. 17, 1995; 11(4): 635–45 |
| Glutathione S-transferase | Hengstler J G, Arand M, Herrero M E, Oesch F. Polymorphisms of N-acetyltransferases, glutathione S-transferases, microsomal epoxide hydrolase and sulfotransferases: influence on cancer susceptibility. Recent Results Cancer Res 1998 154: 47–85 |

In the following, a number of specific tumour-associated antigens will be discussed in detail.

Prostate-Specific Membrane Antigen, PSM

In U.S.A., prostate cancer is the second leading cause of cancer death (app. 40,000 per year), and 200,000 patients per year are diagnosed (Boring 1993). Approximately 1 out of 11 men eventually will develop prostatic cancer. Furthermore, approximately 40–60% of prostate cancer patients eventually develop extraprostatic extension of the disease (Babaian 1994). The main strategy in the present invention is to use a therapeutic vaccine as a supplementary therapy to prostatectomy in order to eliminate residual tumour tissue and metastases.

Several pathologic conditions are located to the prostate gland, including benign growth (BPH), infection (prostatitis) and neoplasia (prostatic cancer).

The biological aggressiveness of prostatic cancer is variable. In some patients the detected tumour remains a latent histologic tumour and never becomes clinically significant. In other patients, the tumour progresses rapidly, metastasises and kills the patient in a relatively short time period (2–5 years).

The current primary treatment of prostate cancer is prostatectomy. However, due to the extensive spreading of prostate cancer cells the majority of prostatic cancer patients are not cured by local surgery. Patients with non-confined disease eventually receive systemic androgen ablation therapy, but the annual death rate from prostatic cancer has not declined at all over the 50 years since androgen ablation became standard therapy for metastatic disease.

PSM is a membrane protein which is highly specific for prostatic tissues, benign as well as malignant, although expression of PSM has also been observed in other tissues such as renal tissue and renal tumor, small intestine, brain and tumor neovasculature. Therefore, if surgery was successful, prostatectomised cancer patients should theoretically express PSM on residual malignant prostate tumour tissue or metastases originating from the tumour. By inducing a strong CTL response and/or a strong polyclonal antibody response towards PSM, it is expected that residual tumour tissue can be eliminated.

Interestingly, upregulation of PSM expression is seen following androgen-deprivation therapy of prostate cancer patients (Wright 1996). This would make a PSM-targeted treatment very well-suited to follow the traditional androgen-deprivation therapy.

PSM was first identified in 1987 as a result of generating a monoclonal antibody, 7E11-C5.3, raised against an isolated human prostatic cancer cell, LNCaP (Horoszewicz 1987). The antibody recognised both normal and malignant prostatic epithelium, and was used in 1993 to purify and determine the amino acid sequence of the PSM protein and eventually clone the gene (Israeli 1993).

PSM is a type II transmembrane glycoprotein with a molecular weight of 84 kD as predicted from the nucleic acid sequence whereas the glycosylated version has an observed molecular weight of 100–120 kD. Sequencing of the gene encoding PSM revealed a putative membrane spanning region in connection with three cytosolic arginine anchor residues. The extracellular part of PSM constitute 707 of the total 750 amino acids of the protein, whereas the cytoplasmic domain is predicted to be 19 amino acids long (Israeli 1993). PSM-specific mRNA has been detected in prostate tumour tissue (Israeli 1994), indicating that the tumour antigen is not an aberrantly glycosylated protein which is the case with e.g. the Tn- or sTn-tumour antigens.

The full length PSM cDNA has been transfected into and expressed in a PSM negative human prostate cancer cell line, PC-3 (Kahn 1994). Furthermore, the full length (2.65 kilobases) cDNA has been transcribed and translated in vitro (Kahn 1994).

It has recently been demonstrated that PSM possesses hydrolytic activity resembling that of the N-acetylated ∀-linked acidic dipeptidase (NAALADase)—in fact it has been demonstrated that the two proteins are identical. NAALADase is a membrane-bound hydrolase of the nervous system, which catabolises the neuropeptide N-acetylaspartyl glutamate (NAAG) in order to affect the glutamatergic signalling processes. It is still not known whether this activity of PSM has any relevant biological function.

It is of some importance to predict whether undesired cross-reactivity with other proteins accessible for CTLs or antibodies would be expected following treatment with an autovaccine inducing PSM-specific immune responses. It has been shown that a part of the coding region of the PSM gene (amino acids positions 418–567) has 54% homology to the human transferrin receptor (Israeli 1993). Also, complete sequence identity with the NAALADase enzyme has been found, cf. above. No identification of a functionally relevant similarity with other known peptidases could be made.

The homology to the transferrin receptor is very low and will preferably be disrupted in some of the inventive constructs. The observed sequence identity with human NAALADase is not expected to be an obstacle for a PSM-vaccine, partly because of the low ability of antibodies and CTLs to penetrate the blood-brain barrier. Altogether, even with the most PSM-like construct, it is not expected to experience prohibitive cross-reactivity with other proteins in the patients.

From earlier studies it is clear that PSM is expressed on most prostate cancer cells and prostate originating metastases tested. Further, most other cancers tested, such as carcinomas, sarcomas and melanomas of different tissues as well as a large panel of non-prostatic human cancer cell lines have proven PSM negative.

In addition to this, a very large number of other tissues have been found to be PSM negative. These include colon, breast, lung, ovary, liver, urinary bladder, uterus, bronchus, spleen, pancreas, tongue, esophagus, stomach, thyroid, parathyroid, adrenal, lymph node, aorta, vena cava, skin, mammary gland and placenta. However, RT-PCR has revealed the existence of PSM mRNA in some of these tissues.

Although PSM is predominantly found as a membrane bound molecule on prostate tissue small amounts of PSM can also be detected in the sera of normal individuals and in elevated levels in prostate cancer patients (Rochon 1994, Murphy 1995). The level of circulating PSM in these patients therefore allows a serological monitoring of the effectiveness of a PSM vaccine.

In conclusion, based on the entire amount of data available to date, PSM is an antigen with a high specificity for human prostate tissue and tumours originating therefrom. This means that in patients who have undergone prostatectomy, PSM is a tumour quasi-specific self-antigen. An effective PSM vaccine is therefore likely to target mainly prostatic or prostate-originating metastatic tissue.

As will be clear from Example 1 the method of the invention preferably entails that foreign $T_H$-cell epitope is introduced in a part of the PSM amino acid sequence defined by SEQ ID NO: 2 positions 16–52 and/or 87–108 and/or 210–230 and/or 269–289 and/or 298–324 and/or 442–465 and/or 488–514 and/or 598–630 and/or 643–662 and/or 672–699. Furthermore, a modified PSM molecule which has a foreign $T_H$-epitope introduced in these positions is also a part of the invention.

Accordingly, the invention also pertains to an analogue of human PSM which is immunogenic in humans, said analogue comprising a substantial part of all known and predicted CTL and B-cell epitopes of PSM and including at least one foreign $T_H$ epitope as discussed herein. Preferred PSM analogues are those wherein the at least one foreign $T_H$ epitope is present as an insertion in the PSM amino acid sequence or as a substitution of part of the PSM amino acid sequence or as the result of deletion of part of the PSM amino acid sequence, and most preferred analogues are those wherein a foreign $T_H$-cell epitope is introduced in a part of the PSM amino acid sequence defined by SEQ ID NO: 2 positions 16–52 and/or 87–108 and/or 210–230 and/or 269–289 and/or 298–324 and/or 442–465 and/or 488–514 and/or 598–630 and/or 643–662 and/or 672–699.

Human Chorionic Gonadotropin (HCG)

The relationship between embryonic markers and malignant phenotypes has been under discussion for many decades. An increasing body of data suggests that at least one such marker, human chorionic gonadotropin beta (hCGƎ), is consistently detected on cancer cells of many different histological origins, and that expression of this protein often correlates with increased metastatic properties. A humoral immune response directed against this soluble protein may reduce the chances of tumour spreading and/or may inhibit the recurrence of new primary growths post-surgery.

Human chorionic gonadotropin belongs to a family of glycoprotein hormones, including follicle-stimulating hormone (FSH), thyroid-stimulating hormone (TSH), and luteinizing hormone (LH), all of which are important regulators of reproductive expression and fetal survival. The members of this family of hormones are heterodimers, which share a common ∀-chain. The Ǝ-chain is unique to each hormone and provides the specificity, with the Ǝ-chain of LH exhibiting the strongest sequence homology to hCGƎ (approximately 80%). The apparent molecular weight of hCG-holo, is 37 kD, of which one third is contributed by carbohydrate. The post-translational sugar modifications include both N-linked and O-linked carbohydrate. Abundant sialic acid residues are present and these give the protein a large negative charge. The crystal structure of hCG-holo has been solved (Lapthorn et al., 1994).

Based on the crystal structure it was found that hCG exhibits homology to a family of growth factors, including PDGF and TGFƎ (Lapthorn et al., 1994). This suggests that hCG expression may help regulating cancer cell growth.

Human chorionic gonadotropin is a glycoprotein hormone, which is produced by the placental syncytiotrophoblasts soon after conception, and it is essential for successful gestation in the pregnant woman.

The pathophysiological role of embryonic markers for the development or maintenance of a cancer mass is not known. However, it is of interest to note that trophoblasts (where these proteins are normally produced) have both angiogenic and invasive characteristics, both of which are also necessary properties for a cancer cell. Further, it has been suggested that hCG (or its subunits) can inhibit maternal cellular immune responses to fetal tissue. For example, studies have shown that hCG directly suppresses T cell responses (Jacoby et al., 1984) and it has been proposed that because the lymph nodes draining (in this case) a primary melanoma tumour, are immunosuppressed, a more favourable environment for metastatic tumours to establish themselves may result. As a consequence, expression of hCGƎ may help cancer cells spread into the secondary lymphoid organs. Finally, as mentioned above, structural homology between hCG and a number of growth factors have been demonstrated. Another possibility is therefore that secretion of hCG by cancer cells may give the tumour a growth advantage.

Expression of hCGƎ has been shown in many different types of cancer, for example: a) Prostate adenocarcinoma: positivity for hCGƎ on tissue sections were seen for patients with poor prognosis, irrespective of the histological grade of the tumour (Sheaff et al., 1996), b) different kinds of lung carcinomas; squamous cell (SQCC), adenocarcinoma (AC), and large cell (LCC), all showed a high percentage of reactivity for hCGƎ (Boucher et al. 1995), c) pancreatic adenocarcinoma (Syrigos et al., 1998), d) neuroblastomas, brain cancers, retinoblastomas (Acevedo et al., 1997), e) malignant melanoma (Doi et al., 1996), f) bladder carcinomas (Lazar et al., 1995). A recent paper describes a DNA approach, in which mice were immunized with a hCGƎ expression construct (Geissler et al., 1997). In this in vivo model inhibition of tumour growth was strongly associated with CTL-activity, however high titers of antibodies (which neutralized the biological effect of intact hCG on its cellular receptor) were also detected.

The use of hCG as an immunogen has been described in several papers, focussing on its use as a contraceptive vaccine (Talwar et al., 1976 and Talwar et al., 1994). A very high degree of efficacy and safety has been observed in an anti-fertility clinical trial, using a vaccine against hCG-holo (Talwar et al., 1994). Phase I clinical trials of cancer patients with a vaccine against a synthetic carboxy-terminal peptide of hCGƎ conjugated to diphteria toxoid have also been conducted (Triozzi et al., 1994) and phase II trials are underway. Despite the fact that the idea to use hCGƎ as a cancer vaccine target has been around for some time, it has not been explored in conjunction with the AutoVac technology.

It is known that cells from non-embryonic tissue, or benign neoplasms, do not express hCGƎ. Therefore, there should be no potential side effects from vaccination against this molecule (apart from the effects on pregnancy). Because it is expressed by so many different kinds of cancers this molecule has been proposed to be the "definitive cancer biomarker" (Acevedo et al., 1995 and Regelson W., 1995) and as such would be an attractive target to go after.

Suitable animal models for Further studies of the efficacy of a hCG based vaccine can be found in Acevedo et al., Cancer Det. and Prev. Suppl. (1987) 1: 477–486, and in Kellen et al., Cancer Immunol. Immun.Ther. (1982) 13: 2–4.

Her2

The tyrosine kinase receptors Her2 and EGFr are believed to play a crucial role in the malignant transformation of normal cells and in the continued growth of cancer cells. Overexpression is usually linked to a very poor prognosis.

During the past few years there has been many reports concerning the use of antibodies against these receptors as therapy for cancers that overexpress either or both of these receptors. Genentech Inc. has finished several successful clinical trials on breast cancer patients using a monoclonal antibody against Her2 and has recently obtained an FDA approval for the marketing of the anti-Her2 monoclonal antibody preparation, Herceptin®.

The autovacination technology disclosed herein as applied on the Her2 molecule would elicit polyclonal antibodies that would predominantly react with Her2. Such antibodies are expected to attack and eliminate tumour cells as well as prevent metastatic cells from developing into metastases. The effector mechanism of this anti-tumour effect would be mediated via complement and antibody dependent cellular cytotoxicity.

Dependent on the choice of constructs, the induced autoantibodies could also inhibit cancer cell growth through inhibition of growth factor dependent oligo-dimerisation and internalisation of the receptors. And, most importantly, the Her2 analogues are expected to be able to induce CTL responses directed against known and/or predicted Her2 epitopes displayed by the tumour cells Her2 is a member of the epidermal growth factor receptor family (c-erbB) which consists of four different receptors to date: c-erbB-1 (EGFr), c-erbB-2 (Her2, c-Neu), c-erbB-3 and c-erbB-4 (Salomon et al, 1995). C-erbB-3 and c-erbB-4 are less well characterised than EGFr and Her2. Her2 is an integral glycoprotein. The mature protein has a molecular weight of 185 kD with structural features that closely resembles the EGFr receptor (Prigent et al, 1992). EGFr is also an integral membrane receptor consisting of one subunit. It has an apparent molecular weight of 170 kD and consists of a surface ligand-binding domain of 621 amino acids, a single hydrophobic transmembrane domain of 23 amino acids, and a highly conserved cytoplasmic tyrosine kinase domain of 542 amino acids. The protein is N-glycosylated (Prigent et al, 1994).

All proteins in this family are tyrosine kinases. Interaction with the ligand leads to receptor dimerisation, which increases the catalytic action of the tyrosine kinase (Bernard. 1995, Chantry 1995). The proteins within the family are able to homo- and heterodimerise which is important for their activity. The EGFr conveys growth promoting effects and stimulates uptake of glucose and amino acids by cells (Prigent et al 1992). Her2 also conveys growth promoting signals. Only EGFr binds EGF and TGF-alpha. These ligands do not bind to the other receptors in the family (Prigent et al., 1992). The ligands for Her2 are not fully determined. However, heregulin has been shown to induce phosphorylation by activating Her2. This does not appear to be due to a direct binding to the receptor but it is believed that heregulin is a ligand for erbB-3 and erbB-4 which then activates Her2 by oligo-dimerisation (Solomon et al 1995).

The homology between the proteins of EGF receptor family is most pronounced in the tyrosine kinase domain at the cytoplasmic part of the molecules (82% between EGFr and Her2). The homology is less in the extracellular part—from 41% to 46% in different domains (Prigent et al, 1992).

The epidermal growth factor receptor is expressed on normal tissues in low amounts, but it is overexpressed in many types of cancers. EGFr is overexpressed in breast cancers (Earp et al, 1993, Eppenberger 1994), gliomas (Schlegel et al, 1994), gastric cancer (Tkunaga et al, 1995), cutaneous squamous carcinoma (Fujii 1995), ovarian cancer (van Dam et al, 1994) and others. Her2 is also expressed on few normal human tissues in low amount, most characteristically on secretory epithelia. Over expression of Her2 occurs in about 30% of breast, gastric, pancreatic, bladder and ovarian cancers.

The expression of these receptors varies depending on the degree of differentiation of the tumours and the cancer type, e.g., in breast cancer, primary tumours overexpress both receptors; whereas in gastric cancer, the overexpression occurs at a later stage in metastatic tumours (Salomon et al, 1995). The number of overexpressed receptors on carcinoma cells is greater than $10^6$/cell for several head and neck cancers, vulva, breast and ovarian cancer lines isolated from patients (Dean et al, 1994).

There are several reasons why the EGFr family of receptors constitute suitable targets for tumour immunotherapy. First, they are overexpressed in many types of cancers, which should direct the immune response towards the tumour. Second, the tumours often express or overexpress the ligands for this family of receptors and some are hypersensitive to the proliferative effects mediated by the ligands. Third, patients with tumours that overexpress growth factor receptors often have a poor prognosis. The overexpression has been closely linked with poor prognosis especially in breast cancer, lung cancer and bladder cancer (2) and is apparently associated with invasive/metastatic phenotypes, which are rather insensitive to conventional therapies (Eccles et al, 1994).

Overexpression of Her2 is in some cases a result of amplification of the gene and in other cases increased transcription and translation. The overexpression of Her2 is associated with poor prognosis in breast, ovarian cancers, gastric cancer, bladder cancer and possibly in non-small cell lung cancers (Solomon et al, 1995).

Phase I clinical trials have been performed with a bispecific antibody in patients with advanced breast and ovarian cancer. The antibody was bispecific against Her2 and Fc(RI (Weiner et al, 1995). Efficient lysis of Her2 over expressing tumour cells was observed with a bispecific antibody against Her2 and CD3 (Zhu et al, 1995).

Treatment of scid mice xenografted with human gastric cancer with an anti-Her2 monoclonal antibody prolonged the survival of the mice (Ohniski et al, 1995). The anti-tumour activities of monoclonal antibodies against Her2, in vitro and in vivo is not due to an identical mechanism; they may act as partial ligand agonists, alter Her2 receptor turnover and phosphorylation or may affect dimerization (Lupu et al, 1995).

Similarly, it has been shown that antibodies to EGFr can also interfere with growth factor interactions. (Baselga et al, 1994, Modjahedi et al, 1993a, Wu et al, 1995, Modjahedi et al, 1993b, Tosi et al, 1995, Dean et al, 1994, Bier et al, 1995, Modjtahedi et al, 1996, Valone 1995).

Hence, an important embodiment of the methods of the invention is one wherein the foreign T-cell epitope is introduced in a part of the Her2 amino acid sequence defined by the amino acid numbering in SEQ ID NO: 3 (also shown in SEQ ID NO: 4) positions 5–25 and/or 59–73 and/or 103–117 and/or 149–163 and/or 210–224 and/or 250–264 and/or 325–339 and/or 369–383 and/or 465–479 and/or 579–593 and/or 632–652 and/or 653–667 and/or 661–675 and/or 695–709 and/or 710–730, cf. the Examples.

Accordingly, the invention also relates to an analogue of human Her2 which is immunogenic in humans, said analogue comprising a substantial part of all known and predicted CTL and B-cell epitopes of Her2 and including at least one foreign $T_H$ epitope as discussed herein. It is preferred that the at least one foreign $T_H$ epitope is present as an insertion in the Her2 amino acid sequence or as a substitution of part of the Her2 amino acid sequence or as the result of deletion of part of the Her2 amino acid sequence. Most preferred analogues are those defined above, i.e. those wherein the foreign T-cell epitope is introduced in a part of the Her2 amino acid sequence defined by SEQ ID NO: 3 positions positions 5–25 and/or 59–73 and/or 103–117 and/or 149–163 and/or 210–224 and/or 250–264 and/or 325–339 and/or 369–383 and/or 465–479 and/or 579–593 and/or 632–652 and/or 653–667 and/or 661–675 and/or 695–709 and/or 710–730.

FGF8b

It has been shown by several investigators that FGF8b can induce proliferation, transformation, differentiation and in some cases greatly increase the tumorigenicity of mammalian cells and tissues (Tanaka 1992, Kouhara 1994, Lorenzi 1995, MacArthur 1995a, Crossley 1996a, 1996b, Ghosh 1996, Ohuchi 1997a, Rudra-Ganguly 1998). These effects are primarily mediated through the binding of FGF8b to members of the fibroblast growth factor receptors FGFR2, FGFR3, and FGFR4 (MacArthur 1995b, Blunt 1997, Tanaka 1998). Thus, cells expressing one of these receptors and FGF8(b) have been shown to provide an autocrine growthsignaling cascade leading to proliferation. The biological effect of FGF8b is most likely partly mediated through the JAK/STAT3 pathway, since we and others have observed that addition of FGF8b to the growth medium of certain cells does promote phosphorylation of STAT3, a feature suspected to render cells resistant to apoptosis (Catlett-Falcone 1999).

In addition to the in vitro observations mentioned above, it has recently been shown that FGF8(b) expression is significantly upregulated in both prostate and breast cancers (Marsh 1999, Dorkin 1999). We therefore believe, that an autovaccine against FGF8(b) will be a very efficient means of treating a number of FGF8-expressing tumors, or perhaps increase their sensitivity towards apoptosis inducing agents.

Prostate Cancer

The biological aggressiveness of prostatic cancer is variable. In some patients the detected tumor remains a latent histologic tumor and never becomes clinically significant. In other patients, the tumor progresses rapidly, metastasizes, and kills the patient in a relatively short time (2–5 years).

For the purpose of diagnosis, and to follow the response to therapy of prostate cancer, determination of the circulating levels of two proteins has primarily been used: prostatic acid phosphatase (PAP) and prostate specific antigen (PSA) (Nguyen 1990, Henttu 1989). Due to disrupture of the normal architecture of the prostate gland in response to cancer development, these soluble proteins are released into the circulation where they can be detected as markers for e.g. metastatic spread.

The current primary treatment of prostate cancer is prostatectomy. However, due to the extensive spreading of prostate cancer cells the majority of prostatic cancer patients are not cured by local surgery. Patients with non-confined disease receive systemic androgen ablation therapy, but the annual death rate from prostatic cancer has not declined at all over the 50 years since androgen ablation became standard therapy for metastatic disease.

RT-PCR analysis has shown that FGF8 mRNA is produced by the human prostatic epithelial tumor cell lines LNCaP, PC-3, ALVA-31, and DU145 respectively, with FGF8b being the most prominent isoform (Tanaka 1995, Ghosh 1996). The growth of the androgen-responsive LNCaP cells are stimulated by addition of recombinant FGF8b (Tanaka 1995), while DU145 cells could be growth inhibited by transfection with vira expressing anti-sense FGF8b (Rudra-Ganguly 1998). This, together with evidence from developmental studies discussed below, indicate a role for FGF8b in maintaining the cancerous state of these cell lines.

Using FGF8a cDNA for in situ hybridization experiments, Leung and co-workers have shown that a high proportion (80% (n=106), and 71% (n=31)) of prostatic cancers produce FGF8 mRNA, and that the amount of FGF8 mRNA correlate with the severeness of the tumors (P<0.0016, and P<0.05, respectively) (Leung 1996, Dorkin 1999). Using a monoclonal anti-FGF8b antibody, this isoform was shown responsible for the overexpression of FGF8b (Dorkin 1999). Additionally, men with tumors which expressed high levels of FGF8 had worse survival (P=0,034), and that FGF8 expression persisted in androgen independent prostate cancers (Dorkin 1999). According to the data presented by Dorkin and coworkers the expression of FGF8b in prostate cancer could predict patient survival.

Immunohistochemical analysis using a monoclonal antibody against FGF8, has detected the protein in 93% (n=43) of human prostate cancers (Tanaka 1998). Normal prostatic tissue or benign prostatic hyperplasia does produce low levels of FGF8 mRNA, and does not contain detectable amounts of FGF8 protein (Leung 1996, Yoshimura 1996, Ghosh 1996, Tanaka 1998, Dorkin 1999).

These results indicate that an autovaccine against FGF8 (b) would be reactive against prostatic tumor tissue and thus, extremely valuable in the treatment of prostatic cancer.

Breast Cancer

The current treatment of breast cancer is surgery. However, due to the extensive spreading of breast cancer cells a large part of breast cancer patients are not cured by local surgery. Patients with non-confined disease eventually receive androgen ablation therapy, chemotherapy, and or radiation therapy. The annual death rate from breast cancer is, however, still relatively high.

FGF8 was originally isolated from a mouse mammary carcinoma cell-line (SC-3), from which the expression could be induced by adding androgen to the medium (Nonomura 1990). The protein is also known to induce the proliferation of these as well as other mammalian cells. Recently FGF8b mRNA has been shown to be present in eight (n=8) human breast cancer cell lines (MDA-MB-231, MDA-MB-415, ZR 75-1, T-47-D, SK-BR-III, PMC-42, HBL-100 and MCF-7) (Tanaka 1995, Payson 1996, Wu 1997, Marsh 1998).

Wnt-1 transgenic mice infected with mouse mammary tumor virus (MMTV) develop mammary tumors. FGF8 transcription is activated in 50% of these tumors (MacArthur 1995c, Kapoun 1997).

Transgenic mice that are carrying the FGF8b cDNA under control of the very specific mouse mammary tumor virus (MMTV) promoter, are shown to spontaneously develop FGF8b expressing mammary tumors (Coombes, personal communication).

Very recent data shows that FGF8(b) expression is upregulated in breast cancer (Tanaka 1998, Marsh 1999). Tanaka and co-workers used a new monoclonal FGF8 antibody in immunohistochemical studies. They showed that FGF8 was present in 67% (n=12) of breast cancers, and that androgen receptors were present in 89% of FGF8 positive breast diseases (Hyperplasia, Fibroadenoma, Intraductal papilloma, and cancers), which would allow the autocrine growth promoting loop to be involved in the progression of breast cancers (Tanaka 1998). Using a semi-quantitative RT-PCR method, it was shown that elevated levels of FGF8 mRNA were found in malignant compared to non-malignant breast tissues. Significantly more malignant tissues were expressing FGF8 (p=0.019) at significantly higher levels (p=0.031) (68 breast cancers and 24 non-malignant breast tissues) (Marsh 1999).

It has not yet been fully established that FGF8(b) functions as an autocrine growth factor. However, the fact that a large number of tumors overexpress FGF8b argues strongly that an autovaccine against FGF8b could be effective against a large percentage of breast and prostate cancers. The data reported by Marsh, Dorkin, and Tanaka indicate that an autovaccine against FGF8(b) could be used for treatment of both breast and prostate cancers, and the rather vague data presented by Dorkin et. al, is a further support of the opinion that FGF8 is involved in the proliferation of human cancer cells.

Description of FGF8b

FGF8 belongs to the family of fibroblast growth factors (FGFs). These growth regulatory proteins are small ~200 amino acid residue proteins that all are involved in the induction of proliferation and differentiation of a wide range of cells. For a recent review of the involvement of the fibroblast growth factors in vertebrate limb development, see Johnson 1997. The FGF family members are evolutionary related and share 20–50% amino acid sequence identity.

FGF8b is a splice variant of FGF8, originally termed androgen induced growth factor (AIGF). AIGF was first identified as a protein secreted by a murine mammary carcinoma derived cell line (SC-3) upon stimulation with androgen (Nonomura 1990). The murine FGF8 gene contains 6 exons, potentially coding for eight different FGF8-isoforms (FGF8a–h), differing only in the N-terminal part of the molecules (Crossley 1995, MacArthur 1995b). Human FGF8 has the same gene structure as the murine gene. However, due to a stop codon in exon 1B, human FGF8 can possibly exist in four different isoforms namely FGF8a, FGF8b, FGF8e, and FGF8f (Gemel 1996). The gene structures and the amino acid sequences of the four human isoforms are illustrated in FIG. 5.

Mature FGF8b contains 193 amino acid residues, and has a calculated molecular weight of 22.5 kDa. The highly basic protein contains 21 arginine and 14 lysine residues resulting in a calculated isoelectric point of 10.84, and a calculated positive charge of 19,8 at pH 7.0. It contains two cysteine residues, and has two potential N-glycosylation sites. Due to the nature of the investigations performed involving FGF8b very little is known about the FGF8b protein moiety. It has, however, been expressed heterologously from bacteria, purified by the use of a C-terminal hexa-Histidine tag, and in vitro refolded to a soluble and biologically active state (MacArthur 1995a, Blunt 1997).

Biological Activity of FGF8b

As mentioned above, FGF8(b) was first isolated as a factor that was released from a androgen dependent mouse mammary tumor cell line, and it has been shown that this protein can induce the proliferation of these cells. The morphological changes mimic those induced by testosterone, which is also know to induce the synthesis of FGF8(b) mRNA (Tanaka 1992). The proliferation can be inhibited by FGF8(b) antisense oligos (Nonomura 1990, Tanaka 1992, and Yamanishi 1994). Indeed, a human prostate cancer cell line DU145 could be growth inhibited by transfection with vira expressing anti-sense FGF8b (Rudra-Ganguly 1998). Recent data shows that FGF8b induces phosphorylation of STAT3—a protein that is suspected to be involved in resistance to apoptosis (Catlett-Falcone 1999, Johnston, C. L., unpublished results).

FGF8b has by several investigators been shown very efficient in inducing the transformation of NIH3T3 or SC115 cells (Miyashita 1994, Kouhara 1994, Lorenzi 1995, MacArthur 1995a). By using recombinantly expressed proteins, it has also been shown that this induction of morphological changes is far more efficient with FGF8b than when using FGF8a or FGF8c (MacArthur 1995a, Ghosh 1996). Interestingly, the N-terminal half of the FGF8b molecule alone, was shown to be sufficient for transformation of NIH3T3 cells, and even the small FGF8b specific peptide (QVTVQSSPNFT)(SEQ ID NO: 41) could enable the cells to grow 2–3 times longer than normal in 0.1% serum (Rudra-Ganguly 1998). Furthermore, NIH3T3 cells stably transfected with an expression vector encoding FGF8b has been reported to be very tumorigenic when injected intraocularly into nude mice (Kouhara 1994, Ghosh 1996).

In vivo, FGF8b is known to be expressed at certain stages of development in vertebrates. A summary of the biological roles assigned to FGF8(b) is shown in Table 1. For reviews on the involvement of FGF8 in vertebrate development see Goldfarb 1999, and Johnson 1997.

TABLE

Various sites/tissues known to produce FGF8, and the proposed biological role(s).

| Action/mechanism/presence (species) | References |
| --- | --- |
| Present in the developing limb buds (mouse) | Heikinheimo 1994, Ohuchi 1994 |
| Limb bud outgrowth (chicken) | Kuwana 1997, Xu 1998 |
| Induction of ectopic limb formation from mesoderm (chicken) | Crossley 1996b |
| Induction of midbrain formation from the caudal diencephalon (chicken) | Crossley 1996a |
| Initiation of wing outgrowth in a wingless mutant (chicken) | Ohuchi 1997a |
| Role in dorsoventral patterning of the gastrula (zebrafish) | Fürthauer 1997 |
| Required during gastrulation, cardiac, craniofacial, forebrain, midbrain and cerebellar development (tissue specific knockout mice) | Meyers 1998 |
| Role in tooth morphogenesis (mouse) | Kettunen 1998 |

It is believed that FGF8(b) mediates its action through binding to the fibroblast growth factor receptors (FGFR's). Specifically, FGF8b is known to be able to activate FGFR2c, FGFR3c, FGFR4c, and to some extent also FGFR1c, but not FGFR1b, -2b or -3b (MacArthur 1995b, Blunt 1997). In case of the induction of outgrowth of ectopic chicken limbs, it is implicated that FGF10, FGFR2, and FGF8 interact and that this could be sufficient for outgrowth (Kuwana 1997, Xu 1998). These results support the hypothesis that FGF8(b) can act in an auto- and paracrine manner, leading to the normal outgrowth and patterning of several anatomical structures during vertebrate development. Importantly, FGF8 "total knock out" mice do not survive most likely due to the elaborate involvement of the protein in the development of the embryo.

Homology to Other Proteins

It is of significant importance to predict whether undesired cross-reactivity with other proteins accessible for antibodies would be expected following treatment with an autovaccine inducing FGF8b specific autoantibodies. Due to the high degree of sequence identity between FGF8b and the other FGF8 molecules, an autovaccine will be expected to cross-react with these proteins. This, however, will presumably be advantageous, since none of these proteins are reported to be expressed in tissues or by cell-lines that do not already express FGF8b.

Amino acid residues 55 through 175 of FGF8b shows a relatively low but significant degree of sequence identity to the other FGFs. It is commonly accepted (and several times proven) that a significant degree of sequence identity between two protein domains is also reflected in a high degree of tertiary structure similarity. Therefore, the FGF family members are all generally expected to be structurally similar. The three dimensional structure of FGF2 has been resolved from crystals as well as in solution (Ago 1991, Zhang 1991, Zhu 1991, Eriksson 1993, Blaber 1996, Moy 1996). FGF2 is composed entirely of beta-sheet structure, comprising a three-fold repeat of a four-stranded antiparallel beta-meander. This beta-barrel structure is totally conserved between interleukin 1, FGF2 (or basic FGF), and FGF1 (or acidic FGF). Nuclear magnetic resonance analysis of FGF2 in solution has shown that the N-terminal part of the molecule forms a relatively flexible structure. The remaining part of FGF8b (amino acid residues 1–54 and 176–215) only shows a low degree of sequence identity to known proteins.

Based on the structural and alignment data, it is generally assumed that the three dimensional structural core of the other fibroblast growth factors closely resemble those of FGF1 and FGF2. These structural considerations are important factors in our design of the FGF8b mutant autovaccine molecules.

Importantly, due to the relatively low degree of sequence identity between FGF8 and any of the other members of the FGF family, the surface of FGF8 would be very different from that of other FGFs, thereby minimizing the cross-reactivity of FGF8b autovaccine generated antibodies with other FGF family members. Due to the very low degree of homology to other proteins than the fibroblast growth factors, we do not expect an autovaccine against FGF8b to cross-react with any other proteins.

It should be emphasized, however, that an autovaccine against FGF8b probably would cross react with all isoforms of FGF8. This will, however, presumably not be a problem since none of the FGF8 isoforms are expected to be expressed at significant levels in the adult. It is even possible that this cross reaction will be beneficial in the treatment of cancer, since it has been shown that at least some cancer cell lines express other isoforms in addition to FGF8b.

Tissue Distribution of FGF8b

Ideally, the induced autoantibodies and the subsequent effector mechanisms as well as the expected CTL response raised by autovaccination should only be directed towards tissues that are to be eliminated in the patient. Therefore, the tissue distribution of the antigen, which is targeted by an autovaccine, is an issue of great importance concerning the safety of the vaccine.

TABLE

Expression of FGF8b in various tissues and cells

| | |
|---|---|
| Human | |
| Breast cancer cell lines (MDA-MB-231, MDA-MB-415, ZR 75-1, T-47-D, SK-BR-III, PMC-42, HBL-100, and MCF-7) | ((RT-PCR) Tanaka 1995, Payson 1996, Wu 1997, Marsh 1999) |
| Breast tumors | ((mAb) Tanaka 1998, (RT-PCR) Marsh 1999) |
| Normal breast tissue | ((RT-PCR) Wu 1997, Marsh 1999 (mAb) Tanaka 1998) |
| Prostate cancer (93%) | ((in situ hyb.) Leung 1996, Dorkin 1999, (mAb) Tanaka 1998) |
| Breast disease | ((mAb) Tanaka 1998) |
| Prostatic tumor cells (LNCaP, PC-3, DU145, and ALVA-31) | ((RT-PCR) Tanaka 1995, Ghosh 1996, Schmitt 1996) |
| fetal kidney | ((Northern blot) Ghosh 1996) |
| adult prostate, testis, kidney, neurons | ((RT-PCR) Ghosh 1996, Wu 1997, Dorkin 1999) |
| teratocarcinoma cells (Tera-2) | ((RT-PCR) Wu 1997) |
| Murine | |
| Breast cancer cell lines (SC-115, RENCA) | ((RT-PCR) Yoshimura 1996) |
| Hypothalamus, Testis | ((RT-PCR) Yoshimura 1996) |
| Mammary tumors (Wnt-1 transgenic) | ((Northern blot) MacArthur 1995c) |
| Embryonic brain | ((in situ hyb.) Crossley 1995, Heikinheimo 1994, Ohuchi 1994, Shimamura 1997, (RT-PCR) Blunt 1997) |
| Ovary, testis | ((Northern blot) Valve 1997) |
| Developing face and limb buds | ((pAb) MacArthur 1995b (in situ hyb.) Heikinheimo 1994, Ohuchi 1994, Crossley 1995) |
| Gastrula | ((in situ hyb.) Crossley 1995) |

TABLE-continued

Expression of FGF8b in various tissues and cells

| | |
|---|---|
| Chicken | |
| Embryonic brain | ((in situ hyb.) Crossley 1996a) |
| developing limb buds | ((in situ hyb.) Ohuchi 1997a, b) |
| Rat | |
| Prostate and testis | (RT-PCR) Scmitt 1996 |

The above table shows a wide selection of tissue distribution, and cell line data of FGF8b expression. As seen from the table, most of the data regarding tissue distribution is generated using the sensitive RT-PCR method. This is because Northern blotting analysis does not detect any FGF8b mRNA in any normal tissues except from fetal kidney. From this scarce data, it is generally assumed that expression of FGF8b mRNA in the adult is very limited, and thus, an autovaccine against FGF8b would presumably not be reactive against normal tissue. Due to the fact that small amounts of FGF8b could interact in unknown systems in the adult, the tissue distribution of the protein needs further analysis. There are, however, in our opinion no indications that an autovaccine against FGF8b would result in serious unwanted effects on the patients.

Effects of Antibodies Against FGF8b

So far, no attempts to treat prostate cancer using monoclonal antibodies have been published. Clinical trials with monoclonal antibodies are ongoing in breast cancer therapy studies, however.

Antibodies against FGF8b will probably block the interaction between FGF8b and its receptors, which will inhibit the cell membrane ruffling and cell proliferation, very likely decreasing the motility and invasiveness of the cancer cells.

Hence, the invention also relates to embodiments of the methods described herein where, where the foreign T-cell epitope is introduced in a part of the FGF8b amino acid sequence defined by SEQ ID NO: 6 (encoded by nucleotide sequence SEQ ID NO: 5) positions 1–54 and/or 178–215 and/or 55–58 and/or 63–68 and/or 72–76 and/or 85–91 and/or 95–102 and/or 106–111 and/or 115–120 and/or 128–134 and/or 138–144 and/or 149–154 and/or 158–162 and/or 173–177. It should be noted that it is especially preferred not to introduce variations or modifications in positions 26–45 and in the C-terminus starting at amino acids 186–215, since these stretches show the least homology with a recently discovered protein, FGF-18, which seems to be expressed in a variety of non-tumour tissues.

Accordingly, the invention also pertains to an analogue of human/murine FGF8b which is immunogenic in humans, said analogue comprising a substantial part of all known and predicted CTL and B-cell epitopes of FGF8b and including at least one foreign $T_H$ epitope as discussed herein. It is preferred that the at least one foreign $T_H$ epitope is present as an insertion in the FGF8b amino acid sequence or as a substitution of part of the FGF8b amino acid sequence or as the result of deletion of part of the FGF8b amino acid sequence. Most preferred analogues in this embodiment are those where the foreign T-cell epitope is introduced in a part of the FGF8b amino acid sequence defined by SEQ ID NO: 6 positions 1–54 and/or 178–215 and/or 55–58 and/or 63–68 and/or 72–76 and/or 85–91 and/or 95–102 and/or 106–111 and/or 115–120 and/or 128–134 and/or 138–144 and/or 149–154 and/or 158–162 and/or 173–177.

Mucins

The invention also pertains to methods of the invention employing specifically modified versions of the human mucins, especially any of MUC-1 through MUC-4, preferably MUC-1. The analogues comprise the following structure

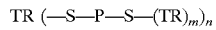
TR (—S—P—S—(TR)$_m$)$_n$ where TR is a tandem repeat derived from the naturally occurring mucin, P is a foreign $T_H$-epitope as discussed herein, S is an inert spacer peptide having from 0 to 15 amino acid residues, preferably between 0 and 10 amino acid residues, and n is an integer of from 1 to 30, and m is an integer from 1 to 10, preferably from 3 to 5.

When producing such a mucin analogue in e.g. a human cell line or by purification from a tissue, the direct result will normally not have a glycosylation pattern as desired, i.e. an aberrant glycosylation pattern resembling that of a tumour derived mucin. However, it is possible to produce the analogue recombinantly in e.g. *E. coli* or by synthetic means, and subsequently glycosylating the product enzymatically so as to achieve a Tn or S-Tn glycosylation pattern specific for MUC-1 expressed on tumours. Alternatively, the polypeptide could be prepared in a mammalian cell line or an insect cell line, eg. *Drosophila* cells, which lacks the relevant enzyme or by expressing the protein intracellularly (by omitting a secretion signal peptide) where glycosylation does not occur.

Nucleic Acid Fragments and Vectors of the Invention

It will be appreciated from the above disclosure that the analogues can be prepared by means of recombinant gene technology but also by means of chemical synthesis or semisynthesis; the latter two options are especially relevant when the modification consists in coupling to protein carriers (such as KLH, diphtheria toxoid, tetanus toxoid, and BSA) and non-proteinaceous molecules such as carbohydrate polymers and of course also when the modification comprises addition of side chains or side groups to an polypeptide-derived peptide chain.

For the purpose of recombinant gene technology, and of course also for the purpose of nucleic acid immunization, nucleic acid fragments encoding the necessary epitopic regions and analogues are important chemical products. Hence, an important part of the invention pertains to a nucleic acid fragment which encodes an analogue described above of any of the relevant tumour-specific polypeptides, preferably a polypeptide wherein has been introduced a foreign $T_H$-cell epitope by means of insertion and/or addition, preferably by means of substitution and/or deletion. The nucleic acid fragments of the invention are either DNA or RNA fragments.

The nucleic acid fragments of the invention will normally be inserted in suitable vectors to form cloning or expression vectors carrying the nucleic acid fragments of the invention; such novel vectors are also part of the invention. Details concerning the construction of these vectors of the invention will be discussed in context of transformed cells and microorganisms below. The vectors can, depending on purpose and type of application, be in the form of plasmids, phages, cosmids, mini-chromosomes, or virus, but also naked DNA which is only expressed transiently in certain cells is an important vector. Preferred cloning and expression vectors of the invention are capable of autonomous replication, thereby enabling high copy-numbers for the purposes of high-level expression or high-level replication for subsequent cloning.

The general outline of a vector of the invention comprises the following features in the 5'63' direction and in operable linkage: a promoter for driving expression of the nucleic acid fragment of the invention, optionally a nucleic acid sequence encoding a leader peptide enabling secretion of or integration into the membrane of the polypeptide fragment, the nucleic acid fragment of the invention, and a nucleic acid sequence encoding a terminator. When operating with expression vectors in producer strains or cell-lines it is for the purposes of genetic stability of the transformed cell preferred that the vector when introduced into a host cell is integrated in the host cell genome. In contrast, when working with vectors to be used for effecting in vivo expression in an animal (i.e. when using the vector in DNA vaccination) it is for security reasons preferred that the vector is not capable of being integrated in the host cell genome; typically, naked DNA or non-integrating viral vectors are used, the choices of which are well-known to the person skilled in the art.

The vectors of the invention are used to transform host cells to produce the analogue of the invention. Such transformed cells, which are also part of the invention, can be cultured cells or cell lines used for propagation of the nucleic acid fragments and vectors of the invention, or used for recombinant production of the analogues of the invention. Alternatively, the transformed cells can be suitable live vaccine strains wherein the nucleic acid fragment (one single or multiple copies) have been inserted so as to effect secretion or integration into the bacterial membrane or cell-wall of the analogue.

Preferred transformed cells of the invention are microorganisms such as bacteria (such as the species *Escherichia* [e.g. *E. coli*], *Bacillus* [e.g. *Bacillus subtilis*], *Salmonella*, or *Mycobacterium* [preferably non-pathogenic, e.g. *M. bovis* BCG]), yeasts (such as *Saccharomyces cerevisiae*), and protozoans. Alternatively, the transformed cells are derived from a multicellular organism such as a fungus, an insect cell, a plant cell, or a mammalian cell. Most preferred are cells derived from a human being, cf. the discussion of cell lines and vectors below.

For the purposes of cloning and/or optimized expression it is preferred that the transformed cell is capable of replicating the nucleic acid fragment of the invention. Cells expressing the nucleic fragment are preferred useful embodiments of the invention; they can be used for small-scale or large-scale preparation of the analogue or, in the case of non-pathogenic bacteria, as vaccine constituents in a live vaccine.

When producing the analogue of the invention by means of transformed cells, it is convenient, although far from essential, that the expression product is either exported out into the culture medium or carried on the surface of the transformed cell.

When an effective producer cell has been identified it is preferred, on the basis thereof, to establish a stable cell line which carries the vector of the invention and which expresses the nucleic acid fragment encoding the analogue. Preferably, this stable cell line secretes or carries the analogue of the invention, thereby facilitating purification thereof.

In general, plasmid vectors containing replicon and control sequences which are derived from species compatible with the host cell are used in connection with the hosts. The vector ordinarily carries a replication site, as well as marking sequences which are capable of providing phenotypic selection in transformed cells. For example, *E. coli* is typically transformed using pBR322, a plasmid derived from an *E.* coli species (see, e.g., Bolivar et al., 1977). The pBR322 plasmid contains genes for ampicillin and tetracycline resistance and thus provides easy means for identifying transformed cells. The pBR plasmid, or other microbial plasmid or phage must also contain, or be modified to contain, promoters which can be used by the prokaryotic microorganism for expression.

Those promoters most commonly used in recombinant DNA construction include the B-lactamase (penicillinase) and lactose promoter systems (Chang et al., 1978; Itakura et al., 1977; Goeddel et al., 1979) and a tryptophan (trp) promoter system (Goeddel et al., 1979; EP-A-0 036 776). While these are the most commonly used, other microbial promoters have been discovered and utilized, and details concerning their nucleotide sequences have been published, enabling a skilled worker to ligate them functionally with plasmid vectors (Siebwenlist et al., 1980). Certain genes from prokaryotes may be expressed efficiently in *E. coli* from their own promoter sequences, precluding the need for addition of another promoter by artificial means.

In addition to prokaryotes, eukaryotic microbes, such as yeast cultures may also be used, and here the promoter should be capable of driving expression. *Saccharomyces cerevisiae*, or common baker's yeast is the most commonly used among eukaryotic microorganisms, although a number of other strains are commonly available such as *Pichia pastoris*. For expression in *Saccharomyces*, the plasmid YRp7, for example, is commonly used (Stinchcomb et al., 1979; Kingsman et al., 1979; Tschemper et al., 1980). This plasmid already contains the trpl gene which provides a selection marker for a mutant strain of yeast lacking the ability to grow in tryptophan for example ATCC No. 44076 or PEP4–1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate in culture (tissue culture) has become a routine procedure in recent years (Tissue Culture, 1973). Examples of such useful host cell lines are VERO and HeLa cells, Chinese hamster ovary (CHO) cell lines, and W138, BHK, COS-7 293 and MDCK cell lines.

Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, VSV, BPV) or may be provided by the host cell chromosomal replication mechanism. If the vector is integrated into the host cell chromosome, the latter is often sufficient.

Compositions of the Invention

The invention also relates to an immunogenic composition which comprises, as an effective immunogenic agent at least one of the analogues described herein in admixture with a pharmaceutically and immunologically acceptable carrier, vehicle, diluent, or excipient, and optionally an adjuvant, cf also the discussion of these entities in the description of the method of the invention above.

Furthermore, the invention also relates to a composition composition for inducing production of antibodies against any one of the above discussed tumour antigens, the composition comprising a nucleic acid fragment or a vector of the invention, and
a pharmaceutically and immunologically acceptable diluent and/or vehicle and/or carrier and/or excipient and/or adjuvant.

Formulation and other specifics concerning such compositions are discussed in the relevant section regarding nucleic acid immunisation above.

EXAMPLE 1

Vaccination Against PSM

In the following it will be described how a human autovaccine against PSM can be developed through modification of the molecule by insertion of one or more promiscuous foreign T cell epitopes to reveal a panel of immunogenised PSM molecules.

The constructs will be tested for their ability to induce specific CTL responses against PSM bearing tumour cells. Furthermore, the constructs will be tested for their ability to induce antibodies which are cross-reactive with the native parts of the PSM molecule. Subsequently, in several in vitro assays and in vivo animal models the efficacy of the different constructs will be evaluated. The induced antibodies will be tested for their ability to activate complement via the classical pathway and to initiate ADCC via Fc-receptors.

Finally, the different molecules will be tested in animal models of human prostate cancer.

Strategy in Designing a PSM Autovaccine

Briefly, the PSM vaccination plan entails the following experimental tasks.

Design and Production of a Panel of Human PSM Mutants
  Cloning of the PSM sequences from human and rat/mouse.
  Mutational work to generate immunogenized hPSM molecules.
  Expression of wild type and immunogenized hPSM molecules in E. coli and/or Pichia pastoris and/or mammalian cells and/or insect cells (such as the $S_2$ cell line).
  Purification, refolding and characterization of the immunogenized hPSM molecules.

DNA Vaccination Against PSM
  Generation of hPSM DNA vaccination vectors encoding immunogenized hPSM molecules.
  Testing of hPSM vaccination vectors in in vitro and in vivo experiments.

Selection of hPSM Candidates
  Immunizations of mice/rabbits.
- ELISA.
- FACS analysis.
- In case of antibody response: Tumor cell proliferative assay.
- T cell assays.

Testing of the HPSM Mutants In Vivo

Solid tumor/metastasis model in mice.

Conceptual Study: CTL Induction by Autovaccination

- Construction of immunogenized mouse/rat PSM corresponding to the selected hPSM candidates (e.g. in the form of DNA vaccines).
- Testing the immune response raised by mouse/rat PSM mutants in in vitro assays: Immunochemical assays, ELISA, FACS analysis, cellular assays, complement lysis of PSM bearing cells, ADCC assay, CTL activity assay, Tumor cell proliferative assay, T cell presentation assays.
- Testing of the mPSM mutants in vivo in a solid tumor/metastasis model in mice.

Nomenclature of the hPSM Constructs

PSM is a type II membrane protein of 750 amino acids, cf. SEQ ID NO: 2 which sets forth the wild-type sequence with the exception that Gly substitutes Trp in position 2 due to the introduction of an NcoI site and a Kozak sequence in SEQ ID NO: 1, where ggt substitutes tgg in positions 4–6. However, native PSM (i.e. PSM having a Trp in position 2) has also been used for some human PSM based autovaccine constructs.

In PSM, the extracellular part constitutes the 707 C-terminal amino acids, whereas the cytoplasmic domain is predicted to be 19 amino acids long and the transmembrane part of the protein consists of 24 amino acids (aa 20–43).

As starting point for the constructs, the splice variant PSM' has also been used. Our version of this splice variant has the amino acid sequence corresponding to residues 58–750 in SEQ ID NO: 2. For ease of nomenclature, the regions in PSM' are numbered according to the numbering in PSM (meaning that e.g. region 2 consists of amino acids 87–108 in PSM and amino acids 30–51 in PSM), cf. also the below discussion of the regions.

All the genetic constructs of human PSM are designated hPSM_(or hPSM'_ if PSM' is used as a starting point), where the first_ is the insertion region used for insertion of P2, and the second_ is the insertion region used for P30. If P2 or P30 is not present in the protein, the number 0 (zero) is designated. The full length wild type hPSM is designated hPSM0.0 and the wild type hPSM lacking the cytoplasmic and transmembrane parts is designated hPSM)0.0. The 13 planned immunogenized hPSM genes which all contain one P2 epitope and one P30 epitope will be named hPSM1.1, hPSM6.1, hPSM8.1, hPSM10.1, hPSM1.6, hPSM1.8, hPSM1.10, hPSM1.2, hPSM1.3, hPSM1.5, hPSM2.1, hPSM3.1, hPSM10.3, hPSM6.3, hPSM'10.3, hPSM'6.3, hPSM8.3, hPSM'8.3, and hPSM5.1, cf. details below.

In hPSM1.1, both the P2 and the P30 epitopes are inserted in tandem in insertion region no. 1 (the membrane spanning region). Theoretically, this mutant, hPSM1.1, can be considered a very attractive vaccine candidate for induction of antibody production, because the whole extracellular domain of this molecule is intact. For induction of CTL responses using nucleic acid immunization, constructs such as hPSM10.3 and hPSM6.3 are considered useful.

In order to facilitate the cloning and mutagenesis procedures, much of the molecular construction work is done using either the N-terminal (amino acids 1–436) or the C-terminal (amino acids 437–750) part of the hPSM gene as starting material. These two parts of the hPSM gene are designated hPSMI_ and hPSMII_, respectively, where the first_ is the insertion region used for insertion of P2, and the second_ is the insertion region used for P30. Again, if P2 or P30 is not present in the protein, the number 0 (zero) is designated, and the wild types are named hPSMI0.0 and hPSMII0.0, respectively. A special variant of hPSMI0.0 without the cytoplasmic part of hPSM is designated hPSMI) 0.0.

Practically, most mutagenesis work is being done using hPSMI0.0 and hPSMII0.0 as starting material.

The expressed hPSM mutant proteins will be designated PROS_, where the first_ is the insertion region used for insertion of P2, and the second_ is the insertion region used for P30. If P2 or P30 is not present in the protein, the number 0 (zero) is designated. The wild type hPSM is designated PROS0.0. PROSII0.0 is the hPSM amino acids 437–750 protein product. HIS tagged proteins are called HIS-PROS_. As His tags has been used SEQ ID NO: 21 (amino acid sequence shown in SEQ ID NO:22) for expression in yeast and bacteria, whereas SEQ ID NO: 23 (amino acid sequence shown in SEQ ID NO: 24) has been used for expression in mammalian cells.

Cloning of the Human PSM Sequence

The LNCaP cell line which originates from a metastatic lesion of human prostatic adenocarcinoma was purchased from the American Type Culture Collection (ATCC). mRNA was isolated from this cell line and reverse transcribed using a standard kit in order to obtain cDNA encoding the human PSM sequence. Using different sets of hPSM specific primers, PCR products encoding PSM(437–750) was obtained and further cloned into pUc19 (plasmid number pMR300) and verified by DNA sequencing. This C-terminal part of wild type PSM is designated hPSM part II (hPSMII0.0).

Similarly, the wild type hPSM partI (hPSMI0.0) has been cloned into pUc19 using primers for amplifying partI both with (hPSMI0.0) and without (hPSMI)0.0) the transmembrane+cytoplasmic domains. The clones were control sequenced and hPSMI0.0 and hPSMII0.0 were fused using ligation at the EcoRI site. The resulting clones of hPSM0.0 (SEQ ID NO: 2) and hPSM)0.0 have been subcloned into a number of pro- and eucaryotic expression vectors and again sequence verified. The intracellularly expressed form of human PSM (designated hPSM' —amino acids 58–750 of SEQ ID NO: 2) has also been constructed using the cDNA as starting material. This sequence has also been subcloned into mammalian expression vectors and has been used as starting material for some hPSM autovaccine constructs, e.g. hPSM'0.3 and hPSM'6.3.

Cloning of the Rat and Mouse PSM Sequences

Two EST (expressed sequence tag) clones containing murine PSM cDNA sequences (from fetal murine kidney and murine macrophages, respectively) were purchased from American Type Culture Collection (ATCC), 10801 University Boulevard, Manassas, Va. 20110-2209. Together, these EST's covered the mouse PSM CDNA sequence, and thus both full length mouse PSM (SEQ ID NO: 7 and 8) as well as murine PSM' (SEQ ID NO: 9 and 10) were subcloned into bacterial vectors and mammalian expression vectors. Murine PSM AutoVac constructs have also been made by insertion of P30 into the mouse PSM cDNA.

Expression of wild type HPSM in e. Coli

The C-terminal part (amino acids 437–750) of hPSM, hPSMII0.0, has been cloned into the bacterial expression vector pET28b in order to obtain a product with an N-terminal poly-histidine (HIS) tail which facilitates easy large scale purification and identification with anti-poly-HIS antibodies. The protein product of poly-HIS tagged hPSMII0.0 (protein product designated HIS-PROSII0.0) was expressed in E. coli.

The DNA encoding the truncated wild-type human PSM hPSM)cyt0.0 has also been expressed from pET28b in the E. coli strain BL21(DE3) where the expression product is located in inclusion bodies. SDS-PAGE analysis of bacterial lysate showed a product with the expected migration and Western blotting with rabbit anti-HIS-PROSII0.0 also gave the expected band. Further, N-terminal sequencing of five amino acids of this product eluted from an SDS-PAGE gel gave the expected amino acid sequence.

The wild type hPSM constructs hPSM0.0, hPSM)0.0 (as well as two hPSM mutants, hPSM1.1 and hPSM6.1, see below) have been cloned into different E. coli expression vectors in order to enable a more efficient expression and some degree of folding of the recombinant proteins in E. coli. The chosen expression systems are:

pMCT6 which generates N-terminally His-tagged versions of the expressed recombinant proteins, pGH433 which express the recombinant proteins in connection to a 22 amino acid pelB leader sequence which should direct the protein to the periplasmic space of the E. coli bacteria, and pMal-p2 in which recombinant proteins are expressed as C-terminal fusions to maltose binding protein (MBP) containing the natural MBP periplasmic leader sequence. Antibodies against MBP can be used for detection of the fusion proteins and a carbohydrate coupled column can be used for affinity purification of the product.

However, E. coli expression experiments of the wild type hPSM proteins from these vectors only showed a fair expression level from pMCT6. The problems of getting periplasmic expression of the wild type hPSM proteins are still not solved at present.

Expression of Wild Type hPSM in Pichia Pastoris

Because of the relatively high molecular weight of the PSM protein and its relatively high degree of glycosylation (app. 16% of the molecular weight) and in order to facilitate purification by elimination of the refolding step, it has been decided to implement alternative technology for eukaryotic expression of the recombinant proteins. Several well-characterized eukaryotic expression systems have been evaluated, and for the initial screening of hPSM mutants, the yeast Pichia pastoris has been chosen as alternative to E. coli expression.

An expression system based on the yeast Pichia pastoris has been applied on PSM constructions. The glycosylation pattern of recombinant proteins expressed in this organism is expected to resemble the mammalian glycosylation patterns more than e.g. Saccharomyces cerevisiae due to a lesser branched mannosylation of the recombinant protein. It has been shown that mannose receptor-mediated uptake of antigens by dendritic cells results in an approximately 100-fold more efficient presentation to T cells compared to fluid-phase endocytosed uptake. Therefore, mannosylation might play a role for the antigenicity (and especially the ability to induce CTL responses) of the hPSM mutants and other antigens against which a CTL response is desirable.

A strain of Pichia pastoris as well as two different expression vectors have been purchased from Invitrogen. The vector pPICZ∀A carries a methanol inducible promoter upstream of the polycloning site, whereas the pGAPZ∀A vector express proteins constitutively. Both vectors encode the ∀-factor secretion signal in order to export the recombinant proteins to the medium. The selection system of these vectors is zeocin resistance. The sequences encoding hPSM0.0, and hPSM)0.0 (as well as one hPSM mutant, hPSM1.1, cf. below) were subcloned into these vectors (in-frame with a C-terminal c-myc identification epitope, SEQ ID NO: 27 (amino acid sequence shown in SEQ ID NO: 28)).

Four Pichia pastoris strains (X-33, SMD1168, GS115, and KM71) differing e.g. in their growth requirements were transformed with each of these (linearized) plasmids using electroporation. The transformation procedure was repeated several times with minor changes in order to obtain a large number of zeocin resistant clones. Expression of wild type hPSM)0.0 (as well as hPSM1.1, see below) was obtained in the Pichia pastoris system. The expressed products could be detected in Western blotting of lysates of Pichia pastoris transformants both using an anti-hPSM monoclonal antibody and an anti-c-myc monoclonal antibody as primary. However, the recombinant products were detected intracellularly.

Expression of Wild Type HPSM in Mammalian Cells

An expression system using CHO (chinese hamster ovary) cells will also be implemented for the final testing and production of selected molecules.

So far, CHO cells have been transfected with wild type hPSM and hPSM1.1 with/without in frame leader sequences in mammalian expression vector pcDNA3.1. Geneticin resistant cells have been obtained. In COS cells transiently transfected with the same constructs, both hPSM0.0 and hPSM1.1 was detected in Western Blotting of cell pellets using anti-hPSM monoclonal antibody.

Tissue Distribution of hPSM

A commercial kit has been purchased in order to determine whether hPSM expression can be detected in various human tissues including prostate, blood and brain. The method is based on a dot blot detection of polyA containing mRNA extracted from 50 different human tissues. Preliminary results do not indicate hyperexpression of hPSM in tissues such as blood or brain. However, after the priority date of the resent application, others have demonstrated the presence of PSM in other tissues, cf. above.

Design of the hPSM Mutants

When designing the mutational work in PSM, some regions of the protein are very important to preserve in the modified constructs, for example potential and identified T cell epitopes, B cell epitopes and disulfide bridge cysteine residues. Therefore, such "forbidden" regions have been identified within the PSM sequence leaving a limited number of "open" regions of 20 amino acids or more available for exchange with the foreign T helper epitopes P2 and/or P30. Per definition, the transmembrane region is also considered an "open" region since autoantibodies directed against this region are irrelevant and elimination of this sequence is believed to enhance the solubility of the mutated PSM proteins but it cannot be excluded that this region contain important CTL epitopes, hence the preservation of the transmembrane region in e.g. hPSM10.3.

According to our expectation that the autovaccine will induce a CTL response, it would be important to identify and preserve potentially subdominant CTL epitopes in the constructs. Two such epitopes are already known from the literature: 1) the peptide comprising LLHETDSAV, which is amino acids 4–12 of PSM (SEQ ID NO:1), can be presented on the human MHC class I molecule HLA-A2.1 (Tjoa 1996), and 2) the peptide comprising ALFDIESKV, which is amino acids 711–719 of PMS (SEQ ID NO:1), also binds HLA-A2.1 (ref 25). We have also searched the PSM amino acid sequence in order to identify primary anchor residues of HLA class I binding motifs as described by Rammensee et al. (Rammensee, 1995) for the most abundant HLA class I types (HLA-A1, HLA-A2, HLA-A3, KLA-A23, HLA-A24 and HLA-A28), together constituting 80% of the HLA-A types of the human population. Likewise, potential HLA-B and HLA-C epitopes have been identified and designated as "forbidden" areas.

Because the initial intention was to use C57/black×SJL F1 hybrid mice in case it was decided to use transgenic mice for testing the PSM autovaccine constructs, certain potential mouse H-$2^b$ and H-$2^s$ T helper epitopes have been identified and considered "forbidden" regions (Rammensee 1995).

It is also important to preserve known antibody binding regions in the PSM molecule, because they could be important in the induction of specific anti-PSM autoantibodies. Five such regions have already been described: PSM (63–68), PSM(132–137), PSM(482–487) (WO 94/09820), PSM(716–723) and PSM(1–7) (Murphy, 1996). Using the computer based method of Hopp and Woods for prediction of antigenic determinants, five regions are predicted: PSM (63–69), PSM(183–191), PSM(404–414), PSM(479–486) and PSM(716–723) (Hopp 1983), some of these overlapping the experimentally found B cell epitopes. These regions will also be preserved in the PSM vaccine candidate molecules.

The PSM protein contains 4 cysteine residues (amino acid positions 22, 196, 466 and 597) which will be preserved in the immunogenized constructs because of their potential importance in the formation of disulfide bridges.

Based on the above mentioned "forbidden" and "open" regions in the hPSM protein, 10 regions suitable for insertion of foreign T helper epitopes were identified:

Insertion Regions in hPSMI (from Initiation Site to EcoRI Site, aa 1–437):

Region 1: aa 16–52 in PSM (4 aa preceding TM, TM (24 aa) and 9 aa after TM=37 aa)

Region 2: aa 87–108 in PSM, aa 30–51 in PSM' (22 aa)

Region 3: aa 210–230 in PSM, aa 153–173 in PSM' (21 aa)

Region 4: aa 269–289 in PSM, aa 212–232 in PSM' (21 aa)

Region 5: aa 298–324 in PSM, aa 241–267 in PSM' (27 aa)

Insertion Regions in hPSMII (from EcoRI Site to Termination Site, aa 437–750):

Region 6: aa 442–465 in PSM, aa 385–408 in PSM' (24 aa)

Region 7: aa 488–514 in PSM, aa 431–457 in PSM' (27 aa)

Region 8: aa 598–630 in PSM, aa 541–573 in PSM' (33 aa)

Region 9: aa 643–662 in PSM, aa 586–605 in PSM' (20 aa)

Region 10: aa 672–699 in PSM, aa 615–642 in PSM' (28 aa)

The insertion regions as well as the "forbidden" regions are represented graphically in FIG. 4.

A number of different immunogenized PSM constructs will be made by substitution of a segment of amino acids from two of the above listed insertion regions with P2 or P30. Each mutant protein will thus contain both P2 and P30, although such constructions are only exemplary—single-mutants are also within the scope of the present invention. Experimentally, the mutations will be made in clones of hPSMI and hPSMII cDNA respectively, and the two mutated parts will subsequently be combined by ligation (at the EcoRI site). The P2 and P30 epitopes have initially been inserted into insertion regions 1, 2, 3, 5, 6, 8 and 10 in order to create the mutants.

The sequences of P2 and P30 are:

P2: QYIKANSKFIGITEL (SEQ ID NO: 12, 15 aa), in this case encoded by the nucleotide sequence cag tac atc aaa gct aac tcc aaa ttc atc ggt atc acc gag ctg (SEQ ID NO: 11, 45 nucleotides), where the sequence in boldface is a SacI site. Other codon choices may occur, depending on choice of cloning vector and expression system P30: FNNFTVSFWLRVPKVSASHLE (SEQ ID NO: 14, 21 aa), in this case encoded by the nucleotide sequence ttc aac aac ttc acc gta agc ttc tgg ctg cgt gtt ccg aaa gtt agc gCT AGC cac cta agaa (SEQ ID NO: 13, 63 nucleotides), where boldface indicates W an HindIII site, single underlining indicates an Eco47III site, capital letters indicates a BstNI site, and double underlining indicates an NheI site.

The following table summarizes the human PSM constructs used herein:

| Construct | P2 position in protein | P30 position in protein |
|---|---|---|
| hPSM0.0 | ) | ) |
| hPSM)0.0 | ) | ) |
| hPSM' 0.0 | ) | ) |
| hPSM1.1 | 17–31 | 32–52 |
| hPSM6.1 | 448–462 | 21–41 |
| hPSM8.1 | 606–620 | 21–41 |
| hPSM10.1 | 674–688 | 21–41 |
| hPSM1.6 | 24–38 | 443–463 |
| hPSM1.8 | 24–38 | 607–627 |
| hPSM1.10 | 24–38 | 673–693 |
| hPSM1.2 | 24–38 | 87–107 |
| hPSM1.3 | 24–38 | 210–230 |
| hPSM1.5 | 24–38 | 301–321 |
| hPSM2.1 | 91–105 | 21–41 |
| hPSM3.1 | 213–227 | 21–41 |
| hPSM5.1 | 305–319 | 21–41 |
| hPSM8.0 | 606–620 | ) |
| hPSM10.0 | 674–688 | ) |
| hPSM0.1 | ) | 21–41 |
| hPSM1.0 | 24–38 | ) |
| hPSM6.3 | 448–462 | 210–230 |
| hPSM8.3 | 606–620 | 210–230 |
| hPSM10.3 | 674–688 | 210–230 |
| hPSM' 6.3 | 391–405 | 153–173 |

-continued

| Construct | P2 position in protein | P30 position in protein |
|---|---|---|
| hPSM' 8.3 | 549–563 | 153–173 |
| hPSM' 10.3 | 617–631 | 153–173 |

Molecular Constructions of the hPSM Mutants

Mutations to insert P2 and P30 encoding sequences have been performed using both hPSMI0.0 and hPSMII0.0 as starting material.

In order to generate a majority of the hPSM mutants, P2 and P30 were initially inserted in hPSMI0.0 at insertion position 1. The resulting material (hPSMI1.0 and hPSMI0.1, respectively) was subsequently used as starting material for mutagenesis to insert P2 and P30 at positions 2,3 and 5 and for ligation with epitope mutated hPSMII. hPSMI1.0 was constructed using SOE (single overlap extension) PCR and subsequently sequence verified. hPSMI0.1 was constructed using the "Quick Change" technique and subsequently sequence verified.

The P2 epitope was inserted into positions 2, 3 and 5 of hPSMI1.0 using SOE-PCR to create hPSMI1.2, hPSMI1.3 and hPSMI1.5. These constructions were combined with hPSMII0.0 to create hPSM1.2, hPSM1.3 and hPSM1.5.

hPSMI2.1, hPSMI3.1 and hPSMI5.1 were constructed by SOE PCR using hPSMI0.1 as starting material. This material has been assembled with hSPMII0.0 by ligation at the EcoRI site in order to create the full length mutants hPSM2.1, hPSM3.1 and hPSM5.1.

The P2 epitope was inserted at three different positions of hPSMII0.0 in order to create hPSMII6.0, hPSMII8.0 and hPSMII10.0 using the "Quick Change" technique, and these clones were subsequently sequence verified.

Subsequently, hPSMI0.1 was ligated with hPSMII6.0, hPSMII8.0 and hPSMIII0.0 to obtain hPSM6.1, hPSM8.1 and hPSM10.1, and the clones were sequence verified.

Insertion of the P30 epitope in hPSMII is presently being done to generate hPSMII0.6, hPSMII0.8 and hPSMII0.10 using SOE PCR.

hPSM1.1 was constructed using two two-step PCR mutations followed by ligation in a HindIII site within the epitope sequence. The full length construct is sequence verified.

hPSM10.3, hPSM'10.3, and hPSM6.3 have been constructed using SOE-PCR. Several other hPSM variants with both P2 and P30 inserted in the extracellular part of hPSM are currently being constructed (hPSM'6.3, hPSM8.3, hPSM'8.3).

In addition to the originally contemplated mutants each containing both P2 and P30, four mutants which only contain a single foreign epitope have been constructed and sequence verified: hPSM1.0, hPSM8.0, hPSM10.0 and hPSM0.1.

Expression of hPSM Mutants in *E. coli*

In small-scale experiments, seven hPSM mutants, hPSM1.1, hPSM6.1, hPSM8.1, hPSM10.1, hPSM2.1, hPSM3.1 and hPSM5.1 were expressed from pET28b in the *E. coli* strain BL21(DE3), and IPTG inducible products of the expected size were identified on Coomassie Blue stained SDS-PAGE gels. However, a product of hPSM1.1 was not detectable. The expression levels of these hPSM mutants were very low compared to the product of the wild type construct hPSM)0.0. At this point, a fair expression level of the hPSM mutants using the pET system in *E. coli* seems impossible, and the use of other *E. coli* expression systems and/or other host organisms is thus necessary.

As mentioned above, hPSM6.1 and hPSM1.1 have been subcloned into different *E. coli* expression vectors in order to generate

- N-terminally His-tagged versions of the expressed recombinant proteins using vector pMCT6,
- versions of the proteins expressed with the pelB leader sequence which directs the protein to the periplasmic space of the *E. coli* bacteria using vector pGH433, and
- versions of the recombinant proteins expressed as a C-terminal fusion protein to maltose binding protein (MBP) using vector pMal-p2.

So far, a sufficient expression level from any of these constructs has not been obtained.

Since hPSM0.0 is fairly expressed in *E. coli* while a similar expression level of full length hPSM0.0 or the hPSM mutants has not been observed, it is possible that presence of the cytoplasmic part of the hPSM molecule can somehow "inhibit" the expression of the full-length hPSM constructs in *E. coli*. To test this hypothesis, we initially made two genetic constructs of hPSM1.1 and hPSM6.1 without cytoplasmic domains. However, in *E. coli* expression experiments there were only weak expression of these)cyt gene products.

Expression of hPSM Mutants in *Pichia Pastoris*

In order to express the hPSM1.1 mutant protein from the yeast *Pichia pastoris*, the hPSM1.1 sequence has been subcloned (in-frame with a C-terminal c-myc identification epitope, SEQ ID NO: 27) into the two different expression vectors pPICZVA and pGAPZVA, and the sequences have been verified. hPSM1.1 expression (as well as hPSM)0.0, see above) was detected intracellularly in the *Pichia pastoris* transformants.

Expression of hPSM Mutants in Mammalian Cells

As mentioned above, hPSM1.1 has been subcloned into the mammalian expression vectors pcDNA3.1(+) and pZeoSV2 and these constructs (and others) could be used for expression in e.g. CHO cells. Transient expression of hPSM1.1 as well as hPSM0.0 has been obtained in COS cells as verified by Western blotting.

DNA Vaccination

DNA vaccination would, if effective, be very well suited for the PSM autovaccine—especially because this administration form has been shown to promote both CTL mediated immune reactions and antibody production. Therefore, it was the intention to perform a parallel study with the aim of investigating the effect of DNA-vaccination of mice with appropriate vectors encoding immunogenized mouse ubiquitin and/or mouse TNF∀. DNA vaccination with hPSM (and/or mutants) encoding naked DNA will also be done.

Feasibility Study Using Immunogenized Ubiquitin for DNA Vaccination

A feasibility study stating the effect of DNA vaccination with an immunogenized self protein was performed using ubiquitin with an inserted T helper epitope from ovalbumin (UbiOVA) as a model protein. Sequences encoding UbiOVA as well as wild type ubiquitin were subcloned into the mammalian expression vector pcDNA3.1(−).

Groups of 5 BALB/c mice were immunized with 40:g pcDNA-UbiOVA or pcDNA-ubiquitin construct either intramuscularly in the quadriceps or intradermally. An control control group of received UbiOVA protein in complete Freunds adjuvant. Three and six weeks later, the immunizations were repeated with the only difference that the UbiOVA protein was emulsified in incomplete Freunds adjuvant.

The mice were bled regularly and the anti-ubiquitin antibody titers were determined. In the DNA vaccinated UbiOVA groups, only very weak anti-ubiquitin antibody titers were obtained. Subsequently, all groups were boosted with UbiOVA protein in incomplete Freunds adjuvant and bled in order to determine whether DNA vaccination with UbiOVA (and not ubiquitin) could potentiate the antibody response towards UbiOVA protein. The results of this experiment showed that there was no significant difference between the UbiOVA groups and the control groups, all mice developed strong anti-ubiquitin antibodies upon this single UbiOVA/FIA boost.

DNA Vaccination Using hPSM Constructs

Currently, various DNA vaccination experiments are ongoing using hPSM constructs. Various human PSM wild-type and AutoVac constructs (such as e.g. hPSM0.0, hPSM) 0.0, hPSM'0.0, hPSM1.1, hPSM10.3) have been subcloned into DNA vaccination vectors (such as pcDNA3.1(+), pcDNA3.1(-), pVAX and pZeoSV2). In some of the constructions, different leader sequences (such as the CD11a, tPA, and IL-5 leader sequences; nucleotide SEQ ID NOS: 29, 25, and 31, and amino acid SEQ ID NOS: 30, 26, and 32, respectively) have been included directly N-terminally and in-frame to allow secretion of the expressed hPSM proteins in vivo. All the constructions in DNA vaccination vectors have been verified by DNA sequencing and in vitro translation.

Mice of different strains (such as Balb/cA, Balb/cJ, DBA/2 and A/J) have been injected with the above described hPSM DNA vaccines either intradermally or intramuscularly and boosted several times using the same constructs.

Serum samples have been obtained during the immunisation period and stored at −20° C. These samples will be analysed for presence of antibodies reactive with wild type hPSM.

Also, assays to monitor CTL and T helper proliferative responses in these mice are being established.

Preliminary results suggest that induction of both CTL as well as antibody responses against PSM can be accomplished.

Purification/Characterization of his-Tagged hPSM (437–750) (HIS-PROSII0.0)

HIS-tagged wild type hPSMII (HIS-PROSII0.0) was expressed from pET28b, and solubilized inclusion bodies were applied to a gel filtration FPLC column and eluded in a buffer containing 8 M urea. Fractions predominantly containing hPSMII were subjected to various refolding conditions to optimize the procedure. Solubilized product dialyzed against a Tris buffer was estimated to be more than 90% pure using silver-stained SDS-PAGE.

Rabbits were immunized with the purified HIS-PROSII0.0 in order to use the resulting antiserum for later detection and possibly affinity purification of the hPSM mutants.

Purification/Characterization of Soluble hPSM (Pros)0.0)

Wild type hPSM lacking the cytoplasmic and transmembrane parts, PROS)0.0, has been expressed in the *E. coli* strain BL21(DE3) upon induction with IPTG and could be detected in inclusion bodies. SDS-PAGE of this bacterial lysate followed by Western blotting with rabbit anti-HIS-PROSII0.0 showed a product with the expected migration. N-terminal sequencing of the first five amino acids of this product eluted from an SDS-PAGE gel showed the expected sequence corresponding to human PSM. The product was subjected to a large series of solubilization and refolding experiments. A product which stay in solution can be obtained in a Tris buffer without denaturant or reductant, but SDS-PAGE analysis reveals that the material probably forms large aggregates. Mice and rabbits have been immunized with this material in order to get antibody against hPSM e.g. for analytical purposes—the antisera did not react with LNCap hPSM.

A batch of washed *E. coli* inclusion bodies of PROS)0.0 has been prepared for immunization of rabbits to generate a polyclonal antiserum against PSM. Approximately 50% of the protein content in the wet pelleted material contained was PROS)0.0. The antisera did not react with LNCap hPSM in Western blotting.

Preparation of KLH-Conjugated hPSM Peptides for Immunization

Three 15-mer peptides were synthesized in order to make an immunogenic conjugate of known hPSM B cell epitopes with an immunological carrier molecule to obtain a polyclonal antiserum which is able to recognize hPSM. These peptides contain the PSM B cell epitope plus 5–6 flanking PSM amino acids in each end.

The peptides were made by automatic synthesis, HPLC purified and control-sequenced using Edman degradation.

A chemically linked conjugate was prepared by cross-linking the B cell epitope containing hPSM peptides KLH using a standard 1-step procedure with glutaraldehyde as the cross-linking agent.

Synthesis of P2 and P30 Peptides with Flanking hPSM Sequences

Six peptides have been designed which correspond to the P2 and P30 epitopes with 5 flanking hPSM amino acids in each end. The flanking amino acids correspond to the epitope insertion sites 6, 8 and 10. The peptides will be used in e.g. T cell proliferation assays, but also for other purposes such as ELISA or other in vitro assays. The peptide sequences are:

| | |
|---|---|
| PSMpep007 | P2 inserted in hPSM insertion position 6 QERGV<u>QYIKANSKFIGITEL</u>RVDCT (SEQ ID NO: 15) |
| PSMpep008 | P2 inserted in hPSM insertion position 8 AVVLR<u>QYIKANSKFIGITEL</u>EMKTY (SEQ ID NO: 16) |
| PSMpep009 | P2 inserted in hPSM insertion position 10 MFLER<u>QYIKANSKFIGITEL</u>HVIYA (SEQ ID NO: 17) |
| PSMpep010 | P30 inserted in hPSM insertion position 6 NSRLL<u>FNNFTVSFWLRVPKVSASHLE</u>VDCTP (SEQ ID NO: 18) |
| PSMpep011 | P30 inserted in hPSM insertion position 8 VVLRK<u>FNNFTVSFWLRVPKVSASHLE</u>SFDSL (SEQ ID NO: 19) |
| PSMpep012 | P30 inserted in hPSM insertion position 10 LMFLE<u>FNNFTVSFWLRVPKVSASHLE</u>PSSHN (SEQ ID NO: 20) |

The P2 and P30 epitopes are underlined. The peptides were made by automatic synthesis and subjected to the process of HPLC purification followed by control-sequencing using Edman degradation.

Immunogenicity Assays

Different experimental setups have been initiated in order to produce materials and establish immunogenicity assays for the future testing of and selection between the mutated PSM constructs.

Generation of Polyclonal Rabbit Anti-His-PROSII0.0 and Anti-KLH-PSM-Peptide Conjugate Antisera Two rabbits were immunized with purified HIS-PROSII0.0, the HIS-tagged C-terminal part of the hPSM protein (amino acids 437–750) emulsified 1:1 with complete Freunds adjuvant and boosted twice (at days 28 and 55) with the same antigen emulsified in incomplete Freunds adjuvant.

Two rabbits were immunized with a cocktail consisting of the KLH-PSM peptide conjugate plus each of the three free peptides. These three peptides each contain a previously defined B cell epitope of hPSM. The cocktail was emulsified 1:1 with complete Freunds adjuvant. The rabbits were boosted twice (at days 28 and 55) with the same antigen emulsified in incomplete Freunds adjuvant.

Cross-reactivity between anti-HIS-PROSII0.0 and PSMpep005 and cross-reactivity between anti-KLH-PSM peptide conjugate plus peptides and HIS-PROSII0.0 was demonstrated in ELISA assays. The anti-HIS-PROSII0.0 antibody has the ability to recognize native hPSM in lysates of LNCaP cells in Western blotting.

Immunization of Mice with Retrovirally Expressed hPSM0.0

At this stage of the PSM project, a serious obstacle is still the lack of antibodies which are able to recognize correctly folded native hPSM. Therefore, an immunization experiment using retrovirally expressed hPSM0.0 was performed.

Six groups of Balb/c mice were immunized with either: 1) mitomycin C treated BALB/c fibrosarcoma cells (79.24.H8) transduced with hPSM0.0 cDNA (CMV-Koz-hPSM), 2) mitomycin C treated BALB/c fibrosarcoma cells (79.24.H8), transduced with empty vector (CMVBipep), 3) packaging cells (BOSC) transfected with hPSM0.0 cDNA (CMV-Koz-hPSM), 4) packaging cells (BOSC) transfected with empty vector (CMVBipep), 5) retrovirus stock expressing hPSM0.0 cDNA (CMV-Koz-hPSM) or 6) retrovirus stock, empty vector (CMVBipep).

At several time points, the mice were bled and the sera obtained tested for reactivity in ELISA for reactivity against HIS-PROSII0.0. Unfortunately, none of the mice developed antibodies able to specifically recognize the HIS-PROSII0.0 preparation.

Establishment of an Anti-hPSM ELISA

Purified HIS-PROSII0.0 was used for coating polystyrene microtitre plates (Maxisorp) for the purpose of establishing an ELISA assay for testing e.g. hybridoma supernatants or mouse and rabbit antisera. Sera from BALB/c mice immunized with the same preparation of HIS-PROSII0.0 were reactive with the immobilized HIS-PROSII0.0 at 0.5:g per well using horse radish peroxidase labelled rabbit anti-mouse Ig as secondary antibody.

As mentioned above, the ability of an antiserum raised in rabbits against KLH-PSMpep004—PSMpep005—PSMpep006 conjugate mixed with the free peptides to react with immobilized HIS-PROSII0.0 was demonstrated using this ELISA assay.

Using AquaBind® microtitre plates (cf. the disclosure in WO 94/03530 describing i.a. microtitre surfaces coated with tresyl-activated dextran which are now marketed under the registered trademark AquaBind), an ELISA using immobilized PSM peptides (PSMpep004, PSMpep005 and PSMpep006) was established. AquaBind® plates coated with these peptides could detect a rabbit antiserum raised against the same preparation of antigen. As mentioned above, rabbit anti-HIS-PROSII0.0 could be detected on AquaBind® plates coated with PSMpep005.

Establishment of an Anti-hPSM Western Blot Using LNCaP Cells and Monoclonal Antibody 7E11C5

7E11C5 B cell hybridomas which secrete mouse IgG2a monoclonal antibody against an intracellular epitope of human PSM was purchased from ATCC. Culture supernatant from approximately 90% dead cells was collected and used in Western blotting for detection of human PSM in both membrane enriched preparations of LNCaP cells as well as in LNCaP cell lysates. This antibody was purified using protein G columns, and its reactivity with LNCaP in Western blotting verified.

Establishment of a FACS Method to Detect hPSM on LNCaP Cells

We have established to mutually independent FACS methods to detect hPSM on LNCaP cells. Several problems are being addressed: The LNCaP cells grow very slow and in irregular clumps, and therefore the method to prepare single cell suspensions should be optimized. Secondly, the epitope recognized by the mAb 7E11C5 is in the literature defined to be in the cytoplasmic domain of hPSM. Therefore, the method to fix and permeabilize the cells has been developed. For this purpose, protein G purified 7E11C5 antibody has been FITC conjugated and can thus be used without secondary antibody in FACS analysis.

Also, a FACS method using the anti-hPSM monoclonal antibody J591 which recognizes an epitope on the extracellular part of hPSM, has been established. The antibody was obtained from BZL Biologicals and FITC conjugated and subsequently used for FACS analysis and sortings of e.g. LNCaP cells and hPSM transfectants (see below).

Establishing a Cytotoxicity Assay

A method to purify dendritic cells from mouse bone marrow has been implemented. Using model proteins, immunization of mice with dendritic cells pulsed with model class I peptides and protein has been optimized. Also, mice have been immunized with a model protein (3-galactosidase) formulated in the form of ISCOMS. T-cells purified from immunized mice have been in vitro restimulated with different forms of the corresponding antigens. The ability of these restimulated CTLs to lyse different kinds of target cells (including pulsed dendritic cells as well as transfectants expressing retrovirally expressed cytosolic class I peptide) was subsequently measured. Two different in vitro assays measuring CTL activity have been established, using either chromium release or and DNA fragmentation (JAM method) as measures of cytotoxicity. Very nice results were obtained with the ∃-galactosidase model protein and with various combinations of MHC class I and class II binding model peptides.

Establishment of Tools to Study Breaking of Autotolerance Towards Mouse Psm in Mice It is the intention to study whether autotolerance to mouse PSM can be broken in mice by immunisation and/or DNA vaccination against murine PSM using murine PSM AutoVac molecules.

As mentioned above, cDNA encoding murine PSM (mPSM) has been obtained and DNA sequenced. Four mPSM variant molecules are being generated by insertion of P30 at well-defined sites in either full length mPSM or mPSM'. The constructs are as follows:

| mPSM amino acids substituted with P30 | Length of molecule (no. of amino acids) |
|---|---|---|
| mPSM0.0 | ) | 752 |
| mPSM' 0.0 | ) | 694 |
| mPSMX | 255–271 (of SEQ ID NO: 8) | 756 |
| mPSMY | 689–700 (of SEQ ID NO: 8) | 760 |
| mPSM' X | 197–213 (of SEQ ID NO: 10) | 698 |
| mPSM' Y | 631–642 (of SEQ ID NO: 10) | 702 |

Initially, the mPSM wild type and analogue molecules are subcloned into DNA vaccination vectors and used for DNA vaccination of mice.

It is the intention to analyse immune responses such as CTL responses and tumor elimination in the mice. For this, murine tumor cell lines will be transfected with wild type murine PSM (fused in-frame with an identification tag, e.g. the c-myc epitope, SEQ ID NO: 27, for detection purposes).

In Vivo PSM Tumor Models

Mouse T Cell Proliferation Assays with P2 and P30

A series of T cell proliferation experiments has been conducted in order to establish the T cell immunogenicity of P2 and P30 peptides in various mouse strains (BALB/cA (H-$2^d$), C3H/Hen (H-$2^k$), DBA/1 (H-$2^q$) and C57BL/6 (H-$2^b$)). It is well known that these epitopes are promiscuous in humans, but the T cell promiscuity also needed to be confirmed in mice using M&Es experimental setup. It was thus shown that P30 is T cell immunogenic in the BALB/cA and C57BL/6 strains whereas neither P2 or P30 were shown to be T cell immunogenic in the C3H/Hen strain. In DBA/1, T cells could be raised against P2.

Generation of hPSM Expressing Mouse Tumor Cells

For the use of a hPSM specific tumor model in mice as well as for the use in tumor cell proliferative assays, a panel of hPSM expressing mouse tumor cells are being established.

One approach is to generate these cell lines by transducing the murine tumor cell lines with retroviral vectors encoding the full-length wild type hPSM0.0 cDNA.

Three different constructs encoding full length wild type cDNA encoding human PSM inserted into the polycloning site of the retroviral vector CMVBipep was constructed, two of these containing a short Kozak sequence upstream of the start codon.

These constructs were transduced into three different mouse tumor cell lines: P815 (mastocytoma, H-$2^d$), B16–F10 (melanoma, H-$2^b$) and 79.24.H8 (fibrosarcoma, H-$2^d$) using the BOSC packaging cell line. Geneticin resistant clones have been obtained for all three cell types, and it was verified in PCR analysis on genomic DNA template that the retroviral constructs were integrated in the host cells. It has not yet been possible to detect an expressed PSM gene product in Western blot or FACS analysis using the 7E11C5 monoclonal antibody.

Two stable mouse tumor cell lines harboring membrane bound wild type human PSM have been established by transfection. This was done using hPSM0.0 cDNA subcloned in the mammalian expression vector pcDNA3.1( )) under the control of the CMV promoter and containing a Kozak sequence upstream of the start codon.

The resulting plasmid was transfected into two different mouse tumor cell lines: 79.24.H8 (fibrosarcoma, Balb/c derived) and Sa1N (fibrosarcoma, A/J derived). Geneticin resistant cultures were obtained and subjected to Western blotting and FACS analysis using the J591 and 7E11C5 anti-hPSM monoclonal antibodies. Using the J591 antibody, the cells were FACS sorted several rounds until a hPSM positive population was obtained. hPSM expression was again verified by intracellular FACS staining using the 7E11C5 antibody. It was also checked by FACS analysis that the MHC class I expression levels were the same level as the levels of the parental cell lines.

Cultures of 79.24.H8 and Sa1N cell lines expressing hPSM were cloned by limiting dilution. Several clones were obtained and tested for different hPSM expression levels by FACS analysis using the anti-hPSM monoclonal antibody J591.

79.24.H8 cells expressing hPSM were transfected with the gene encoding B7.1 for use in e.g. in vitro assays to monitor hPSM specific CTL responses and/or interferon-gamma release. The cells were FACS sorted one time using an anti-B7.1 antiserum.

Establishment of a hPSM Specific Tumor Model in Mice

It has been decided to establish at least two in vivo tumor models in immune competent mice in order to determine the anti-tumor effect of antibodies raised in mice against the immunogenized hPSM molecules. This will hopefully be done by injecting syngeneic mouse tumor cell lines modified to express wild type hPSM on the surface membrane. Cells which form solid tumors and/or cells which are known to metastasize will be used. Cell lines which can be implanted in syngeneic mice without being rejected due to the presence of the foreign hPSM molecule will be used in the model. The ability of the hPSM vaccines to eliminate such tumor cells will be used for the selection of the hPSM vaccine candidates.

To evaluate the growth of Sa1N cells transfected with the full length human PSM, different doses ($2\times10^6$ and $5\times10^6$) of the hPSM transfected Sa1N cells (S-PSM, sorted 5 times) were injected subcutaneously at the lower right flank of groups of A/J mice. However, solid tumors did not establish. Subsequently, three clones of S-PSM cells with different expression level of hPSM were injected subcutaneously in 3 groups of A/J mice at a dose of $10^7$ cells/mouse. The sizes of the established tumors were measured with a caliber measuring two different diameters which were multiplied to give the tumor size in mm$^2$. These values were compared for the three groups. Within 3–6 days, all mice developed a solid tumor-like structure which disappeared again approximately by day 15. This is likely to be due to the presence of human PSM on the tumor cell surfaces, although it has not yet been verified. Sa1N cells transfected only with the pcDNA3.1 vector continued to grow as solid tumors in mice.

A similar picture was observed in mice injected with $10^6$, $5\times10^6$, or $10^7$ 79.24.H8 cells transfected with hPSM and sorted several rounds for hPSM expression. These cells (termed 79-PSM) also did not establish as tumors in Balb/c nor DBA/2 mice. However, when a clone of hPSM transfected 79.24.H8 cells, 79-PSM.3, was injected into Balb/c or DBA/2 mice, the mice developed solid tumor-like structures which disappeared again by day 10–20. Vector-transfected 79.24.H8 continued to grow in Balb/c mice.

It still remains to be evaluated if these "tumors" are treatable, or if a better tumor model can be established based on the described S-PSM and 79-PSM cell lines and clones.

Conclusions

In the molecular construction work we have succeeded in cloning of the human PSM gene and obtaining the mouse PSM cDNA. An array of fully sequenced immunogenized hPSM autovaccine constructs have been produced. The hPSM mutants as well as different wild type hPSM molecules have been expressed in E. coli, and it was found and verified that the expression level in E. coli is very low. Polyclonal antibodies against the C-terminal half of hPSM have been induced in rabbits. Efforts have been made in order to implement different expression tags (His-tag and maltose binding protein fusion) as well as expression systems alternative to E. coli inclusion bodies. Recombinant wild type and/or autovaccine hPSM has been detected in transfected Pichia pastoris and mammalian cells. Useful considerations regarding the DNA vaccine technology have been made, and a preliminary feasibility study was performed. DNA vaccination experiments with hPSM autovaccine molecules are ongoing and show promising preliminary results. Different in vitro assays useful for testing of and selection between the mutated PSM constructs is established, including immunochemical assays and FACS analysis. Mouse tumor cells have been stably transfected with full length wild type hPSM and FACS sorted for hPSM surface expression. Clones of these cell lines have been obtained. In vivo xenogenic tumor models in mice is being evaluated using these hPSM bearing syngeneic mouse tumor cells. An array of T cell proliferation assays have been performed in order to select the mouse strains for the tumour models. CTL assays are being optimized, and convincing results with model antigens have been obtained using different immunization methods and assay conditions. Furthermore, tools necessary to study breaking of tolerance to mouse PSM by immunization against mouse PSM autovaccines are being established.

EXAMPLE 2

Production of a Her2 Autovaccine

A human autovaccine against Her2 can be developed through modification of the molecule by insertion of one or more promiscuous foreign T cell epitopes to reveal a panel of immunogenised Her2 molecules. These modified proteins will be tested for their ability to induce antibodies which are cross-reactive with the native parts of the Her2 molecule. Subsequently, in several in vitro assays and in vivo animal models, the efficacy of the different constructs (as may be the case with the DNA vaccination) and modified proteins will be evaluated. The induction of specific CTL responses against Her2 bearing tumour cells will be analysed. Also, the induced antibodies will be tested for their ability to activate complement via the classical pathway and to initiate ADCC via Fc-receptors. Finally, the different modified molecules will be tested in animal models of human breast cancer to examine their effects on the treatment of tumours.

Immunogenic rat and human molecules will be constructed with promiscuous T-cell epitopes at different positions in the molecule.

During vaccination against the entire extracellular domain of Her2 there is a possibility of some degree of cross reaction of the antibodies with other EGFr receptors since some of these receptors are homologous by up to 40–46% in the extracellular domains. Therefore it is planned that the conserved regions of Her2 would be disrupted by inserting foreign T cell epitopes at least in some of the modified proteins (see below for details).

Regions of Her2 that may potentially be CTL or B-cell epitopes are avoided in designing of constructs are seen in FIG. 3. The rationale for using these positions is as follows:

The human Her2 sequence can be divided into a number of domains based solely on the primary structure of the protein.

Extracellular (Receptor) Part:
1–173: Domain I (N-terminal domain of mature polypeptide).
174–323: Domain II (Cysteine rich domain, 24 cysteine residues).
324–483: Domain III (ligand binding domain i the homologous EGF receptor).
484–623: Domain IV (Cysteine rich domain, 20 cysteine residues).
624–654: Transmembrane domain (TM resudues from 654–675).

Intracellular (Kinase) Part:
655–1010: Tyrosine kinase domain (core TK domain from 725–992).
1011–1235: C-terminal domain.

Selection of sites in the amino acid sequence of HER2 to be displaced by either the P2 or P30 human T helper epitopes has been done considering the following parameters (loosely prioritised):
1. Known and predicted CTL epitopes
2. Homology to related receptors (EGFR in particular)
3. Conservation of cysteine residues
4. Predicted loop, ∀-helix and ∃-sheet structures
5. Potential N-glycosylation sites
6. Prediction of exposed and buried amino acid residues
7. Domain organisation The CTL epitopes appear to be clustered in domain I, domain III, the TM domain and in two or three "hot spots" in the TK domain. According to the invention, these should be largely conserved.

Regions with a high degree of homology with other receptors are likely to be structurally important for the "overall" tertiary structure of Her2, and hence for antibody recognition, whereas regions with low homology possibly can be exchanged with only local alterations of the structure as the consequence.

Cysteine residues are often involved in intramolecular disulphide bridge formation and are thus crucial for the tertiary structure and should preferably not be changed. Regions predicted to form ∀-helix or ∃-sheet structures should preferably be avoided as insertion points of foreign epitopes, as these regions are probably important for the folding of the protein.

Potential N-glycosylation sites should preferably also be conserved because mannosylation of the protein (for example by expression in yeast) is desired, cf. the presence of mannose receptors on APCs.

Regions predicted (by their hydrophobic properties) to be interior in the molecule preferably should be conserved as these could be involved in the folding. In contrast, solvent exposed regions could serve as candidate positions for insertion of the model $T_H$ epitopes P2 and P30.

Finally, the domain organisation of the protein has also been taken into consideration because of its relevance for protein structure and function.

The focus of the strategy has been to conserve the structure of the extracellular part of Her2 as much as possible, because this is the part of the protein which is relevant as target for neutralising antibodies. By contrast, the intracellular part of native membrane bound Her2 on the surface of cancer cells is inaccessible for the humoral immune system.

Hence, only the presence of CTL epitopes gives reason to include this part in a vaccine. It is therefore obvious to place one or more epitopes here. If it turns out that it is impossible to express the full length Her22 molecule in E. coli or in yeast, the intracellular part could be truncated after the first CTL epitope "hot spot" (around position 800). Additional CTL epitopes can hereafter be added to the C-terminal end of the truncated molecule.

The transmembrane region probably is an independent folding unit and substitution of this with $T_H$ epitopes such as P2 or P30 will probably not affect the HER2 structure and folding. In addition, the TM domain might cause great problems for the expression in yeast and coli and should in any case be susbstituted. Thus, an epitope should preferably be placed in this domain in all constructions (perhaps leaving it intact in 1 construction as it contains several CTL epitopes and because it is somehow involved in transmission of signals upon ligand binding).

The extracellular domain could principally be kept intact by placing P2 and P30 in the intracellular and transmembrane domains, thereby maximising the number of potential B-cell epitopes and interfering as little as possible with the structure. However, the high degree of homology to EGFR and Her-3 and Her-4 make a risk for cross reactivity to these receptors which may (or may not) be undesirable. In addition, some monoclonal antibodies have been described which function as agonists for the receptor (perhaps by stimulating heterodimerisation or ligand binding) and increase tumour size, in vivo. Positions in the extracellular domain have therefore been selected which thereby hopefully will reduce these risks.

This selection has involved all of the before mentioned parameters and has been based on two different assumptions: (i) Insertion in non-conserved (with respect to related receptors) regions will help to maintain the tertiary structure and might reduce unwanted activation by antibodies. (ii) Insertion in the well conserved regions can alter the structure, but might at the same time reduce the risk of cross reactivity by destroying the most related sequences. Both assumptions are speculative, but as it is very difficult to predict the effect of placing an epitope in any position of the protein some of these positions have been included in the constructions.

It has been speculated that it could be an advantage to remove the two cysteine rich domains completely. These are predicted to form solvent exposed loop structures and could form independent folding units perhaps involved in dimerisation (as indicated by the many cysteines that could serve to keep a rigid structure necessary to form a dimerisation domain). Deleting these structures might therefore eliminate the risk of activation by antibodies as well as reduce the number of cross reacting antibodies as these domains are the most well conserved of the extracellular part of the protein. In addition, such cysteine risch domains could be problematic to produce in *E. coli* or yeast cells.

The details of constructs are as follows using the P2 and P30 epitopes as non-limiting examples: the P2 epitope will primarily be placed in the extracellular domain of Her2 in combination with the P30 epitope substituting part of or all of the membrane spanning region. The P2 epitope will be placed in regions based on the criteria discussed above. The preferred constructs have the following structures:

| Construct name | Position of P2 | Position of P30 | Length |
|---|---|---|---|
| hHER2MA2-1A | 59–73 | 632–652 | 795 |
| hHER2MA2-2A | 103–117 | 632–652 | 795 |
| hHER2MA2-3A | 149–163 | 632–652 | 795 |
| hHER2MA2-4A | 210–224 | 632–652 | 795 |

-continued

| Construct name | Position of P2 | Position of P30 | Length |
|---|---|---|---|
| hHER2MA2-5A | 250–264 | 632–652 | 795 |
| hHER2MA2-6A | 325–339 | 632–652 | 795 |
| hHER2MA2-7A | 369–383 | 632–652 | 795 |
| hHER2MA2-8A | 465–479 | 632–652 | 795 |
| hHER2MA2-9A | 579–593 | 632–652 | 795 |
| hHER2MA2-1B | 59–73 | 661–675 | 795 |
| hHER2MA2-2B | 103–117 | 661–675 | 795 |
| hHER2MA2-3B | 149–163 | 661–675 | 795 |
| hHER2MA2-4B | 210–224 | 661–675 | 795 |
| hHER2MA2-5B | 250–264 | 661–675 | 795 |
| hHER2MA2-6B | 325–339 | 661–675 | 795 |
| hHER2MA2-7B | 369–383 | 661–675 | 795 |
| hHER2MA2-8B | 465–479 | 661–675 | 795 |
| hHER2MA2-9B | 579–593 | 661–675 | 795 |
| hHER2MA2-1Y | 59–73 | 710–730 | 795 |
| hHER2MA2-2Y | 103–117 | 710–730 | 795 |
| hHER2MA2-3Y | 149–163 | 710–730 | 795 |
| hHER2MA2-4Y | 210–224 | 710–730 | 795 |
| hHER2MA2-5Y | 250–264 | 710–730 | 795 |
| hHER2MA2-6Y | 325–339 | 710–730 | 795 |
| hHER2MA2-7Y | 369–383 | 710–730 | 795 |
| hHER2MA2-8Y | 465–479 | 710–730 | 795 |
| hHER2MA2-9Y | 579–593 | 710–730 | 795 |
| hHER2MA2-Z | 695–709 | 710–730 | 795 |
| hHER2MA2-C | 653–667 | 632–652 | 795 |
| hHER2MA2-BX | 695–709 | 661–675 | 795 |
| hHER2MA2-AX | 695–709 | 632–652 | 795 |
| hHER2MA2-4E | 210–224 | 5–25 | 795 |
| hHER2MA2-6E | 325–339 | 5–25 | 795 |
| hHER2MA2-8E | 465–479 | 5–25 | 795 |
| hHER2MA5-4D | 210–224 | 632–652* | 666 |
| hHER2MA5-6D | 325–339 | 632–652* | 666 |
| hHER2MA5-8D | 465–479 | 632–652* | 666 |
| hHER2MA6-C | 653–667 | 632–652 | 702 |

Position of the epitope indicates the first and the last amino acid position of the epitope relative to the start point of mature Her2. Length is the length in amino acids of the complete construct. In all constructs except those were position is indicated with *, the epitope substitutes an amino acid strecth of the same length as the epitope. "*" Indicates that the epitope is inserted rather than substituted into Her2. All constructs listed above are therefore truncates of mature Her2, where the omitted part is from the C-terminus.

Most of the constructions exist in different versions, e.g. in pcDNA3.1+vector in fusion with the natural HER2 signal peptide sequence, in the vector pMT/BiP/V5-His-A as a fusion with the BiP leader peptide for expression in *Drosophila* cells and without leader sequence in the pET28b vector for expression in *E. coli* cells.

Below are described the models that are intended for use in the screening and selection of modified Her2 proteins.

1. Induction of antibodies in transgenic rat Her2 mice and in rabbits to rat and human Her2, respectively, will be investigated by conventional ELISA technology after at least three immunisations. Commercially available antibodies to human and rat Her2 will be used as positive controls.
2. These rabbit antibodies will be used to study the putative inhibition of growth of human and transgenic mouse tumour cells overexpressing Her2 in an in vitro model.
3. T cell proliferation of PBL from tetanus immunised patients towards selected human Her2 molecules will be investigated by conventional methods.
4. The ability of modified rat Her2 molecules to induce CTL responses in rat Her2 transgenic mice will be studied using tumours from these mice as targets.
5. It is intended to synthesise a selected set of peptides in the transmembrane region of human Her2 encompassing P2 and P30 epitopes. These peptides will be tested in proliferation of PBL from humans previously immunized with tetanus toxoid to determine whether P2 and P30 epitopes could be efficiently processed out from within the Her2 sequences and presented to T cells.

6. It is quite possible that selected human modified Her2 proteins will be tested to generate neutralising antibodies in a mouse that has been genetically constructed to only expresses human VDJ genes. Such a mouse is available from Abgenix, Fremont, Calif., U.S.A. as a collaboration.

Four well-characterised transgenic mouse models for breast cancer that contains rat Her2 oncogene have been described. The first three transgenic mice express activated Her2 oncogene while the fourth model utilises inactivated Her2. All models utilise an MMTV promoter to drive expression in mammary glands.

We have decided to use two transgenic mice models: 1) a more aggressive tumour model described by Muller et al using activated Her2 oncogene (Muller et al, 1989) and 2) a less aggressive tumour model in which inactivated Her2 is used to create focal mammary tumours with long latency (Guy et al, 1992). Both transgenic mice are purchased from Jackson and/or Charles Rivers Laboratories.

In the initial experiments, these mice are allowed to produce antibodies and CTL responses by immunising and boosting with modified rat Her2 proteins. Incidence of tumours will then be investigated as described by others (Muller et al, 1989; Guy et al, 1992; Katsumata et al, 1995). Antibody levels will be measured by an ELISA assay. The CTL activity would be determined by generating target cells expressing rat Her2 as mentioned above.

Alternatively, the nude mouse xenograft carcinoma model can be used for passive vaccination experiments. Nude mice can be transplanted with human tumours and inhibition of tumours could be attempted with passive transfer of serum from normal or humanised mice immunised with modified Her2 proteins. While this would be useful for studying the role of antibody in suppressing tumours, CTL activity cannot be directly measured in this system.

In the second in vivo model, tumours in mice would also be generated by transplanting cells lines from tumours of transgenic mice described above. Cell lines generated from these mice would be transferred into relevant mouse strain and localisation established using standard protocols.

Transfer of mouse tumours cells over expressing rat Her2: In this system, cells will be transfected with rat genes and transferred into MHC compatible mice. Inhibition of tumour growth would be achieved by generating anti-Her2 responses.

In these systems; modified Her2 proteins would be used as vaccine in adjuvants to generate antibodies and CTL responses.

DNA vaccination has been used successfully in several systems to mount an effective immune response. We are currently investigating means of DNA delivery using modified self proteins. It is our intention to utilise DNA vaccination approach to determine effects of modified Her2 constructs in inhibiting tumours in transgenic mouse models of breast cancer. Similar approach can than possibly be applied in humans for the treatment of this disease.

EXAMPLE 3

Production of an Anti-FGF8b Vaccine

In the following it will be described how a human autovaccine against FGF8b can be developed through modification of the molecule by insertion of one or more promiscuous foreign T cell epitopes to reveal a panel of immunogenized "FGF8b" molecules. The constructs will be tested for their ability to induce antibodies that are cross-reactive with the authentic parts of the FGF8b molecule. Subsequently, in several in vitro assays and in vivo animal models the efficacy of the different constructs will be evaluated. The induced antibodies will be tested for their ability to activate complement via the classical pathway and to initiate ADCC via Fc-receptors. Finally, the different molecules will be tested in animal models of human prostate and breast cancers.

Construction of an Autovaccine Against FGF8b

Due to the complete identity of the murine and human FGF8b polypeptides, all constructs can be used for experiments in both humans and mice.

The promiscuous tetanus toxoid T helper cell epitopes P2 and P30 used with success in the human TNFV vaccine will be inserted into the FGF8b polypeptide. Due to the small size of FGF8b, constructs will be made with one epitope per molecule.

Other promiscuous T helper cell epitopes such as the influenza haemagglutinin epitope HA(307–319) and other T-cell epitopes discussed herein could also be considered (O'Sullivan 1991).

4 different immunogenized FGF8b constructs have been made, with the epitopes distributed along the molecule. These four constructs are made on the basis of multiple and pairwise alignments of the FGF family of proteins. A pairwise alignment of FGF2 and FGF8b is used as basis for an analysis of the presumed secondary structure (i.e. beta-sheet distribution) along the FGF8b molecule. The residues that are conserved between FGF2 and FGF8b does not cluster anywhere on the three-dimensional structure, which indicates that there are no particular regions of the molecule that cannot be replaced without having deleterious effects on the folding capabilities. The amino acid residues in FGF2 that align to the cysteine residues in FGF8b are positioned very close to each other three-dimensionally, indicating that they form a disulfide bond in FGF8b, and that the alignment is correct. The flexibility of the N-terminal part of FGF2 was also considered.

The variant of FGF8b with the P30 epitope in the N-terminal (F30N) was designed on the basis of no-gap alignments of the amino acid residues of the FGF8b protein and the P30 epitope (SEQ ID NO: 14), and scoring the different positions with regard to chemical properties of every amino acid residue.

Only the region N-terminally of the predicted beta-barrel structure was considered. In the case of F30N, there are 9 similar out of 21 residues. Using this pseudo-algorithm, the substitutions would be expected to result in minimal overall structural changes. The sequences of the four different constructs, as well as three-dimensional representations of the replaced amino acids are shown in FIG. 6.

The variant of FGF8b with the P2 epitope (SEQ ID NO: 12) in the C-terminal (F2C) was initially designed as F30N. There is, however, predicted a good Kd epitope at positions 195–203. Therefore, the P2 epitope is inserted just C-terminal of this epitope. Again, only the region C-terminal of the predicted beta-barrel was considered.

The internal variants of FGF8b (F30I and F2I) were constructed by replacing external loops in the FGF2 structure with the epitopes P30 and P2, respectively, whereby the beta-barrel structural backbone of the FGF structure presumably will remain unchanged.

The immunogenized FGF8b molecules have been expressed in *Eschericia coli*, which facilitates large scale production of the proteins at minimal costs. Although, FGF8b contains two potential N-glycosylation sites (Asn31 and Asn177), bacterially expressed recombinant FGF8b has been shown to be biologically active (MacArthur 1995a, Blunt 1997). In order to facilitate purification and refolding, the FGF8b variants have been produced in a His-tagged version, thereby rendering coupling to a Ni-charged column possible.

Purification of the molecules has been performed utilizing the high positive charge of the protein molecules or the His-tag, and refolding will be performed using standard procedures taking the formation of the disulfide bridge into account.

The four immunogenized molecules have also together with the wild type FGF8b cDNA been inserted into DNA vaccination vectors.

Screening and Selection of the Modified FGF8b Molecules

The four immunogenized FGF8b molecules have been expressed in bacteria and subsequently purified from inclusion bodies. In parallel, the constructs will be used as DNA vaccines. The different constructs will then be compared for their ability to induce various effects, which are desired in the treatment of prostate and breast cancer patients. Such investigations will be performed using several different in vitro and in vivo assays. Finally, the results of the experiments will form the basis for the ultimate selection of one or two candidates for a FGF8b vaccine in humans.

In Vitro Models

Analyses in the Murine System

Mice of different haplotypes as well as rabbits will be immunized with the different FGF8b constructs in Complete Freund's Adjuvant and subsequently boosted at least twice with the same antigens emulsified in Incomplete Freunds Adjuvant. Thus, the ability of the different constructs to break B-cell tolerance can be compared. DNA vaccination will be performed on other animals using purified DNA in Complete Freund's Adjuvant/Incomplete Freund's Adjuvant injected intra muscularly with 14 day intervals.

Serum samples will be obtained at several time points during the immunization schedule, and the ability of the different constructs to induce FGF8b specific antibodies will be determined using a conventional ELISA method (Rochon 1994). A commercial polyclonal antiserum, as well as a commercial monoclonal antibody raised against FGF8b (R&D), would be used for positive controls. The FGF8b protein is commercially available (R&D) but will also be produced along with the other FGF8b constructs and subsequently purified/refolded. This product can then be used for coating of plates in a direct ELISA for testing the sera from mice/rabbits immunized with FGF8b variant proteins.

A valuable tool for investigating the effects of vaccinating against FGF8b will be a FGF8b dependent cancer cell line. Several FGF8b positive cancer cell lines, e.g. MCF-7 or SC-3, are described in the literature. Such a FGF8b dependent murine cancer cell line will be identified using quantitative RT-PCR, cell proliferation experiments, and STAT-3 phosphorylation assays.

The presence of FGF8b ligated to a FGF receptor on the cell surface will be detected with FGF8b specific antibodies in FACS or ELISA analysis. Antibodies directed against several of the different FGF receptors are commercially available (R&D).

The constructs will be compared with respect to their ability to induce antibodies capable of activating complement lysis of FGF8b producing/bearing cells. This can be detected with one of the mouse tumor cell lines expressing FGF8b described earlier or, alternatively using osmotically FGF8b-loaded cells. Sera from normal or transgenic mice (see below) immunized with the human FGF8b constructs will be incubated with the cell line and subsequently incubated with fresh guinea pig complement. Antibody mediated complement lysis of the cells can be detected by standard procedures. The ability of the induced antibodies to mediate ADCC can be studied by measuring the 51Cr-release from labeled FGF8b expressing cells. The effector cells will be PBMC from syngeneic mice. For establishing the assay, it may be convenient to use a mouse cell line capable of mediating ADCC (positive for Fc(-receptors) as effector cell with an antibody against human FGF8b.

In order to show that the FGF8b candidate vaccines do not somehow promote autoantibody induced tumor growth we will also perform a tumor proliferation assay. Serum samples from immunized mice will be incubated with FGF8b expressing tumor cells. Proliferation of the tumor cells can then be detected by their ability to incorporate 3H-thymidine, which subsequently is added to the cells.

Since FGF8b is known to induce proliferation of a range of mammalian cells, it will also be necessary to examine the growth promoting effects of the variant proteins. This can be done using cell proliferation assays as the one used by Marsh 1999.

The biological effect of FGF8b on mammalian cells should be neutralized by the autoantibodies. This can be demonstrated by using recombinant FGF8b and e.g. NIH3T3 in cell proliferation (and morphology changes) studies. Addition of the autoantibodies should abolish the transforming activity of FGF8b.

Immunization Protocol

The number of animals that are to enter a FGF8b AutoVac immunization experiment must depend on the expected penetrance of the disease in the model, and thus, the numbers needed to obtain statistically significant information. The immunization protocol must be based on the experience we have from the TNFa AutoVac project. Various immunization protocols have been used for immunizing mice with the various TNFa analogs for specific purposes, but most experiments were performed using the following protocol:

1. The mice should be individually marked either by earmarks or with transponders, 10 animals in each cage. Presumably, males and females must be evaluated separately, but in any case, we will not have both sexes in the same cage. The animals should be left to rest at least 3 days after transport and marking.
2. Antigen 1 mg/ml in PBS buffer was emulsified with an equal volume Freunds complete antigen (CFA) (Difco or Sigma). The emulsion is checked by placing a drop of the emulsion on a water surface and it is observed whether the drop holds together or disperses. Mixing is maintained until the drop does not disperse.
3. The standard immunization dose is 100:g antigen in a 100:1 volume+100:1 of adjuvant. Thus, the total immunization volume is 200:1, administered s.c. (sub cutaneously) over the back of the animal.
4. Boostings are performed 2–3 weeks after the primary immunization, and subsequently at 2–3 week intervals. The boosting/immunization material is prepared and administered exactly as the immunization material, but Freunds incomplete adjuvant is used. Probably three boosts will induce the maximal titer. Thus, the highest titers will be obtained 6–9 weeks after the first immunization.

5. Bleedings are orbital bleeds of 50–100: 1 usually taken before the first immunization and one week after each boosting. Tail bleeds can also be used, and 10–20: 1 can be sufficient for titre determinations.

The initiation point of the immunization program will depend on the development of the disease, and the strategy we want to adopt. Initially, we suggest that it is attempted to generate the maximal immunity as soon as possible, but it is difficult to start immunizations sooner than at approx. 5 weeks of age. Hereafter, high titres should be maintained by boosting at 6–8 week intervals, after the three initial boosts. There is a potential problem if the FGF8b is necessary for the normal development of the young mouse, and therefore one could argue in favor of starting the immunizations later in the adult mouse.

Analyses in the Human System

In the selection between the different FGF8b constructs the ability of human antigen presenting cells to present the inserted immunogenic T cell epitopes to human T cells will be investigated. This will be done by using the same in vitro processing assays for P2 and P30 presentation that were used for the TNFa vaccine. Human T cell lines, which are specific for P2 and P30, will be established from donors vaccinated against tetanus. Antigen presenting cells (PB-MCs) from the same donors will be incubated with the different constructs and T cell lines will be added. The level of presentation of the inserted T cell epitopes can then be compared by measuring the stimulation of the T cell lines.

In Vivo Animal Models

At least three different systems can be used to monitor whether the induced FGF8b antibodies are capable of controlling a FGF8b dependent in vivo effect.

Mice will be transplanted with murine FGF8 expressing tumor cells, and inhibition of tumor progression will be assayed with autovaccination using the modified FGF8b proteins or FGF8b DNA vaccines. The ideal system involves the use of cells isolated from murine tumors. Alternatively, we will use other murine cell lines (e.g. Balb/3T3) stably transfected with the FGF8b cDNA in an expression vector.

The mouse xenograft carcinoma model will be used for passive vaccination experiments. Nude mice will be transplanted with human tumors, and inhibition of tumors would be attempted with transfer of serum from normal or humanized mice immunized with modified FGF8b proteins or FGF8b DNA vaccines. This would be very useful for studying the ability of the raised antibodies to suppress tumors.

Another approach to achieve proof of concept will involve the use of mice transgenic for FGF8b. These mice, that are carrying the FGF8b cDNA under control of the very specific mouse mammary tumor virus (MMTV) promoter, are shown to spontaneously develop FGF8b expressing mammary tumors (Coombes personal communication). Autovaccination of these mice with the FGF8b variant proteins or FGF8b DNA vaccines would enable us to show if the autovaccine will enable the mice to suppress or reject the tumors.

A possible approach to obtain proof of concept would be to use the Wnt-1 transgenic mice (MacArthur 1995c). Induction of breast cancers by MMTV virus is reported to activate FGF8 expression in more than half of the mice developing tumors. FGF8b-dependency of the tumors, could be established if our autovaccine(s) could suppress the incidence or growth rate of the tumors.

The fact that transgenic mice often show non-physiological immunological tolerance patterns will most likely not affect this project since the FGF8b polypeptides are identical for human and mouse.

When, a beneficial effect of the FGF8b immunizations eventually has been demonstrated in the mouse model and suitable human vaccine candidates have been selected it will be possible to perfom a limited number of toxicology studies. Subsequently, to obtain a final proof of concept, vaccine studies on breast, and prostate cancer patients can be carried out.

Importantly, if the experiments using in vivo models have positive outcome, more mutants will be constructed based on the data available.

EXAMPLE 4

Preparation of MUC-1 Analogue

Only one MUC-1 autovac molecule has been made. This comprises, in total, nine mucin repeats each having the sequence SEQ ID NO: 33. The construction starts with three such sequences, followed by a P2 epitope, followed by three more mucin sequences, followed by a P30 epitope, ended by three mucin sequences.

The construction has been made with and without an N-terminal UNI-his tag (SEQ ID NO: 23). Both variants have been expressed in *E. coli*. The identity of the expressed protein has been confirmed both by Western blotting and N-terminal sequencing. The protein is expressed in soluble form, but as a dimer which is somewhat surprising.

The HIS-tagged MUC-1 molecule has been purified by metal affinity chromatography. The amount of pure protein and the purity is currently unknown.

EXAMPLE 5

Breaking of Autotolerance in a Murine Model System

CTL experiments where mice have been immunised with dendritic cells pulsed with both a class I and a class II epitope have previously shown an enhanced CTL induction when immunising as well as restimulating in vitro with both a class I and a class II peptide compared to an immunisation and re-stimulation with just a class I epitope. This situation is comparable with immunisation with an autovaccine, where a foreign class II epitope is inserted in a self protein. Uptake and processing of these molecules by professional antigen precenting cells such as dendritic cells, leads to presentation of the foreign class II epitope together with some self class I epitopes. It is known that it is possible to elicit autoreactive CTL's, but the presence of a foreign class II helper epitope very likely should enhance this CTL induction.

The potential advantage of the present invention for induction of self reactive CTLs is currently being investigated in ovalbumin transgenic mice. There exist four different transgenic lines with different ovalbumin expression levels and tolerance states, cf. Kurts C et al. 1997, J. Exp. Med. 186: 239–245 disclosing the RIP-mOVA transgenic mouse (expressing ovalbumin in pancreas, kidney and thymus and having a high degree of tolerance) and Kurts C et al., 1998, J. Exp. Med. 188: 409–414 disclosing the RIP-OVA$^{low}$ and RIP-OVA$^{high}$ transgenic mice, having low and high expression of ovalbumin, respectively. The last line, RIP-OVA$^{int}$ which expresses ovalbumin at an intermediary level has been obtained from Dr. William R. Heath, co-author of the two above-mentioned refernces.

In the body there are different degrees of tolerance to different antigens. One of the least degrees of tolerance is found on circulating antigens in large amounts. These antigens will all enter thymus, where self reactive T-cells are deleted. These antigens are under "central tolerance". Tissue specific antigens, on the other hand, do not directly enter the thymus and is generally under "peripheral tolerance", exerted by e.g. T-cell anergy.

Two ovalbumin AutoVac constructs have produced. They both relate to the sequence with accession No: J00845 in EMBL where the sequence from P30 (SEQ ID NO: 14) have been inserted in two different positions.

In construct "OVA 3.1", P30 is inserted in the position that correspond to amino acid nos. 272–292 in ovalbumin. In construct "OVA 3.2", P30 is inserted in the position that corresponds to amino acid nos. 321–341 in ovalbumin. These constructs have been inserted in the vector pVax1 and used for DNA immunisation.

Mice have been immunised intradermally once with 100 ug each of DNA. Three weeks after this immunisation, the spleens were removed and a CTL assay was set up using target cells expressing the dominant ovalbumin epitope SIINFEKL and the scrambled FILKSINE peptide as control. The immunizations provided a clear CTL induction in wild-type C57BL/6 mice—as expected, since both ovalbumin and P30 are foreign in these mice.

We now intend to immunise the 4 lines of ovalbumin transgenic mice with these AutoVac constructs. The RIP-OVA$^{nlow}$, RIP-OVA$^{int}$, and RIP-OVA$^{high}$ express increasing amounts of ovalbumin and have different degrees of tolerance and, as mentioned above, also RIP-mOVA has a high degree of tolerance.

In these 4 lines of transgenic mice, only P30 will be foreign. Ovalbumin is a self-antigen in these mice and this situation will therefore constitute a true autovaccination for CTL induction towards ovalbumin.

Preliminary results obtained in RIP-OVA$^{low}$ mice having the lowest degree of "peripheral tolerance" to ovalbumin demonstrated that both the ovalbumin with inserted P30 and the naturally occurring ovalbumin molecules were capable of inducing CTL responses—it is expected that transgenic mice having higher degrees of tolerance will only be capable of mounting a CTL response against the modified ovalbumin molecules and not the naturally occurring form.

LIST OF REFERENCES

Ago H et al. (1991). J Biochem (Tokyo), 110, 360–3.
Abdel-Nabi H et al. (1992). Sem. Urol. 10, 45–54.
Acevedo et al. (1995), Cancer 76; 1467–1475.
Acevedo et al. (1997), Cancer Detect. Prev. 21; 295–303.
Adelstein S et al. (1991), Science 251: 1223–1225.
Babaian RJ et al. (1994), J. Urol 152, 1952–1955.
Barnard JA et al. (1995) Gastroenterol. 108(2):564–580.
Bier H et al. (1995), Eur. Arch. Otorhinolaryngol. 252(7): 433–9.
Bouchard L et al. (1989), Cell 57(6): 931–36.
Blaber M et al. (1996), Biochemistry 35, 2086–94.
Blunt AG et al. (1997), J Biol Chem 272, 3733–8.
Boring CC et al. (1993), CA Cancer J. Clin. 43: 7–26.
Boucher et al. (1995), Hum. Pathol. 26; 1201–1206.
Callahan R (1996), Breast Cancer Res Treat, 39, 33–44.
Carter RE (1996), Proc. Natl. Acad. Sci. U.S.A., 93, 749–753.
Chang et al., (1981), Fertil. Steril. 36; 659–663.
Chantry A, 1995, J. Biol. Chem. 270(7): 3068–73.
Crossley PH et al. (1996b), Cell, 84, 127–36.
Crossley PH et al. (1995), Development, 121, 439–51.
Crossley PH, Martinez, S. and Martin, G.R. (1996a) Midbrain development induced by FGF8 in the chick embryo. Nature, 380, 66–8.
Dean C et al. (1994), Int. J. Cancer, suppl 8: 103–107.
Dillioglugil Ö et al. (1995), Eur. Urol. 28, 85–101.
Doi et al. (1996), Int. J. Cancer 65; 454–459.
Douglas TH et al. (1995), J. Surg. Oncol. 59(4), 246–250.
Earp HS et al. (1995), Breast Cancer Res. Treat. 35(1): 115–32.
Eccles SA (1994), Invasion Metastasis 14 (1–6): 337–48.
Eppenberger U et al. (1994),. J. Neurooncol. 22(3): 249–54.
Dorkin TJ et al. (1999), oncogene 18: 2755–2761.
Eriksson AE et al. (1993), Protein. Sci. 2: 1274–84.
Fernandez-Teran M. et al. (1997), Dev. Biol. 189, 246–55.
Fujii K et al. (1995), Exp. Cell. Res. 216(1): 261–72.
Furst J et al. (1994), Urol. Res. 22, 107–113.
Furthauer M et al. (1997), Development 124: 4253–64.
Geissler et al. (1997), Lab. Invest. 76: 859–871.
Gemel J et al. (1996), Genomics 35: 253–7.
Ghosh Ak. et al. (1996), Cell Growth Differ 7: 1425–34.
Goldfarb M et al. (1996), Cytokine Growth Factor Rev 7: 311–
Goodnow CC et al. (1988), Nature 334: 676–682.
Goodnow CC et al. (1991), Nature 352: 532–536.
Greenberg N. M. et al. (1995), Proc. Natl. Acad. Sci. USA 92: 3439–3443.
Guy C. T. et al. (1992), Proc. Natl. Acad. Sci, USA 89: 10578–10582.
Heikinheimo M et al. (1994),. Mech Dev, 48: 129–38.
Henttu P and Vihko P (1989), Bioch. Biophys. Res. Comm. 160: 903–910.
Hopp TP and Woods KR (1983), Mol. Immunol. 20: 483–9.
Horoszewicz JSH et al. (1983), Cancer Res. 43: 1803–1818.
Horoszewicz JSH et al. (1987), Anticancer Res. 7: 927–936.
Hoshikawa M et al. (1998), Biochem Biophys Res Commun 244: 187–91.
Husmann I et al. (1996), Cytokine Growth Factor Rev 7: 249–58.
Israeli RS et al. (1994), Cancer Res. 54: 1807–1811.
Israeli RS et al. (1993), Cancer Res. 53: 227–230.
Israeli RS et al. (1994), Cancer Res. 54: 6306–6310.
Jacoby et al. (1984), Adv. Immunol. 35: 157–208.
Johnson RL and Tabin CJ (1997), Cell 90: 979–90.
Kahn D et al. (1994), J. Urol. 152: 1490–1495.
Kapoun AM and Shackleford GM (1997), oncogene 14: 2985–9.
Kettunen P and Thesleff I (1998), Dev Dyn 211: 256–68.
Koga M et al. (1995), J Steroid Biochem Mol Biol 54: 1–6.
Kouhara H et al., (1994), Oncogene 9: 455–62.
Kozak M (1991), J Cell Biol 115: 887–903.
Lapthorn et al. (1994), Nature 369: 455–461.
Lazar et al. (1995), Cancer Res. 55: 3735–3738.
Leek J et al. (1995), British Journal of Cancer 72: 583–588.
Leung HY et al. (1996), Oncogene 12: 1833–5.
Lopes AD (1990), Cancer Res. 50: 6423–6429.
Loric S et al. (1995), Clin.Chem. 41(12): 1698–1704.
Lupu R et al. (1995), Semin. Cancer. Biol. 6: 135–145.
MacArthur C. A. et al. (1995a), Cell Growth Differ 6: 817–25.
MacArthur C. A. et al. (1995b), Development 121: 3603–13.
MacArthur C. A. et al. (1995c), J Virol 69: 2501–7.
Manabe et al. (1985), Gastroenterology 89: 1319–1325.
Marsh SK et al. (1999), Oncogene 18, 1053–1060.

Martin L et al. (1993), J. Immunol. 150(49): 1234–43.
Mattei MG et al. (1995), Mamm Genome 6: 196–7.
McDonnell WM and Askari FD (1996), New Engl. J. Med 334: 42–45.
Meyers EN et al. (1998), Nat Genet 18: 136–41.
Milich DR et al. (1994), J. Immunol. 153(1): 429–435.
Milner PG et al. (1989), Biochem Biophys Res Commun 165: 1096–103.
Miyashita Y et al. (1994), Jpn J Cancer Res 85: 1117–23.
Modjtahedi H et al. (1993a), Br. J. Cancer 67(2): 254–261.
Modjtahedi H et al. (1993b), Cell. Biophys. 22(1–3): 129–46.
Modjtahedi H et al. (1996), Br. J. Cancer 73(2): 228–35.
Moy FJ et al. (1996), Biochemistry, 35: 13552–13561.
Muller WJ et al. (1988), Cell 54(1): 105–115.
Murphy GP et al. (1996), Prostate 28: 266–271.
Murphy GP et al. (1995), Prostate 26: 164–168.
Murphy GP et al. (1995), Anticancer Research 15(4): 1473–1379.
Nguyen L et al. (1990), Clin. Chem. 35: 1450–1455.
Nonomura N et al. (1990), Cancer Res 50: 2316–21.
O'Sullivan D et al. (1991), J. Immunology 147: 2663–9.
Ohnishi Y et al. (1995), Br. J. Cancer 71(5): 969–73.
Ohuchi H et al. (1997a), Development 124: 2235–44.
Ohuchi H et al. (1997b), Mech Dev 62: 3–13.
Ohuchi H et al. (1994), Biochem Biophys Res Commun 204: 882–8.
Payson RA et al. (1996), Oncogene 13: 47–53.
Pillai et al. (1996), FEBS Lett. 387: 23–26.
Pollard M and Luckert PH (1994), Anticancer Res. 14: 901–903.
Prigent SA and Lemoine NR (1992), Progress in Growth Factor Research 4: 1–24.
R&D focus, Drug News, (1996) 5, 21, 9. Rammensee H-G. et al. (1995), Immunogenetics 41: 178–228.
Regelson W (1995), Cancer 76: 1299–1301.
Ries LAG et al. (1996), SEER Cancer Statistics Review, 1973–1993: Tables and Graphs, National Cancer Institute, Bethesda, Md.
Rinker-Schaeffer CW et al. (1995), Genomics, 30(1): 105–108.
Rochon YP et al. (1994), Prostate 25: 219–223.
Rock KL et al. (1996), Vaccine 14: 1560–1568.
Rock KL and Clark K (1996), J. Immunol. 156: 3721–3726.
Rudra-Ganguly N et al. (1998), Oncogene 16: 1487–92.
Salomon DS et al. (1995), Critical reviews in Oncology/Hematology 19: 183–232.
Sato B et al. (1993), J Steroid Biochem Mol Biol 47: 91–8.
Schlegel J et al. (1994), J. Neurooncol. 22(3): 249–54.
Schmitt JF et al. (1996), J Steroid Biochem Mol Biol 57: 173–8.
Sheaff et al. (1996), J. Clin. Pathol. 49: 329–332.
Sherman L et al. (1998), Genes Dev 12: 1058–71.
Shimamura K and Rubenstein JL (1997), Development 124: 2709–18.
Shirai A and Klinman DM (1993), AIDS Res. Hum. Retroviruses 9, 979–983.
Sokoloff M et al. (1996), Cancer 77(9): 1862–1872.
Steinhoff U et al. (1994), Eur. J. Immunol. 24(3): 773–76.
Stevens VC (1986), Ciba Found. Symp. 119: 200–225.
Su SL et al. (1995), Cancer Res. 55: 1441–1443.
Syrigos et al. (1998), Gut 42: 88–91.
Talwar et al. (1976), PNAS 73: 218–222.
Talwar et al. (1994), PNAS 91: 8532–8536.
Tanaka A et al. (1992), Proc Natl Acad Sci USA 89: 8928–32.
Tanaka A et al. (1998), Cancer Research 58: 2053–56.
Tanaka A et al. (1995), FEBS Lett 363: 226–30.
Thomas H et al. (1996), Br. J. Cancer, 73(1): 65–72.
Tjoa B et al. (1996), Prostate 28: 65–69.
Tjoa B et al. (1995), Prostate 27: 63–69.
Tokunaga A et al., (1995), Cancer 75(6 suppl.): 1418–25.
Tosi E et al. (1995), Int. J. Cancer 62(5): 643–50.
Triozzi et al. (1994), Int. J. One. 5: 1447–1453.
Troyer JK et al. (1995), Int. J. Cancer 62: 552–558.
Valone FH et al. (1995), J. Clin. Oncol. 13(9): 2281–92.
Valve E et al. (1997), Biochem Biophys Res Commun 232: 173–7.
van Dam P A et al. J. Clin. Pathol. 1994 47(10): 914–19.
Weiner LM et al. (1995), Cancer Res. 55(20): 4586–4593.
Wright GL Jr et al. (1996), Urology 48: 326–334.
Wu J et al. (1997), J Steroid Biochem Mol Biol 62: 1–10.
Wu X et al., Fan, Z., Masui, H., Rosen, N., Mendelsohn, J. Apoptosis induced by an anti-epidermal growth factor receptor monoclonal antibody in a human colorectal carcinoma cell line and its delay by insulin.
Wynant GE et al. (1991), Prostate 18: 229–241.
Xu X et al. (1998), Development 125: 753–65.
Yamanishi H et al. (1995), J Steroid Biochem Mol Biol 52: 49–53.
Yogeeswaran and Salk (1981), Science 212: 1514–1516.
Yokoyama H et al. (1998), Dev Biol 196: 1–10.
Yoshimura K et al. (1996), Cancer Lett 103: 91–7.
Yoshiura K et al. (1997), Am J Med Genet 72: 354–62.
Young RA and Davis RW (1983), Proc. Natl. Acad. Sci. U.S.A. 80: 1194–1198.
Yule TD (1993), J. Immunol. 151(6): 3057–3069.
Zhang JD et al. (1991), [published erratum appears in Proc Natl Acad Sci USA 88(12):5477], Proc Natl Acad Sci USA 88, 3446–50.
Zhu Z et al. (1995), Int. J. Cancer 62(3): 319–324.
Zhu X et al. (1991), Science 251: 90–3.

What is claimed is:

1. An analogue of human Her2 which is immunogenic in humans, said analogue comprising continuous sequence of the Her2 protein encoded by SEQ ID NO:3 amino acid residue 1 and including at least amino acid residue 654, which is modified with at least one foreign $T_H$ epitope at one or more positions selected from the group consisting of amino acid residues 5–25, 59–73, 103–117, 149–163, 210–224, 250–264, 325–339, 369–383, 465–479, 579–593, 632–652, 653–667, 661–675, 695–709, and 710–730, wherein said at least one or more foreign $T_H$ epitope is present as an insertion or results from a substitution.

2. The analogue according to claim 1, wherein the immunodominant foreign $T_H$ epitope is promiscuous.

3. The analogue according to claim 2, wherein the immunodominant foreign $T_H$ epitope is selected from the group consisting of a natural $T_H$ epitope and an artificial MHC-II binding peptide sequence.

4. The analogue according to claim 3, wherein the natural $T_H$ epitope is selected from the group consisting of a Tetanus toxoid epitope, a diphtheria toxoid epitope, an influenza virus hemagluttinin epitope, and a P. falciparum CS epitope.

5. The analogue according to claim 4, wherein the natural $T_H$ epitope consists of SEQ ID NO: 12 or SEQ ID NO: 14.

* * * * *

UNITED STATES PATENT AND TRADEMARK OFFICE
CERTIFICATE OF CORRECTION

PATENT NO. : 7,005,498 B1 Page 1 of 1
APPLICATION NO. : 09/806703
DATED : February 28, 2006
INVENTOR(S) : Lucilla Steinaa et al.

It is certified that error appears in the above-identified patent and that said Letters Patent is hereby corrected as shown below:

Title Page
Item (75) Inventors:
Fifth inventors name should read:
-- Jesper Haaning --

Item (56) Foreign Patent Documents:
10th listed reference should read:
-- WO    WO 98/56919   A2   12/1998 --

Other Publications:
Page 2, Column 1, line 44 should read:
-- Matzinger, "Graft tolerance...." Nature Medicine vol. 5, Jun. 1999. --
Page 2, Column 1, line 51 should read:
-- Klotz, Theo et al., "Selective Expression...." Cancer, May 15, 1998, Vol. 82. No. 10, pp. 1897-1903. --
Page 2, Column 2, lines 1 and 2 should read:
-- Wagner, Stephen N. et al., "Analysis of ...." Cancer Immunol Immunother (1997) 44: 239-247. --

Column 139, line 50, after "comprising" insert -- a --.

Signed and Sealed this

Tenth Day of October, 2006

JON W. DUDAS
*Director of the United States Patent and Trademark Office*

UNITED STATES PATENT AND TRADEMARK OFFICE
CERTIFICATE OF CORRECTION

PATENT NO. : 7,005,498 B1
APPLICATION NO. : 09/806703
DATED : February 28, 2006
INVENTOR(S) : Lucilla Steinaa et al.

It is certified that error appears in the above-identified patent and that said Letters Patent is hereby corrected as shown below:

Title Page Other Publications:

Page 2, line 23, reference should read
--Weiner, Louis M., et al., "Phase I Trial..." Cancer Research 55, 4586-4593, Oct. 15, 1995.--

Page 2, line 37, reference should read --WÖLFEL, Thomas et al., "A p16ink4a..," Science, Vol. 269, Sep. 1, 1995.--

Page 2, line 43, reference should read --Falk, Kirsten et al., "Pool sequencing of .." Immunogenetics 39: 230-242, 1994.--

Page 2, line 50 reference should read --Moradi, Mark M. et al, "Serum and .." Cancer, Oct. 15, 1993, Vol. 72, No. 8.--

Page 2, line 52, reference should read --Grøndahl-Hansen, Jan et al., "High levels," Cancer Research, 534, 2513-2521, Jun. 1, 1993.--

Signed and Sealed this

Twenty-third Day of January, 2007

JON W. DUDAS
*Director of the United States Patent and Trademark Office*

UNITED STATES PATENT AND TRADEMARK OFFICE
CERTIFICATE OF CORRECTION

PATENT NO. : 7,005,498 B1
APPLICATION NO. : 09/806703
DATED : February 28, 2006
INVENTOR(S) : Lucilla Steinaa et al.

It is certified that error appears in the above-identified patent and that said Letters Patent is hereby corrected as shown below:

At Column 4, Line 10 "IFN-(," should read --IFN-$\gamma$--.

At Column 14, Line 29, "1-0.2H 0.3H 0.4=0.976" should read --1 – 0.2 x 0.3 x 0.4 = 0.976--.

At Column 14, Line 55, "$N_j$" should read --$\varphi_j$--.

At Column 14, Line 64, "$N_1$, $N_2$, and $N_3$" should read --"$\varphi_1$, $\varphi_2$, and $\varphi_3$--.

At Column 14, Line 67, "$B_i$" should read --$\pi_i$--.

At Column 15, Line 7, "$A_j$" should read --$v_j$--.

At Column 15, Line 11, "1-$B_i$" should read --1-$\pi_i$--.

At Column 15, Line 12, "$f_{residual\_i}=(p_i-B_i)/(1-B_i)$" should read --$f_{residual\_i}=(p_i-\pi_i)/(1-\pi_i)$--.

At Column 17, Line 1, "FC(receptor" should read --FC$\gamma$ receptor--.

At Column 17, Line 1, "FC(RI" should read --FC$\gamma$RI--.

At Column 17, Line 26, "interferon ((IFN-()" should read --interferon $\gamma$ (IFN-$\gamma$)--.

At Column 18, Line 33, "integer ∃ 3" should read --integer $\geq$ 3--.

At Column 18, Line 33, "integers ∃ 0" should read --integers $\geq$ 0--.

At Column 18, Line 34, "is ∃ 1" should read --is $\geq$ 1--.

At Column 18, Line 36, "integers ∃ 0" should read --integers $\geq$ 0--.

At Column 18, Line 36, "is ∃ 1" should read --is $\geq$ 1--.

UNITED STATES PATENT AND TRADEMARK OFFICE
CERTIFICATE OF CORRECTION

PATENT NO.        : 7,005,498 B1
APPLICATION NO.   : 09/806703
DATED             : February 28, 2006
INVENTOR(S)       : Lucilla Steinaa et al.

It is certified that error appears in the above-identified patent and that said Letters Patent is hereby corrected as shown below:

At Column 19, Line 28, "integer ∃ 2" should read --integer ≥ 2--.

At Column 21, Line 27, "0.1:g to 2000:g" should read --0.1 µg to 2000µg--.

At Column 21, Line 29, "0.5:g to 1000:g" should read --0.5µg to 1000µg--.

At Column 21, Line 30, "1:g to 500:g" should read --1µg to 500µg--.

At Column 21, Line 31, "10:g to 100:g" should read --10µg to 100µg--.

At Column 21, Line 66, "(-inulin" should read --γ-inulin--.

At Column 22, Line 24, "(-inulin" should read --γ-inulin--.

At Column 22, Line 59, "Fc(receptors" should read --Fcγ receptors--.

At Column 22, Line 61, "anti-Fc(RI" should read --anti-FcγRI--.

At Column 28, Line 18, "∀-fetoprotein" should read --α-fetoprotein--.

At Column 28, Line 35, "∃-catenin" should read --β-catenin--.

At Column 34, Line 5, "TGF-∀" should read --TGF-α--.

At Column 34, Line 8, "TGF-∃" should read --TGF-β--.

At Column 34, Line 13, "Thymosin ∃ 15" should read --Thymosin β 15--.

At Column 34, Line 16, "TNF-∀" should read --TNF-α--.

At Column 35, Line 58, "∀-linked" should read --α-linked--.

At Column 37, Line 9, "hCG∃" should read --hCGβ--.

UNITED STATES PATENT AND TRADEMARK OFFICE
CERTIFICATE OF CORRECTION

PATENT NO.      : 7,005,498 B1
APPLICATION NO. : 09/806703
DATED           : February 28, 2006
INVENTOR(S)     : Lucilla Steinaa et al.

It is certified that error appears in the above-identified patent and that said Letters Patent is hereby corrected as shown below:

At Column 37, Line 22, "common ∀-chain. The ∃-chain" should read --common α-chain. The β-chain--.

At Column 37, Line 23, "∃-chain" should read --β-chain--.

At Column 37, Line 24, "hCG∃" should read --hCGβ--.

At Column 37, Line 34, "TGF∃" should read --TFGβ--.

At Column 37, Line 53, "hCG∃" should read --hCGβ--.

At Column 37, Line 60, "hCG∃" should read --hCGβ--.

At Column 37, Line 62, "hCG∃" should read --hCGβ--.

At Column 37, Line 67, "hCG∃" should read --hCGβ--.

At Column 38, Line 5, "hCG∃" should read --hCGβ--.

At Column 38, Line 18, "hCG∃" should read --hCGβ--.

At Column 38, Line 20, "hCG∃" should read --hCGβ--.

At Column 38, Line 25, "hCG∃" should read --hCGβ--.

At Column 40, Line 12, "Fc(RI" should read --FcγRI--.

At Column 48, Line 2, "5'63'" should read --5' –> 3'--.

At Column 52, Line 2, "hPSM_ (or hPSM'_" should read --hPSM_._ (or hPSM'_._--.

UNITED STATES PATENT AND TRADEMARK OFFICE
CERTIFICATE OF CORRECTION

| | |
|---|---|
| PATENT NO. | : 7,005,498 B1 |
| APPLICATION NO. | : 09/806703 |
| DATED | : February 28, 2006 |
| INVENTOR(S) | : Lucilla Steinaa et al. |

It is certified that error appears in the above-identified patent and that said Letters Patent is hereby corrected as shown below:

At Column 52, Line 28, "hPSMI_ and hPSMII_" should read --hPSMI_._ and hPSMII_._--.

At Column 52, Line 39, "PROS_" should read --PROS_._--.

At Column 52, Line 44, "HIS-PROS_" should read --HIS-PROS_._--.

At Column 52, Line 64, "(hPSMI)0.0)" should read --(hPSMI÷0.0)--.

At Column 53, Line 1, "hPSM)0.0" should read --hPSM÷0.0--.

At Column 53, Line 9, "hPSM'0.3" should read --hPSM'10.3--.

At Column 53, Line 33, "hPSM)cyt0.0" should read --hPSM÷cyt0.0--.

At Column 53, Line 41, "hPSM)0.0" should read --hPSM÷0.0--.

At Column 54, Line 24, "pPICZ∀A" should read --pPICZαA--.

At Column 54, Line 25, "pGAPZ∀A" should read --pGAPZαA--.

At Column 54, Line 27, "∀-factor" should read --α-factor--.

At Column 54, Line 30, "hPSM)0.0" should read --hPSM÷0.0--.

At Column 54, Line 41, "hPSM)0.0" should read --hPSM÷0.0--.

At Column 56, Lines 45-66, ")" should read --÷--.

At Column 58, Line 24, "these)cyt" should read --these ÷cyt gene--.

At Column 58, Line 32, "pPICZ∀A and pGAPZ∀A" should read --pPICZαA and pGAPZαA--.

At Column 58, Line 33, "hPSM)0.0" should read --hPSM÷0.0--.

UNITED STATES PATENT AND TRADEMARK OFFICE
CERTIFICATE OF CORRECTION

PATENT NO. : 7,005,498 B1
APPLICATION NO. : 09/806703
DATED : February 28, 2006
INVENTOR(S) : Lucilla Steinaa et al.

It is certified that error appears in the above-identified patent and that said Letters Patent is hereby corrected as shown below:

At Column 58, Line 52, "TNF∀" should read --TNFα--.

At Column 58, Line 63, "40:g" should read --40μg--.

At Column 59, Lines 19-20, "hPSM)0.0" should read --hPSM÷0.0--.

At Column 60, Line 15, "PROS)0.0" should read --PROS÷0.0--.

At Column 62, Lines 41-42, "(3-galactosidase)" should read --β-galactosidase--.

At Column 62, Line 53, "(Ǝ-galactosidase)" should read --β-galactosidase--.

At Column 63, Line 6, ")" should read --÷--.

At Column 63, Line 7, ")" should read --÷--.

At Column 63, Line 61, "pcDNA3.1())" should read --pcDNA3.1(÷)--.

At Column 66, Line 23, "∀-helix and Ǝ-sheet" should read --α-helix and β-sheet--.

At Column 66, Line 41, "∀-helix or Ǝ-sheet" should read --α-helix or β-sheet--.

At Column 72, Line 59, "100:g" should read --100μg--.

At Column 72, Line 60, "100:1 volume+100:1" should read --100μl volume+100μl--.

At Column 72, Line 61, "200:1" should read --200μl--.

At Column 73, Line 4, "50-100: 1" should read --50-100μl--.

UNITED STATES PATENT AND TRADEMARK OFFICE
CERTIFICATE OF CORRECTION

PATENT NO. : 7,005,498 B1
APPLICATION NO. : 09/806703
DATED : February 28, 2006
INVENTOR(S) : Lucilla Steinaa et al.

It is certified that error appears in the above-identified patent and that said Letters Patent is hereby corrected as shown below:

At Column 73, Line 6, "10-20:1" should read --10-20µl--.

Signed and Sealed this

Thirtieth Day of December, 2008

JON W. DUDAS
*Director of the United States Patent and Trademark Office*